(12) United States Patent
Utsumi et al.

(10) Patent No.: US 8,900,795 B2
(45) Date of Patent: Dec. 2, 2014

(54) RESIST COMPOSITION, METHOD OF FORMING RESIST PATTERN AND NOVEL COMPOUND

(71) Applicant: Tokyo Ohka Kogyo Co., Ltd., Kawasaki-shi (JP)

(72) Inventors: Yoshiyuki Utsumi, Kawasaki (JP); Hiroaki Shimizu, Kawasaki (JP); Jiro Yokoya, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 137 days.

(21) Appl. No.: 13/738,438

(22) Filed: Jan. 10, 2013

(65) Prior Publication Data

US 2013/0177854 A1  Jul. 11, 2013

(30) Foreign Application Priority Data

Jan. 11, 2012  (JP) ................. 2012-003413

(51) Int. Cl.
*G03F 7/004* (2006.01)
*C07C 309/06* (2006.01)
*C07C 309/17* (2006.01)

(52) U.S. Cl.
CPC .............. *G03F 7/004* (2013.01); *G03F 7/0045* (2013.01); *C07C 309/06* (2013.01); *C07C 309/17* (2013.01)
USPC .......... 430/270.1; 430/322; 560/149; 568/30; 568/31

(58) Field of Classification Search
None
See application file for complete search history.

(56) References Cited

U.S. PATENT DOCUMENTS 6,949,325 B2  9/2005 Li et al.
(Continued)

FOREIGN PATENT DOCUMENTS

JP  A-06-194847  7/1994
(Continued)

OTHER PUBLICATIONS

Machine translation JP 2012-136506. Jul. 19, 2012.*
(Continued)

*Primary Examiner* — Anca Eoff
*Assistant Examiner* — Alyssa L Cepluch
(74) *Attorney, Agent, or Firm* — Knobbe Martens Olson & Bear LLP

(57) ABSTRACT

A resist composition including a base component (A) which exhibits changed solubility in a developing solution, and an acidic compound component (J) which is decomposed by exposure to exhibit decreased acidity, wherein the acidic compound component (J) contains a compound represented by formula (J1) [in the formula, $R^1$ represents H, OH, halogen atom, alkoxy group, hydrocarbon group or nitro group; m represents 0-4; n represents 0-3; Rx represents H or hydrocarbon group; $X^1$ represents divalent linking group; $X^2$ represents H or hydrocarbon group; Y represents single bond or C(O); A represents alkylene group which may be substituted with oxygen atom, carbonyl group or alkylene group which may have fluorine atom; $Q^1$ and $Q^2$ represents F or fluorinated alkyl group; and $W^+$ represents primary, secondary or tertiary ammonium coutercation which exhibits pKa smaller than pKa of $H_2N^+(X^2)—X^1—Y—O—A—C(Q^1)(Q^2)—SO_3^-$ generated by decomposition upon exposure].

(J1)

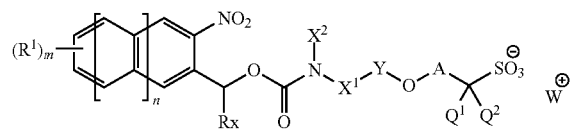

3 Claims, 1 Drawing Sheet

(56) References Cited

U.S. PATENT DOCUMENTS

| | | |
|---|---|---|
| 2001/0049073 A1 | 12/2001 | Hada et al. |
| 2004/0110085 A1 | 6/2004 | Iwai et al. |
| 2008/0187860 A1 | 8/2008 | Tsubaki et al. |
| 2010/0035192 A1 | 2/2010 | Ando et al. |

FOREIGN PATENT DOCUMENTS

| | | |
|---|---|---|
| JP | A-2000-206694 | 7/2000 |
| JP | A-2000-330270 | 11/2000 |
| JP | A-2003-241385 | 8/2003 |
| JP | A-2005-336452 | 12/2005 |
| JP | A-2006-259582 | 9/2006 |
| JP | A-2006-317803 | 11/2006 |
| JP | A-2007-279493 | 10/2007 |
| JP | A-2008-174515 | 7/2008 |
| JP | A-2008-292975 | 12/2008 |
| JP | A-2009-025723 | 2/2009 |
| JP | A-2010-040849 | 2/2010 |
| JP | 2012136506 A * | 7/2012 |

OTHER PUBLICATIONS

Borodovsky, "Marching to the beat of Moore's Law" Proceedings of SPIE (U.S.), vol. 6153, pp. 615301-1 to 615301-19 (2006).

Ebihara et al., "Beyond $k_1$=0.25 lithography : 70nm L/S patterning using KrF scanners" Proceedings of SPIE (U.S.), vol. 5256, pp. 985-994 (2003).

Gil et al., "First Microprocessors with Immersion Lithography" Proceedings of SPIE (U.S.), vol. 5754, pp. 119-128 (2005).

* cited by examiner

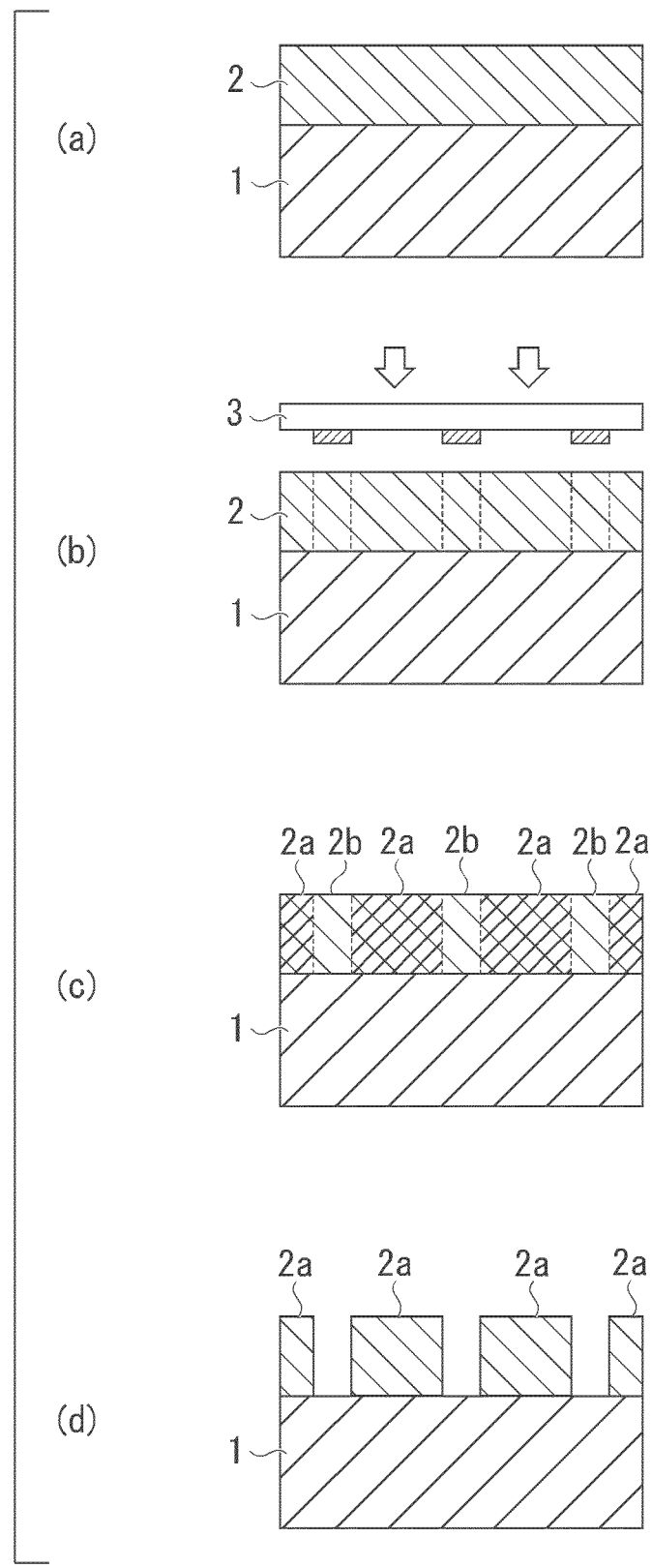

RESIST COMPOSITION, METHOD OF FORMING RESIST PATTERN AND NOVEL COMPOUND

TECHNICAL FIELD

The present invention relates to a resist composition exhibiting excellent lithography properties, a method of forming a resist pattern using the resist composition, and a novel compound useful for the resist composition.

Priority is claimed on Japanese Patent Application No. 2012-003413, filed on Jan. 11, 2012, the content of which is incorporated herein by reference.

BACKGROUND ART

Techniques (pattern-forming techniques) in which a fine pattern is formed on top of a substrate, and a lower layer beneath that pattern is then fabricated by conducting etching with this pattern as a mask are widely used in the production of semiconductor devices and liquid display device. These types of fine patterns are usually formed from an organic material, and are formed, for example, using a lithography method or a nanoimprint method or the like. In lithography techniques, for example, a resist film composed of a resist material containing a base component such as a resin is formed on a support such as a substrate, and the resist film is subjected to selective exposure of radial rays such as light or electron beam, followed by development, thereby forming a resist pattern having a predetermined shape on the resist film. Using this resist pattern as a mask, a semiconductor or the like is produced by conducting a step in which the substrate is processed by etching.

The aforementioned resist material can be classified into positive types and negative types. Resist materials in which the exposed portions exhibit increased solubility in a developing solution is called a positive type, and a resist material in which the exposed portions exhibit decreased solubility in a developing solution is called a negative type.

In general, an aqueous alkali solution (alkali developing solution) such as an aqueous solution of tetramethylammonium hydroxide (TMAH) is used as the developing solution. Alternatively, organic solvents such as aromatic solvents, aliphatic hydrocarbon solvents, ether solvents, ketone solvents, ester solvents, amide solvents and alcohol solvents are used as the developing solution (for example, see Patent Documents 1 and 2).

In recent years, advances in lithography techniques have lead to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam (EB), extreme ultraviolet radiation (EUV), and X ray.

As shortening the wavelength of the exposure light source progresses, it is required to improve various lithography properties of the resist material, such as the sensitivity to the exposure light source and a resolution capable of reproducing patterns of minute dimensions. As resist materials which satisfy such requirements, chemically amplified resists are known.

As a chemically amplified composition, a composition including a base material component that exhibits a changed solubility in a developing solution under the action of acid and an acid-generator component that generates acid upon exposure is generally used. For example, in the case where an alkali developing solution is used as a developing solution (alkali developing process), a base component which exhibits increased solubility in an alkali developing solution under action of acid is used.

Conventionally, a resin (base resin) is typically used as the base component of a chemically amplified resist composition. Resins that contain structural units derived from (meth) acrylate esters within the main chain (acrylic resins) are the mainstream as base resins for chemically amplified resist compositions that use ArF excimer laser lithography, as they exhibit excellent transparency in the vicinity of 193 nm.

Here, the term "(meth)acrylic acid" is a generic term that includes either or both of acrylic acid having a hydrogen atom bonded to the α-position and methacrylic acid having a methyl group bonded to the α-position. The term "(meth) acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position.

In general, the base resin contains a plurality of structural units for improving lithography properties and the like. For example, a structural unit having a lactone structure and a structural unit having a polar group such as a hydroxy group are used, as well as a structural unit having an acid decomposable group which is decomposed by the action of an acid generated from the acid generator to form an alkali soluble group (for example, see Patent Document 3). When the base resin is an acrylic resin, as the acid decomposable group, in general, resins in which the carboxy group of (meth)acrylic acid or the like is protected with an acid dissociable group such as a tertiary alkyl group or an acetal group are used.

As a technique for further improving the resolution, a lithography method called liquid immersion lithography (hereafter, frequently referred to as "immersion exposure") is known in which exposure (immersion exposure) is conducted in a state where the region between the lens and the resist layer formed on a wafer is filled with a solvent (a immersion medium) that has a larger refractive index than the refractive index of air (see for example, Non-Patent Document 1).

According to this type of immersion exposure, it is considered that higher resolutions equivalent to those obtained using a shorter wavelength light source or a larger NA lens can be obtained using the same exposure light source wavelength, with no lowering of the depth of focus. Furthermore, immersion exposure can be conducted by applying a conventional exposure apparatus. As a result, it is expected that immersion exposure will enable the formation of resist patterns of higher resolution and superior depth of focus at lower costs. Accordingly, in the production of semiconductor devices, which requires enormous capital investment, immersion exposure is attracting considerable attention as a method that offers significant potential to the semiconductor industry, both in terms of cost and in terms of lithography properties such as resolution.

Immersion lithography is effective in forming patterns having various shapes. Further, immersion exposure is expected to be capable of being used in combination with currently studied super-resolution techniques, such as phase shift method and modified illumination method. Currently, as the immersion exposure technique, technique using an ArF excimer laser as an exposure source is being actively studied. Further, water is mainly used as the immersion medium.

As a lithography technique which has been recently proposed, a double patterning method is known in which patterning is conducted two or more times to form a resist pattern (for example, see Non-Patent Documents 2 and 3). There are several different types of double patterning process, for example, (1) a method in which a lithography step (from application of resist compositions to exposure and developing) and an etching step are performed twice or more to form a pattern and (2) a method in which the lithography step is successively performed twice or more. According to the double patterning method, a resist pattern with a higher level of resolution can be formed, as compared to the case where a resist pattern is formed by a single lithography step (namely, a single patterning process), even when a light source with the same exposure wavelength is used, or even when the same resist composition is used. Furthermore, double patterning process can be conducted using a conventional exposure apparatus.

Moreover, a double exposure process has also been proposed in which a resist film is formed, and the resist film is subjected to exposure twice or more, followed by development to form a resist pattern (for example, see Patent Document 4). Like the double patterning process described above, this type of double exposure process is also capable of forming a resist pattern with a high level of resolution, and also has an advantage in that fewer number of steps is required than the above-mentioned double patterning process.

In a positive tone development process using a positive type, chemically amplified resist composition (i.e., a chemically amplified resist composition which generates acid upon exposure and exhibits increased alkali solubility in an alkali developing solution by the action of the acid) in combination with an alkali developing solution, as described above, the exposed portions of the resist film are dissolved and removed by an alkali developing solution to thereby form a resist pattern. The positive tone process using a combination of a positive chemically amplified resist composition and an alkali developing solution is advantageous over a negative tone development process in which a negative type, chemically amplified resist composition is used in combination with an alkali developing solution in that the structure of the photomask can be simplified, a satisfactory contrast for forming an image can be reliably obtained, and the characteristics of the formed resist pattern are excellent. For these reasons, currently, positive-tone development process using a combination of a positive chemically amplified resist composition and an alkali developing solution is mainly employed in the formation of an extremely fine resist pattern.

In the formation of the aforementioned extremely small pattern (e.g., an isolated trench pattern, an extremely fine, densed contact hole pattern, and the like), a method of forming a resist pattern (negative pattern) in which regions where the optical strength becomes weak are selectively dissolved and removed is useful. For forming a negative pattern with a chemically amplified resist composition (which generates acid upon exposure and exhibits increased alkali solubility in an alkali developing solution by the action of the acid) used in a positive-tone developing process which is the mainstream, a method in which a developing solution containing an organic solvent (organic developing solution) is used in combination with a chemically amplified resist composition is known (see for example, Patent Document 5).

DOCUMENTS OF RELATED ART

Patent Document

[Patent Document 1] Japanese Unexamined Patent Application, First Publication No. Hei 6-194847
[Patent Document 2] Japanese Unexamined Patent Application, First Publication No. 2009-025723
[Patent Document 3] Japanese Unexamined Patent Application, First Publication No. 2003-241385
[Patent Document 4] Japanese Unexamined Patent Application, First Publication No. 2010-040849
[Patent Document 5] Japanese Unexamined Patent Application, First Publication No. 2008-292975

Non-Patent Documents

[Non-Patent Document 1] Proceedings of SPIE (U.S.), vol. 5754, pp. 119-128 (2005)
[Non-Patent Document 2] Proceedings of SPIE (U.S.), vol. 5256, pp. 985-994 (2003)
[Non-Patent Document 3] Proceedings of SPIE (U.S.), vol. 615301-1-19 (2006)

SUMMARY OF THE INVENTION

However, as further progress is made in lithography techniques and the application field for lithography techniques expand, further improvement in various lithography properties is demanded in a positive-tone developing process using a combination of a positive chemically amplified resist composition and an alkali developing solution, and in a negative-tone developing process using a combination of a chemically amplified resist composition for positive-tone developing process and an organic developing solution.

The present invention takes the above circumstances into consideration, with an object of providing a resist composition exhibiting excellent lithography properties, a method of forming a resist pattern using the resist composition, and a novel compound useful for the resist composition.

As a result of intensive studies of the present inventors, they have found that, by using a specific acidic compound component which is decomposed by exposure to exhibit decreased acidity instead of an acid generator component, a negative-tone pattern can be formed using an alkali developing solution (and a positive-tone pattern can be formed by using an organic developing solution), and various lithography properties can be improved. The present invention has been completed based on these findings.

Specifically, a first aspect of the present invention is a resist composition including a base component (A) which exhibits changed solubility in a developing solution, and an acidic compound component (J) which is decomposed by exposure to exhibit decreased acidity, wherein the acidic compound component (J) contains a compound represented by general formula (J1) shown below.

[Chemical Formula 1]

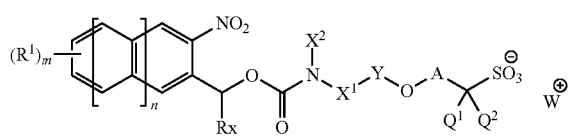

(J1)

In the formula, $R^1$ represents a hydrogen atom, a hydroxy group, a halogen atom, a linear or branched alkoxy group, a hydrocarbon group which may have a substituent, or a nitro group; m represents an integer of 0 to 4; n represents an integer of 0 to 3; Rx represents a hydrogen atom or a hydrocarbon group which may have a substituent; $X^1$ represents a divalent linking group and $X^2$ represents a hydrogen atom or a hydrocarbon group which may have a substituent, provided that $X^1$ and $X^2$ may be mutually bonded to form a ring with the nitrogen atom; Y represents a single bond or a carbonyl group, and A represents an alkylene group of 1 to 6 carbon atoms, provided that part of the methylene group constituting the alkylene group may be replaced with an oxygen atom or a carbonyl group, part or all of the hydrogen atoms constituting the alkylene group may be substituted with an aliphatic hydrocarbon group of 1 to 6 carbon atoms which may have a fluorine atom, and —Y—O-A- does not represent —C(=O)—O—C(=O)—; $Q^1$ and $Q^2$ each independently represents a fluorine atom or a linear or branched fluorinated alkyl group of 1 to 6 carbon atoms; and $W^+$ represents a primary, secondary or tertiary ammonium coutercation which exhibits a pKa smaller than a pKa of $H_2N^+(X^2)$—$X^1$—Y—O-A-C($Q^1$)($Q^2$)—$SO_3^-$ generated by decomposition upon exposure.

A second aspect of the present invention is a method of forming a resist pattern, including: using a resist composition of the first aspect to form a resist film on a substrate; conducting exposure of the resist film; and developing the resist film to form a resist pattern.

A third aspect of the present invention is a compound represented by general formula (i1) shown below.

[Chemical Formula 2]

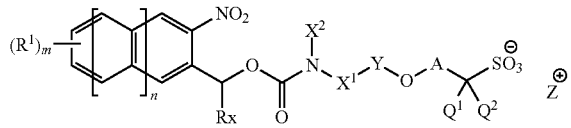

(i1)

In the formula, $R^1$ represents a hydrogen atom, a hydroxy group, a halogen atom, a linear or branched alkoxy group, a hydrocarbon group which may have a substituent, or a nitro group; m represents an integer of 0 to 4; n represents an integer of 0 to 3; Rx represents a hydrogen atom or a hydrocarbon group which may have a substituent; $X^1$ represents a divalent linking group and $X^2$ represents a hydrogen atom or a hydrocarbon group which may have a substituent, provided that $X^1$ and $X^2$ may be mutually bonded to form a ring with the nitrogen atom; Y represents a single bond or a carbonyl group, and A represents an alkylene group of 1 to 6 carbon atoms, provided that part of the methylene group constituting the alkylene group may be replaced with an oxygen atom or a carbonyl group, part or all of the hydrogen atoms constituting the alkylene group may be substituted with an aliphatic hydrocarbon group of 1 to 6 carbon atoms which may have a fluorine atom, and —Y—O-A- does not represent —C(=O)—O—C(=O)—; $Q^1$ and $Q^2$ each independently represents a fluorine atom or a linear or branched fluorinated alkyl group of 1 to 6 carbon atoms; and $Z^+$ represents a metal cation or an onium cation.

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic divalent saturated hydrocarbon, unless otherwise specified.

A "halogenated alkyl group" is a group in which part or all of the hydrogen atoms of an alkyl group is substituted with a halogen atom, and a "halogenated alkylene group" is a group in which part or all of the hydrogen atoms of an alkylene group is substituted with a halogen atom. Examples of the halogen atom include a fluorine atom, a chlorine atom, a bromine atom and an iodine atom.

A "hydroxyalkyl group" is a group in which part or all of the hydrogen atoms within an alkyl group have been substituted with a hydroxyl group.

The term "structural unit" refers to a monomer unit that contributes to the formation of a polymeric compound (resin, polymer, copolymer).

The term "exposure" is used as a general concept that includes irradiation with any form of radiation.

An "acidic compound" refers to a compound which exhibits acidity itself, i.e., a compound that acts as a proton donor.

The "acidic compound is decomposed to exhibit decreased acidity" means that at least part of the bonds within the structure of the acidic compound is cleaved to exhibit decreased acidity, i.e., the proton donor ability becomes low. The acidity can be compared, for example, by the level of the pKa value. In the present invention, pKa refers to an acid dissociation constant which is generally used as a parameter which shows the acid strength of an objective substance. The pKa value of the acidic compound component (J) described later or the decomposition product of the acidic compound component (J) described later can be determined by a conventional method. Alternatively, the pKa value can be estimated by calculation using a conventional software such as "ACD/Labs" (trade name; manufactured by Advanced Chemistry Development, Inc.).

According to the present invention, there are provided a resist composition exhibiting excellent lithography properties, a method of forming a resist pattern using the resist composition, and a novel compound useful for the resist composition.

BRIEF DESCRIPTION OF THE DRAWINGS

FIG. 1 is a schematic diagram showing an example of one embodiment of the method of forming a resist pattern according to the present invention.

MODE FOR CARRYING OUT THE INVENTION

<<Resist Composition>>

The resist composition according to the first aspect of the present invention includes a base component (A) which exhibits changed solubility in a developing solution under action of acid (hereafter, referred to as "component (A)") and an acid compound component (J) which is decomposed by exposure to exhibit decreased acidity (hereafter, referred to as "component (J)").

A resist film formed using the resist composition contains the component (J) having a proton donor ability. When a selective exposure is conducted during formation of a resist pattern, the acidity of the component (J) is decreased at exposed regions (exposed portions), thereby causing decrease or loss of the proton donor ability. As a result, at unexposed portions of the resist film, by the action of the component (J) present in the resist film in advance, the solubility of the component (A) in a developing solution is changed, thereby changing the solubility of the unexposed portions in a developing solution. On the other hand, at exposed portions, since the acidity of the component (J) is decreased, the solubility of the component (A) in a developing is either unchanged or only slightly changed. Therefore, by subjecting the resist film to development, the exposed portions are dissolved and removed to form a positive-tone resist pattern in the case of a positive resist, whereas the unexposed portions are dissolved and removed to form a negative-tone resist pattern in the case of a negative resist.

In the present specification, a resist composition which forms a positive resist pattern by dissolving and removing the exposed portions is called a positive resist composition, and a resist composition which forms a negative resist pattern by dissolving and removing the unexposed portions is called a negative resist composition. The resist composition of the present invention may be either a positive resist composition or a negative resist composition. Further, in the formation of a resist pattern, the resist composition of the present invention can be applied to an alkali developing process using an alkali developing solution in the developing treatment, or a solvent developing process using a developing solution containing an organic solvent (organic developing solution) in the developing treatment. The resist composition of the present invention is preferably used in the formation of a negative-tone resist pattern by an alkali developing process. In such a case, as the component (A), a base component that exhibits increased solubility in an alkali developing solution under the action of acid is used.

<Component (A); Base Component>

As the component (A), an organic compound typically used as a base component for a resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The "organic compound having a molecular weight of 500 or more" which can be used as a base component is broadly classified into non-polymers and polymers.

In general, as a non-polymer, any of those which have a molecular weight in the range of 500 to less than 4,000 is used. Hereafter, a non-polymer having a molecular weight in the range of 500 to less than 4,000 is referred to as a low molecular weight compound.

As a polymer, any of those which have a molecular weight of 1,000 or more is generally used. Hereafter, a polymer having a molecular weight of 1,000 or more is referred to as a polymeric compound. With respect to a polymeric compound, the "molecular weight" is the weight average molecular weight in terms of the polystyrene equivalent value determined by gel permeation chromatography (GPC). Hereafter, a polymeric compound is frequently referred to simply as a "resin".

As the component (A), a resin component which exhibits changed solubility in a developing solution under action of acid may be used. Alternatively, as the component (A), a low molecular weight material which exhibits changed solubility in a developing solution under action of acid may be used.

The component (A) may be a resin that exhibits increased solubility in a developing solution under action of acid or a resin that exhibits decreased solubility in a developing solution under action of acid.

When the resist composition of the present invention is a resist composition that forms a positive-tone resist pattern in an alkali developing process (or a negative-tone resist pattern in a solvent developing process), as the component (A), a base component that is soluble in an alkali developing solution (hereafter, this base component is sometimes referred to as component "component (A0')") is used, and a cross-linking component is further added. In such a resist composition, the action of the component (J) causes cross-linking between the component (A0') and the cross-linking component. As a result, the solubility of the resist composition in an alkali developing solution is decreased (the solubility of the resist composition in an organic developing solution is increased). Therefore, in the formation of a resist pattern, by conducting selective exposure of a resist film formed by applying the resist composition to a substrate, the unexposed portions where the acidity of the component (J) has not decreased become insoluble in an alkali developing solution (soluble in an organic developing solution), whereas the exposed portions where the acidity of the component (J) has decreased remain soluble in an alkali developing solution (insoluble in an organic developing solution), and hence, a positive resist pattern can be formed by conducting development using an alkali developing solution. On the other hand, when an organic developing solution is used as the developing solution, a negative resist pattern can be formed.

As the component (A0'), a resin soluble in an alkali developing solution (hereafter, referred to as "alkali-soluble resin") known in the art can be used.

Examples of the alkali soluble resin include a resin having a structural unit derived from at least one of α-(hydroxyalkyl)acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; an acrylic resin which has a sulfonamide group and may have an atom other than hydrogen or a substituent bonded to the carbon atom on the α-position or polycycloolefin resin having a sulfoneamide group, as disclosed in U.S. Pat. No. 6,949,325; an acrylic resin which may have an atom other than hydrogen or a substituent bonded to the carbon atom on the α-position and having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which an atom other than hydrogen or a substituent is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the crosslinker added is preferably within a range from 1 to 50 parts by weight, relative to 100 parts by weight of the alkali-soluble resin.

When the resist composition of the present invention is a resist composition that forms a negative-tone resist pattern in an alkali developing process and a positive-tone resist pattern in a solvent developing process, as the component (A), a base component (A0) that exhibits increased polarity by the action of acid (hereafter, this base component is referred to as "component (A0)") is preferably used. The component (A0) exhibits changed polarity by the action of acid (acidic compound component). Therefore, an excellent development contrast can be obtained not only in an alkali developing process, but also in a solvent developing process.

More specifically, in the case of applying an alkali developing process, as the component (A0), a base component that is hardly soluble in an alkali developing solution prior to action of acid is used. By the action of the component (J), the component (A0) exhibits increased polarity, and the solubility in an alkali developing solution is increased. Therefore, in the formation of a resist pattern, by conducting selective exposure of a resist film formed by applying the resist composition to a substrate, the unexposed portions where the acidity of the component (J) has not decreased change from an insoluble state to a soluble state in an alkali developing solution, whereas the exposed portions where the acidity of the component (J) has decreased remain insoluble in an alkali developing solution, and hence, a negative-tone pattern can be formed by alkali developing.

On the other hand, in the case of applying a solvent developing process, as the component (A0), a base component that is highly soluble in an organic developing solution prior to action of acid is used. By the action of the component (J), the component (A0) exhibits increased polarity, and the solubility in an organic developing solution is decreased. Therefore, in the formation of a resist pattern, by conducting selective exposure of a resist film formed by applying the resist composition to a substrate, the unexposed portions where the acidity of the component (J) has not decreased change from a soluble state to an insoluble state in an organic developing solution, whereas the exposed portions where the acidity of the component (J) has decreased remain soluble in an organic developing solution, and hence, a contrast can be obtained between the exposed portions and the unexposed portions, and a positive-tone pattern can be formed.

In the resist composition of the present invention, the component (A) is preferably a component (A0). That is, the resist composition of the present invention is preferably a chemically amplified resist composition which becomes a negative type in the case of an alkali developing process, and a positive type in the case of a solvent developing process.

By using the resist composition of the present invention, an opposite pattern from that conventionally obtained can be formed using a base component for a resist composition conventionally used in the formation of a positive-tone pattern by an alkali developing process (a negative-tone pattern using a solvent developing process), i.e., a base component which becomes soluble in an alkali developing solution by the action of acid (insoluble in an organic solvent by the action of acid). As such, by using an alkali developing solution which is advantageous over an organic developing solution in terms of environment, apparatus and cost, and a conventional base component, a negative-tone pattern suitable for formation of a fine pattern (an isolated trench pattern, a fine densed pattern or the like) can be formed.

In the present invention, the component (A0) may be a resin component (A1) that exhibits increased polarity under the action of acid (hereafter, frequently referred to as "component (A1)"), a low molecular weight material (A2) that exhibits increased polarity under the action of acid (hereafter, frequently referred to as "component (A2)"), or a mixture thereof.

[Component (A1)]

As the component (A1), a resin component (base resin) typically used as a base component for a chemically amplified resist composition can be used alone, or two or more of such resin components can be mixed together.

In the present invention, the component (A1) preferably has a structural unit (a1) containing an acid decomposable group that exhibits increased polarity by the action of acid.

The component (A1) preferably has, in addition to the structural unit (a1), at least one structural unit selected from the group consisting of a structural unit (a0) containing an —$SO_2$— containing cyclic group and a structural unit (a2) containing a lactone-containing cyclic group.

Further, the component (A1) preferably has, in addition to the structural unit (a1) or in addition to the structural unit (a1) and at least one structural unit selected from the group consisting of the structural unit (a0) and the structural unit (a2), a structural unit (a3) containing a polar group-containing aliphatic hydrocarbon group.

Furthermore, it is also preferable that the component (A1) has a structural unit (a5) which generates base upon exposure.

(Structural Unit (a1))

The structural unit (a1) is a structural unit containing an acid decomposable group that exhibits increased polarity by the action of acid.

The term "acid decomposable group" refers to a group in which at least a part of the bond within the structure thereof is cleaved by the action of an acid.

Examples of acid decomposable groups which exhibit increased polarity by the action of an acid include groups which are decomposed by the action of an acid to form a polar group.

Examples of the polar group which constitute the acid decomposable group include a carboxy group, a hydroxy group, an amino group and a sulfo group (—$SO_3H$). Among these, a carboxy group or a hydroxy group is preferable, and a carboxy group is particularly desirable.

More specifically, as an example of an acid decomposable group, a group in which the aforementioned polar group has been protected with an acid dissociable group (such as a group in which the hydrogen atom of the aforementioned polar group has been protected with an acid dissociable group) can be given.

An "acid dissociable group" is a group in which at least the bond between the acid dissociable group and the adjacent carbon atom is cleaved by the action of acid. It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity of the component (A). By the increase in the polarity of the component (A), the solubility of the portion where acid has acted (unexposed portion) in an alkali developing solution is increased in the case of an alkali developing process, and the solubility of the portion where acid has acted (unexposed portion) in an organic developing solution is decreased in the case of a solvent developing process.

The acid dissociable group is not particularly limited, and any of the groups that have been conventionally proposed as acid dissociable groups for the base resins of chemically amplified resists can be used. Generally, groups that form either a cyclic or chain-like tertiary alkyl ester with the carboxyl group of the (meth)acrylic acid, and acetal-type acid dissociable groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(=O)—O—). In this tertiary alkyl ester, the action of acid causes cleavage of the bond between the oxygen atom and the tertiary carbon atom, thereby forming a carboxy group.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable groups".

Examples of tertiary alkyl ester-type acid dissociable groups include aliphatic branched, acid dissociable groups and aliphatic cyclic group-containing acid dissociable groups.

The term "aliphatic branched" refers to a branched structure having no aromaticity. The "aliphatic branched, acid dissociable group" is not limited to be constituted of only carbon atoms and hydrogen atoms (not limited to hydrocarbon groups), but is preferably a hydrocarbon group. Further, the "hydrocarbon group" may be either saturated or unsaturated, but is preferably saturated.

As an example of the aliphatic branched, acid dissociable group, for example, a group represented by the formula —C($R^{71}$)($R^{72}$)($R^{73}$) can be given. (in the formula, each of $R^{71}$ to $R^{73}$ independently represents a linear alkyl group of 1 to 5 carbon atoms). The group represented by the formula —C($R^{71}$)($R^{72}$)($R^{73}$) preferably has 4 to 8 carbon atoms, and specific examples include a tert-butyl group, a 2-methyl-2-butyl group, a 2-methyl-2-pentyl group and a 3-methyl-3-pentyl group.

Among these, a tert-butyl group is particularly desirable.

The term "aliphatic cyclic group" refers to a monocyclic group or polycyclic group that has no aromaticity.

In the "aliphatic cyclic group-containing acid dissociable group", the "aliphatic cyclic group" may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated.

The aliphatic cyclic group may be either a monocyclic group or a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated alkyl group, may be used. Specific examples of aliphatic cyclic hydrocarbon groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. In these aliphatic cyclic hydrocarbon groups, part of the carbon atoms constituting the ring may be replaced with an ethereal oxygen atom (—O—).

Examples of aliphatic cyclic group-containing acid dissociable groups include (i) a monovalent aliphatic cyclic group in which a substituent (a group or an atom other than hydrogen) is bonded to the carbon atom on the ring skeleton to which an atom adjacent to the acid dissociable group (e.g., "—O—" within "—C(=O)—O— group") is bonded to form a tertiary carbon atom; and (ii) a group which has a branched alkylene group containing a tertiary carbon atom, and a monovalent aliphatic cyclic group to which the tertiary carbon atom is bonded.

In the group (i), as the substituent bonded to the carbon atom to which an atom adjacent to the acid dissociable group on the ring skeleton of the aliphatic cyclic group, an alkyl group can be mentioned. Examples of the alkyl group include the same groups as those represented by $R^{14}$ in formulas (1-1) to (1-9) described later.

Specific examples of the group (i) include groups represented by general formulas (1-1) to (1-9) shown below.

Specific examples of the group (ii) include groups represented by general formulas (2-1) to (2-6) shown below.

[Chemical Formula 3]

 (1-1)

 (1-2)

 (1-3)

 (1-4)

 (1-5)

 (1-6)

-continued (1-7)
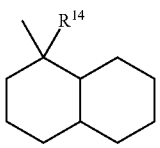

(1-8)
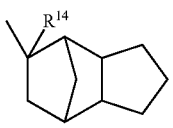

(1-9)
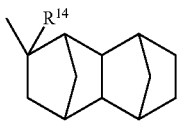

In the formulas above, $R^{14}$ represents an alkyl group; and g represents an integer of 0 to 8.

[Chemical Formula 4]

(2-1)
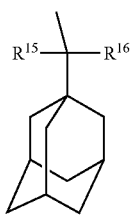

(2-2)
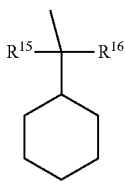

(2-3)
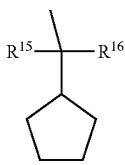

(2-4)
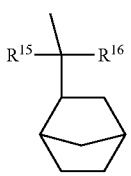

(2-5)
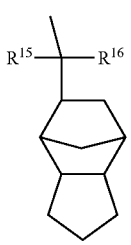

-continued (2-6)
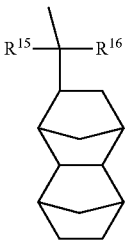

In the formulas above, each of $R^{15}$ and $R^{16}$ independently represents an alkyl group.

In formulas (1-1) to (1-9), the alkyl group for $R^{14}$ may be linear, branched or cyclic, and is preferably linear or branched.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group is particularly desirable.

g is preferably an integer of 0 to 3, more preferably 1 to 3, and still more preferably 1 or 2.

In formulas (2-1) to (2-6), as the alkyl group for $R^{15}$ and $R^{16}$, the same alkyl groups as those for $R^{14}$ can be used.

In formulas (1-1) to (1-9) and (2-1) to (2-6), part of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of the substituent include an alkyl group of 1 to 5 carbon atoms, a fluorine atom and a fluorinated alkyl group.

An "acetal-type acid dissociable group" generally substitutes a hydrogen atom at the terminal of an OH-containing polar group such as a carboxy group or hydroxyl group, so as to be bonded with an oxygen atom. When acid acts to break the bond between the acetal-type acid dissociable group and the oxygen atom to which the acetal-type, acid dissociable group is bonded, an OH-containing polar group such as a carboxy group or a hydroxy group is formed.

Examples of acetal-type acid dissociable groups include groups represented by general formula (p1) shown below.

[Chemical Formula 5]

(p1)
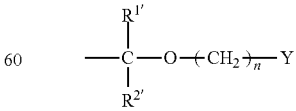

In the formula, $R^{1\prime}$ and $R^{2\prime}$ each independently represent a hydrogen atom or an alkyl group of 1 to 5 carbon atoms; n represents an integer of 0 to 3; and Y represents an alkyl group of 1 to 5 carbon atoms or an aliphatic cyclic group.

In general formula (p1), n is preferably an integer of 0 to 2, more preferably 0 or 1, and most preferably 0.

As the lower alkyl group for $R^{1'}$ and $R^{2'}$, the same lower alkyl groups as those described above the alkyl groups as the substituent which may be bonded to the carbon atom on the α-position of the aforementioned α-substituted alkylester can be used, although a methyl group or ethyl group is preferable, and a methyl group is particularly desirable.

In the present invention, it is preferable that at least one of $R^{1'}$ and $R^{2'}$ be a hydrogen atom. That is, it is preferable that the acid dissociable group (p1) is a group represented by general formula (p1-1) shown below.

[Chemical Formula 6]

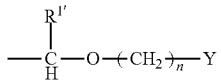

(p1-1)

In the formula, $R^{1'}$, n and Y are the same as defined above.

As the alkyl group for Y, the same alkyl groups as those described above the for the substituent which may be bonded to the carbon atom on the α-position of the aforementioned α-substituted alkylester can be mentioned.

As the aliphatic cyclic group for Y, any of the aliphatic monocyclic/polycyclic groups which have been proposed for conventional ArF resists and the like can be appropriately selected for use. For example, the same aliphatic cyclic groups described above in connection with the "acid dissociable group containing an aliphatic cyclic group" can be used.

Further, as the acetal-type, acid dissociable group, groups represented by general formula (p2) shown below can also be used.

[Chemical Formula 7]

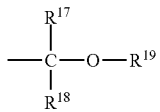

(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of the cyclic group include tetrahydropyranyl group and tetrahydrofuranyl group.

Examples of the structural unit (a1) include a structural unit derived from an acrylate ester which may have the hydrogen atom bonded to the carbon atom on the α-position substituted with a substituent and contains an acid decomposable group which exhibits increased polarity by the action of acid; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

Preferable examples of the substituent containing an acid decomposable group include the tertiary alkyl ester-type acid dissociable group and the acetal-type acid dissociable group described above.

In the present descriptions and the claims, the expression "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid ($CH_2=CH—COOH$) has been substituted with an organic group.

The acrylate ester may have the hydrogen atom bonded to the carbon atom on the α-position substituted with a substituent. The substituent that substitutes the hydrogen atom bonded to the carbon atom on the α-position is atom other than hydrogen or a group, and examples thereof include an alkyl group of 1 to 5 carbon atoms, a halogenated alkyl group of 1 to 5 carbon atoms and a hydroxyalkyl group. A carbon atom on the α-position of an acrylate ester refers to the carbon atom bonded to the carbonyl group, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

In the α-substituted acrylate ester, the alkyl group as the substituent on the α-position is preferably a linear or branched alkyl group, and specific examples thereof include a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group of 1 to 5 carbon atoms as the substituent on the α-position include groups in which part or all of the hydrogen atoms of the aforementioned "alkyl group of 1 to 5 carbon atoms as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group of 1 to 5 carbon atoms as the substituent on the α-position include groups in which part or all of the hydrogen atoms of the aforementioned "alkyl group of 1 to 5 carbon atoms as the substituent on the α-position" are substituted with a hydroxy group. The number of hydroxy groups within the hydroxyalkyl group is preferably 1 to 5, and most preferably 1.

It is preferable that a hydrogen atom, an alkyl group of 1 to 5 carbon atoms or a halogenated alkyl group of 1 to 5 carbon atoms is bonded to the α-position of the α-substituted acrylate ester, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

A "structural unit derived from hydroxystyrene or a hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxy group has been substituted with an organic group and may have the hydrogen atom on the α-position substituted with a substituent; and hydroxystyrene which has a substituent other than a hydroxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylate ester can be mentioned. Among these, a hydrogen atom, an alkyl group of 1 to 5 carbon atoms or a halogenated alkyl group of 1 to 5 carbon atoms is preferable, a hydrogen atom, an alkyl group of 1 to carbon atoms or a fluorinated alkyl group of 1 to 5 carbon atoms is more preferable, and in terms of industrial availability, a hydrogen atom or a methyl group is the most desirable.

Examples of the substituent other than a hydroxy group which may be bonded to the benzene ring of hydroxystyrene (which may have the hydrogen atom bonded to the α-position substitutes with a substituent) include a halogen atom, an alkyl group of 1 to 5 carbon atoms, a halogenated alkyl group of 1 to 5 carbon atoms and —COOX$^e$ (X$^e$ represents a hydrogen atom or an organic group). Examples of the halogen atom include a fluorine atom, a chlorine atom, a bromine atom and an iodine atom, and a fluorine atom is particularly desirable.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include benzoic acid in which the hydrogen atom of the carboxy group has been substituted with an organic group and may have the hydrogen atom on the α-position substituted with a substituent; and benzoic acid which has a substituent other than a hydroxy group and a carboxy group bonded to the benzene ring and may have the hydrogen atom on the α-position substituted with a substituent. Here, the α-position (carbon atom on the α-position) refers to the carbon atom having the benzene ring bonded thereto, unless specified otherwise.

As the substituent which substitutes the hydrogen atom on the α-position of benzoic acid, the same substituents as those described above for the substituent on the α-position of the aforementioned α-substituted acrylate ester can be mentioned. Among these, a hydrogen atom, an alkyl group of 1 to 5 carbon atoms or a halogenated alkyl group of 1 to 5 carbon atoms is preferable, a hydrogen atom, an alkyl group of 1 to carbon atoms or a fluorinated alkyl group of 1 to 5 carbon atoms is more preferable, and in terms of industrial availability, a hydrogen atom or a methyl group is the most desirable.

Examples of the substituent other than a hydroxy group and a carboxy group which may be bonded to the benzene ring of benzoic acid (which may have the hydrogen atom bonded to the α-position substituted with a substituent) include a halogen atom, an alkyl group of 1 to 5 carbon atoms and a halogenated alkyl group of 1 to 5 carbon atoms. Examples of the halogen atom include a fluorine atom, a chlorine atom, a bromine atom and an iodine atom, and a fluorine atom is particularly desirable.

As the structural unit (a1), a structural unit derived from an acrylate ester which may have the hydrogen atom bonded to the carbon atom on the α-position substituted with a substituent is preferable.

Specific examples of the structural unit (a1) include a structural unit represented by general formula (a1-0-1) shown below and a structural unit represented by general formula (a1-0-2) shown below.

[Chemical Formula 8]

(a1-0-1)

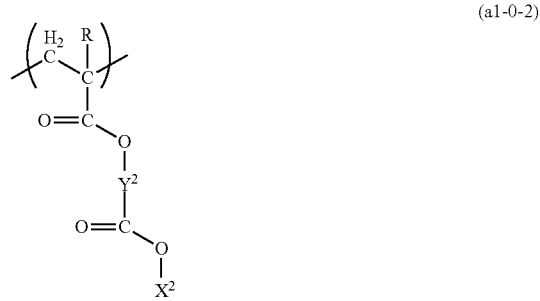

(a1-0-2)

In the formulae, R represents a hydrogen atom, an alkyl group of 1 to 5 carbon atoms or a halogenated alkyl group of 1 to 5 carbon atoms; $X^1$ represents an acid dissociable group; $Y^2$ represents a divalent linking group; and $X^2$ represents an acid dissociable group.

In general formula (a1-0-1), the alkyl group and the halogenated alkyl group for R are respectively the same as defined for the alkyl group and the halogenated alkyl group for the substituent which may be bonded to the carbon atom on the α-position of the aforementioned substituted acrylate ester. R is preferably a hydrogen atom, an alkyl group of 1 to 5 carbon atoms or a fluorinated alkyl group of 1 to 5 carbon atoms, and most preferably a hydrogen atom or a methyl group.

$X^1$ is not particularly limited as long as it is an acid dissociable group. Examples thereof include the aforementioned tertiary alkyl ester-type acid dissociable groups and acetal-type acid dissociable groups, and tertiary alkyl ester-type acid dissociable groups are preferable.

In general formula (a1-0-2), R is the same as defined above.

$X^2$ is the same as defined for $X^1$ in general formula (a1-0-1).

The divalent linking group for $Y^2$ is not particularly limited, and preferable examples thereof include a divalent hydrocarbon group which may have a substituent and a divalent linking group containing a hetero atom.

A hydrocarbon "has a substituent" means that part or all of the hydrogen atoms within the hydrocarbon group is substituted with a substituent (a group or an atom other than hydrogen).

The hydrocarbon group may be either an aliphatic hydrocarbon group or an aromatic hydrocarbon group.

An "aliphatic hydrocarbon group" refers to a hydrocarbon group that has no aromaticity.

The divalent aliphatic hydrocarbon group as the divalent hydrocarbon group for $Y^2$ may be either saturated or unsaturated. In general, the divalent aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and an oxygen atom (═O).

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The alicyclic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (═O).

The aromatic hydrocarbon group is a hydrocarbon group having an aromatic ring.

The aromatic hydrocarbon group as the divalent hydrocarbon group for $Y^2$ preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2, and most preferably 1.

The aromatic hydrocarbon group may or may not have a substituent. For example, the hydrogen atom bonded to the aromatic hydrocarbon ring within the aromatic hydrocarbon group may be substituted with a substituent. Examples of substituents include an alkyl group, an alkoxy group, a halogen atom, a halogenated alkyl group, a hydroxyl group and an oxygen atom (═O).

The alkyl group as the substituent is preferably an alkyl group of 1 to 5 carbon atoms, and a methyl group, an ethyl group, a propyl group, an n-butyl group or a tert-butyl group is particularly desirable.

The alkoxy group as the substituent is preferably an alkoxy group having 1 to carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

With respect to a "divalent linking group containing a hetero atom" for $Y^2$, a hetero atom is an atom other than carbon and hydrogen, and examples thereof include an oxygen atom, a nitrogen atom, a sulfur atom and a halogen atom.

Examples of the divalent linking group containing a hetero atom include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O—, —NH—C(=O)—, =N—, and a group represented by general formula —$Y^{21}$—O—$Y^{22}$—, —[$Y^{21}$—C(=O)—O]$_{m'}$—$Y^{22}$—, —C(=O)—O—$Y^{22}$— or —$Y^{21}$—O—C(=O)—$Y^{22}$— [in the formulae, each of $Y^{21}$ and $Y^{22}$ independently represents a divalent hydrocarbon group which may have a substituent; O represents an oxygen atom; and m' represents an integer of 0 to 3].

When $Y^2$ represents —NH—, H may be substituted with a substituent such as an alkyl group, an acyl group or the like. The substituent (an alkyl group, an aryl group or the like) preferably has 1 to 10 carbon atoms, more preferably 1 to 8, and most preferably 1 to 5.

Each of $Y^{21}$ and $Y^{22}$ independently represents a divalent hydrocarbon group which may have a substituent. As the divalent hydrocarbon group, the same groups as those described above for the "divalent hydrocarbon group which may have a substituent" for $Y^2$ can be mentioned.

As $Y^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As $Y^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m'}$—$Y^{22}$—, m' represents an integer of 0 to 3, preferably an integer of 0 to 2, more preferably 0 or 1, and most preferably 1. Namely, it is particularly desirable that the group represented by the formula —[$Y^{21}$—C(=O)—O]$_{m'}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

As the divalent linking group containing a hetero atom, a linear group containing an oxygen atom as the hetero atom e.g., a group containing an ether bond or an ester bond is preferable, and a group represented by the aforementioned formula —$Y^{21}$—O—$Y^{22}$—, —[$Y^{21}$—C(=O)—O]$_{m'}$—$Y^{22}$— or —$Y^{21}$—O—C(=O)—$Y^{22}$— is more preferable.

Among the aforementioned examples, as the divalent linking group for $Y^2$, an alkylene group, a divalent alicyclic hydrocarbon group or a divalent linking group containing a hetero atom is particularly desirable. Among these, an alkylene group or a divalent linking group containing a hetero atom is more preferable.

Specific examples of the structural unit (a1) include structural units represented by general formulas (a1-1) to (a1-4) shown below.

[Chemical Formula 9]

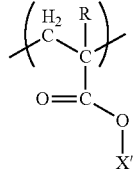

(a1-1)

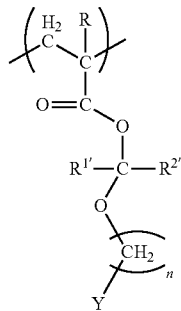

(a1-2)

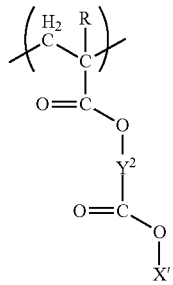

(a1-3)

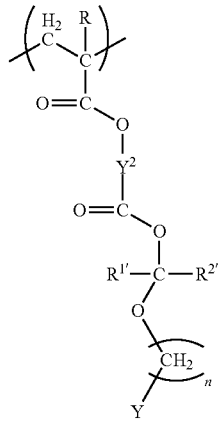

(a1-4)

In the formulas, R, $R^{1\prime}$, $R^{2\prime}$, n, Y and $Y^2$ are the same as defined above; and X' represents a tertiary alkyl ester-type acid dissociable group.

In the formulas, the tertiary alkyl ester-type acid dissociable group for X' include the same tertiary alkyl ester-type acid dissociable groups as those described above.

As $R^{1\prime}$, $R^{2\prime}$, n and Y are respectively the same as defined for $R^{1\prime}$, $R^{2\prime}$, n and Y in general formula (p1) described above in connection with the "acetal-type acid dissociable group".

As examples of $Y^2$, the same groups as those described above for $Y^2$ in general formula (a1-0-2) can be given.

Specific examples of structural units represented by general formula (a1-1) to (a1-4) are shown below.

In the formulae shown below, $R^\alpha$ represents a hydrogen atom, a methyl group or a trifluoromethyl group.

[Chemical Formula 10]

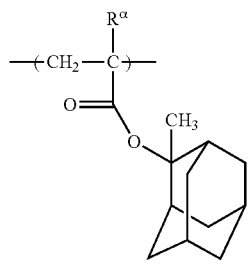
(a1-1-1)

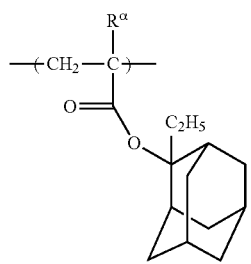
(a1-1-2)

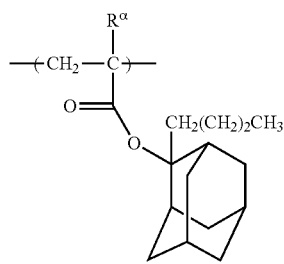
(a1-1-3)

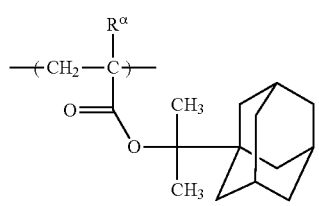
(a1-1-4)

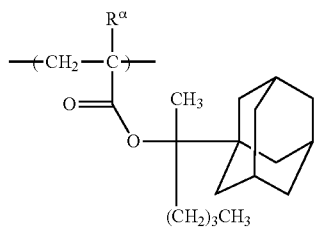
(a1-1-5)

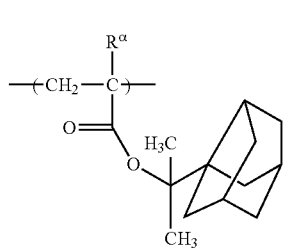
(a1-1-6)

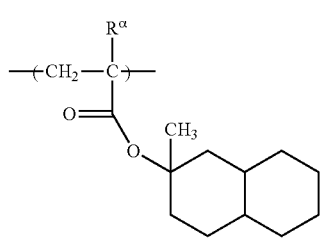
(a1-1-7)

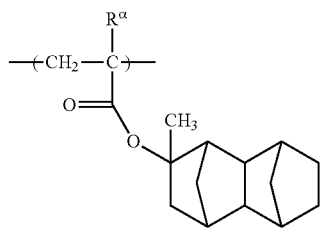
(a1-1-8)

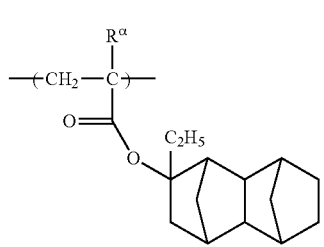
(a1-1-9)

[Chemical Formula 11]

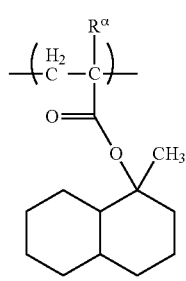
(a1-1-10)

(a1-1-11) 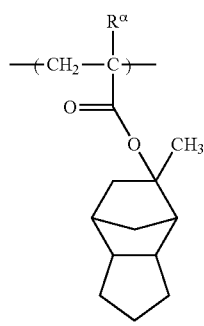
(a1-1-12) 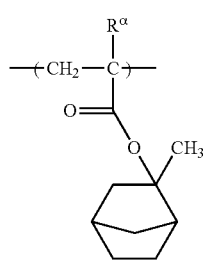
(a1-1-13) 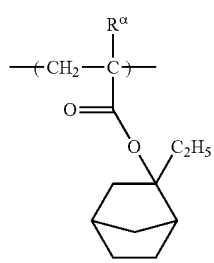
(a1-1-14) 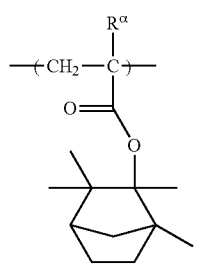
(a1-1-15) 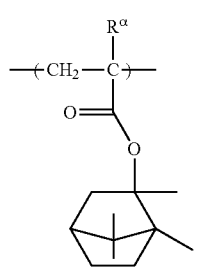
(a1-1-16) 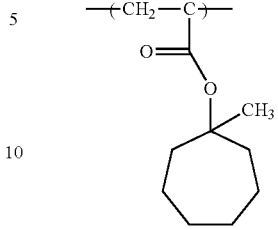
(a1-1-17) 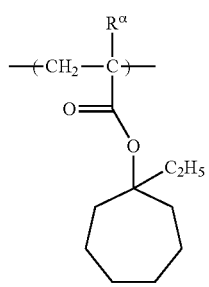
(a1-1-18) 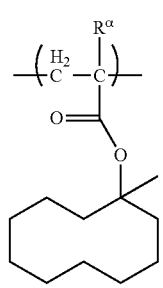
(a1-1-19) 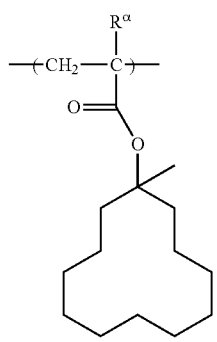
(a1-1-20) 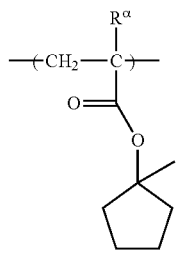

(a1-1-21) 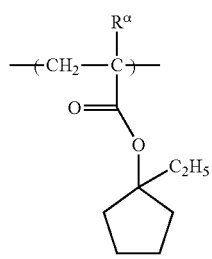
[Chemical Formula 12]
(a1-1-22) 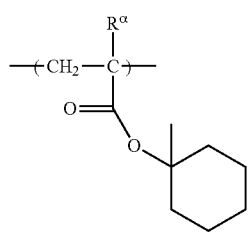
(a1-1-23) 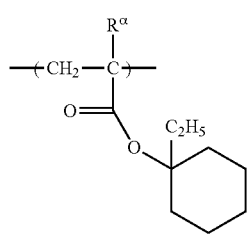
(a1-1-24) 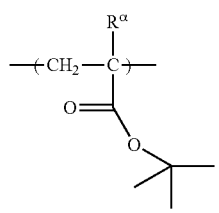
(a1-1-25) 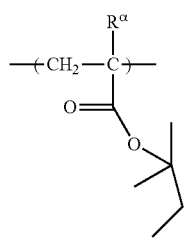
(a1-1-26) 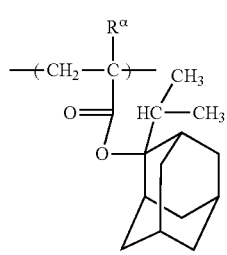
(a1-1-27) 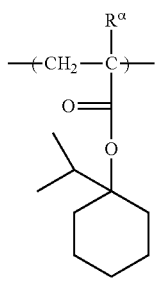
(a1-1-28) 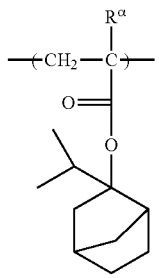
(a1-1-29) 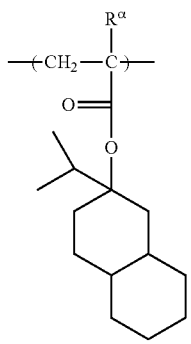
(a1-1-30) 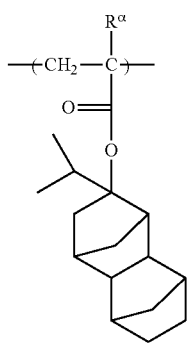
(a1-1-31) 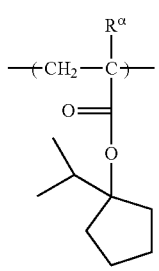

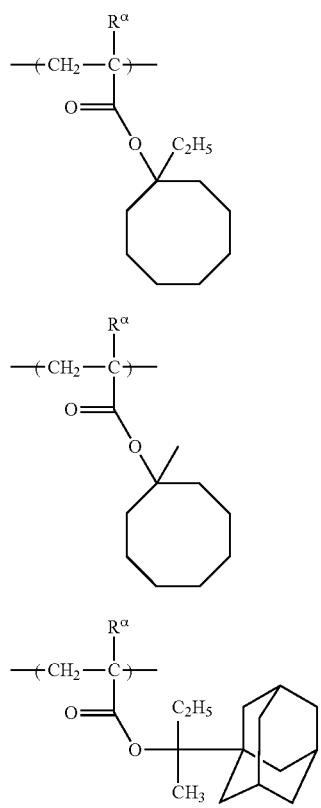
(a1-1-32)
(a1-1-33)
(a1-1-34)
(a1-1-35)
(a1-1-36)
[Chemical Formula 13]
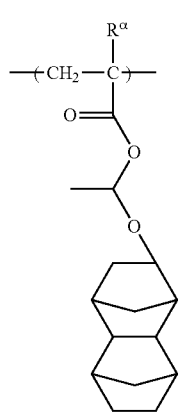
(a1-2-1)
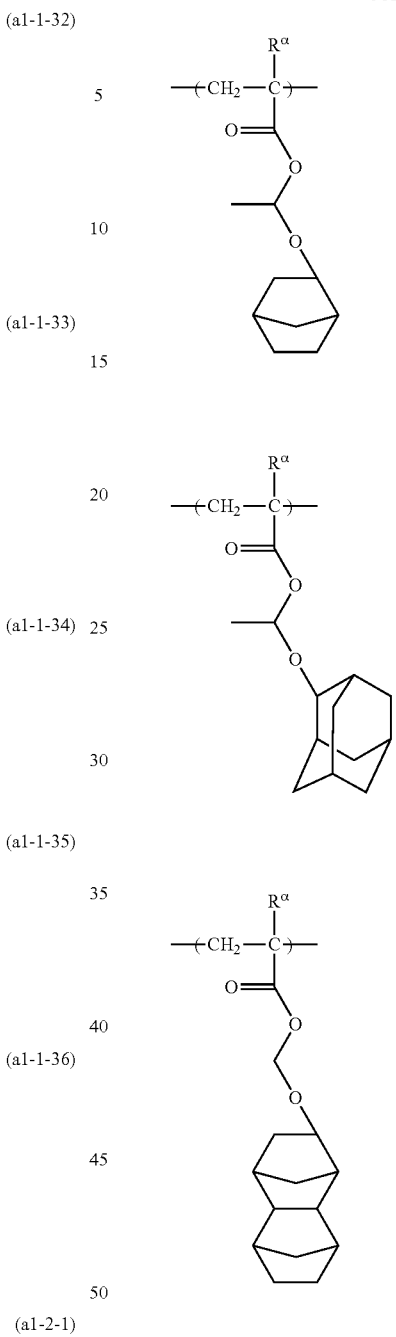
(a1-2-2)
(a1-2-3)
(a1-2-4)
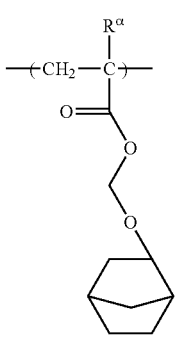
(a1-2-5)

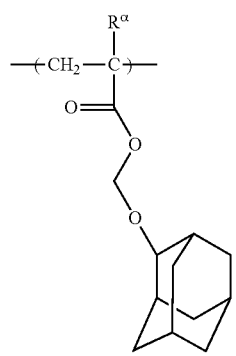 (a1-2-6)
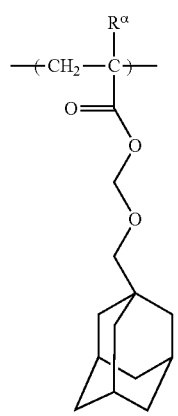 (a1-2-7)
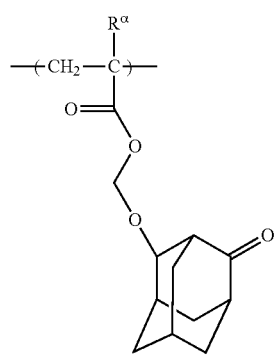 (a1-2-8)
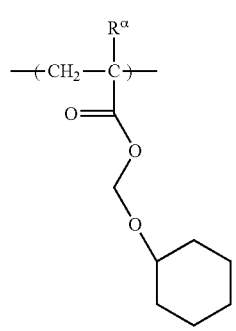 (a1-2-9)
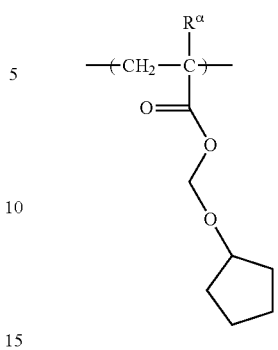 (a1-2-10)
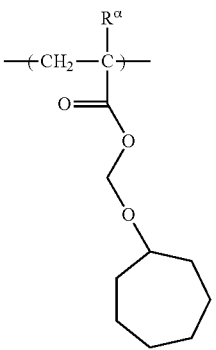 (a1-2-11)
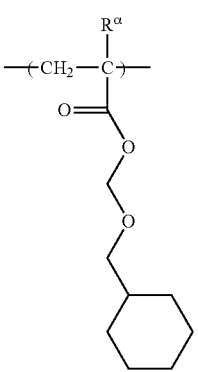 (a1-2-12)
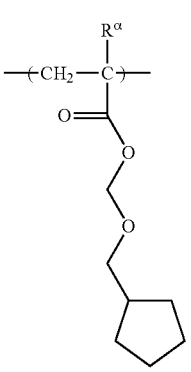 (a1-2-13)

(a1-2-14) 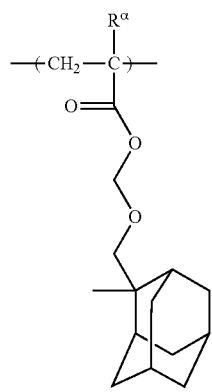
(a1-2-15) 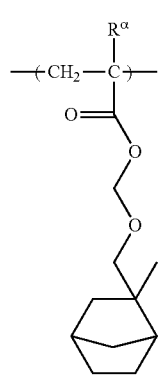
(a1-2-16) 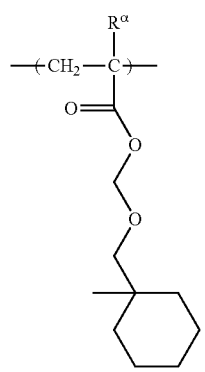
(a1-2-17) 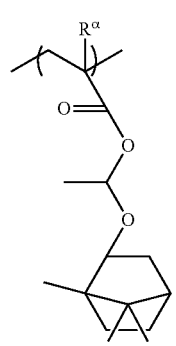
(a1-2-18) 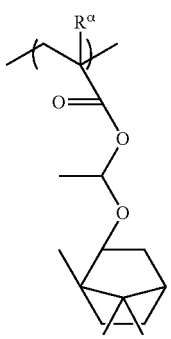
(a1-2-19)
(a1-2-20)
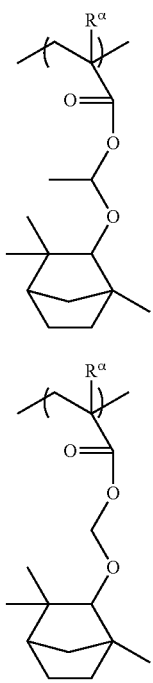
(a1-2-21)
(a1-2-22) 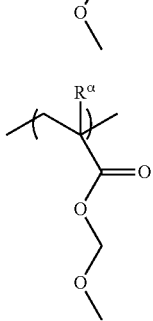

-continued
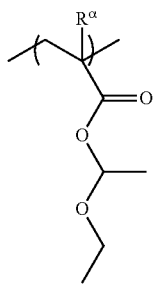
(a1-2-23)
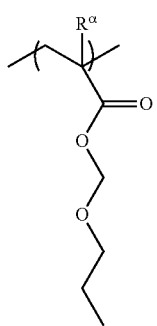
(a1-2-24)
[Chemical Formula 14]
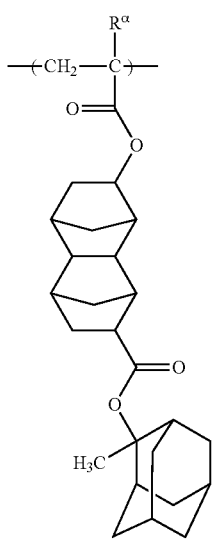
(a1-3-1)
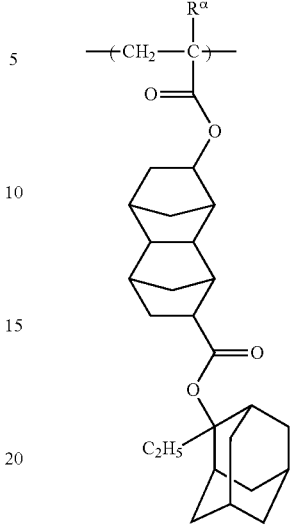
(a1-3-2)
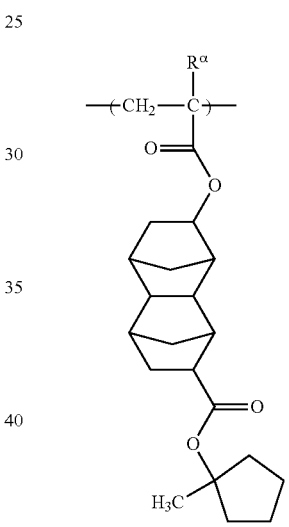
(a1-3-3)
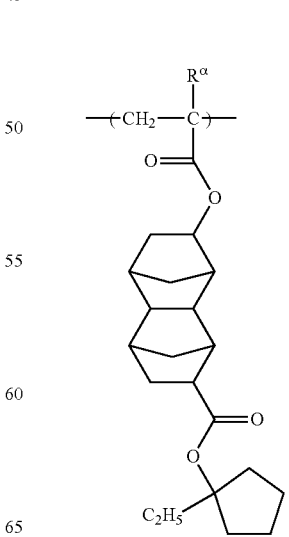
(a1-3-4)

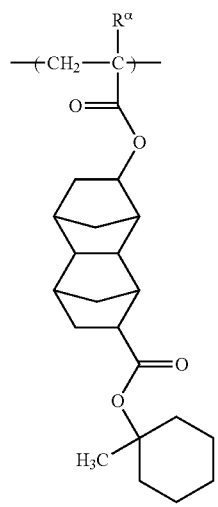
(a1-3-5)
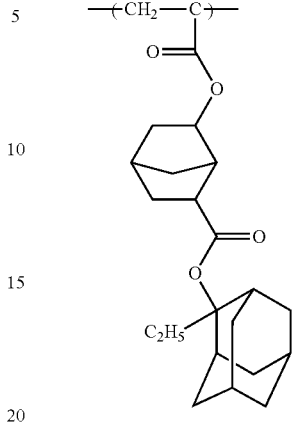
(a1-3-8)
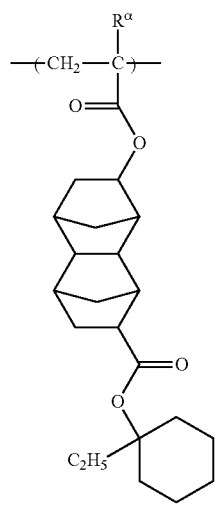
(a1-3-6)
(a1-3-9)
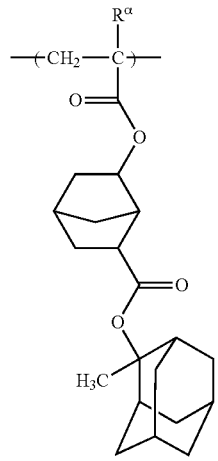
(a1-3-7)
(a1-3-10)

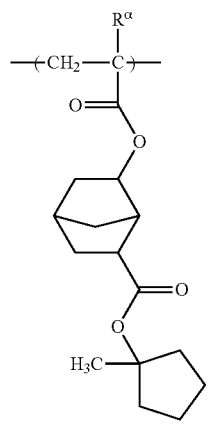 (a1-3-11)
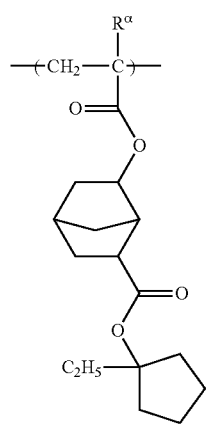 (a1-3-12)
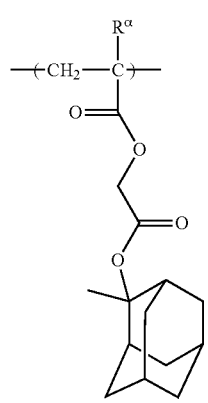 (a1-3-13)
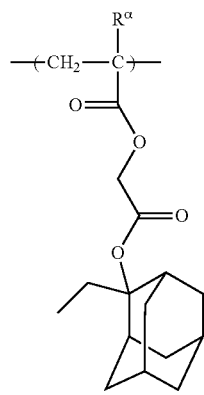 (a1-3-14)
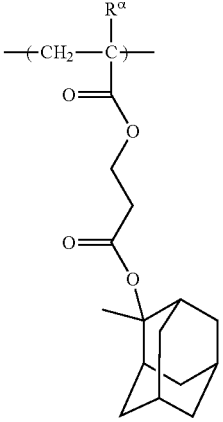 (a1-3-15)
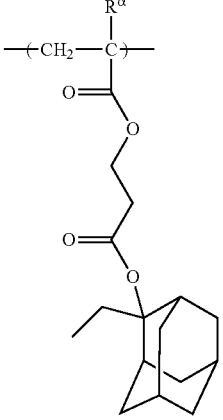 (a1-3-16)
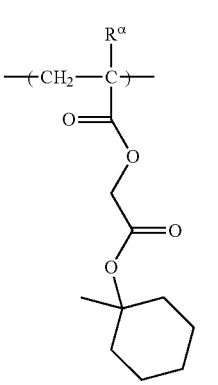 (a1-3-17)
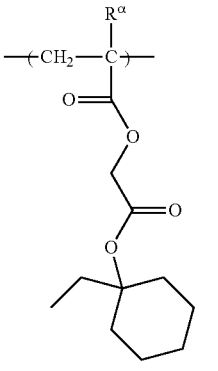 (a1-3-18)

[Chemical Formula 15]
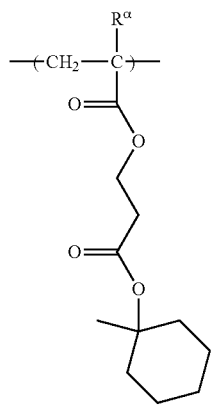
(a1-3-19)
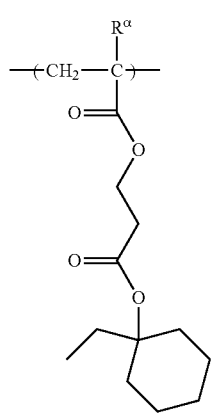
(a1-3-20)
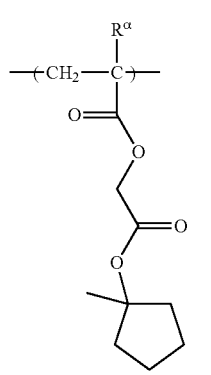
(a1-3-21)
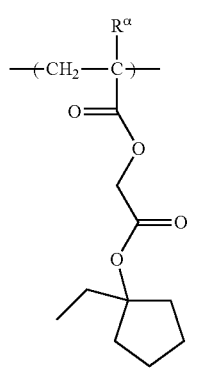
(a1-3-22)
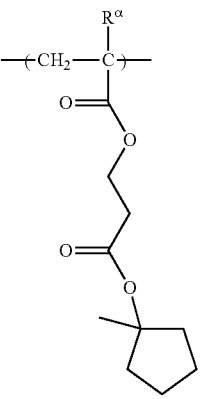
(a1-3-23)
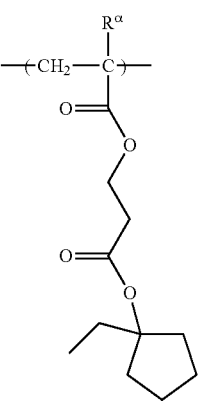
(a1-3-24)
[Chemical Formula 16]
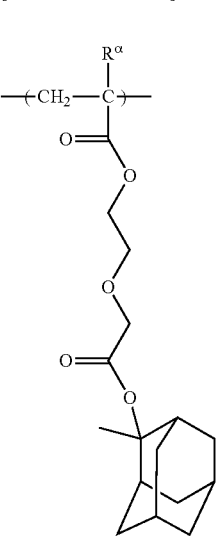
(a1-3-25)

(a1-3-26) 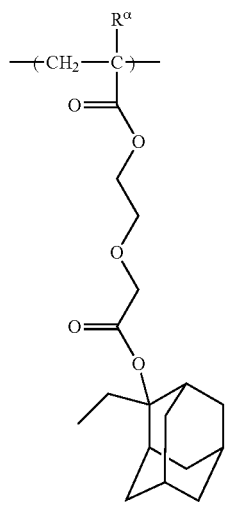
(a1-3-29) 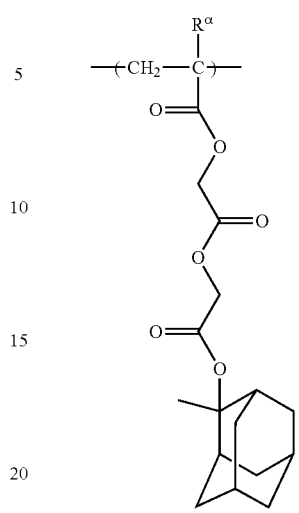
(a1-3-27) 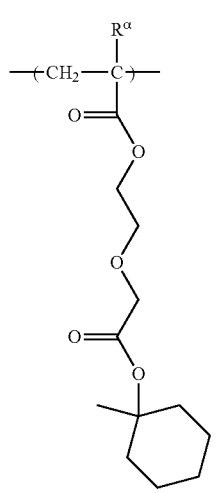
(a1-3-30) 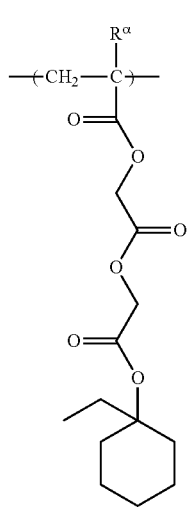
(a1-3-28) 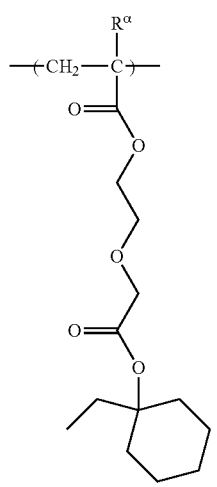
(a1-3-31) 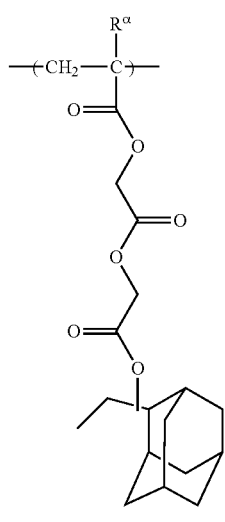

(a1-3-32)
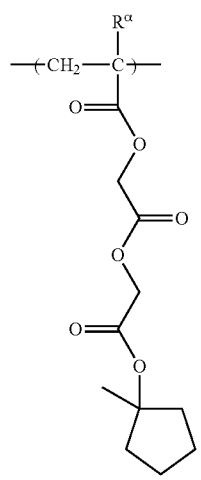
[Chemical Formula 17]
(a1-4-1)
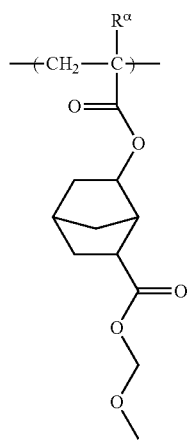
(a1-4-2)
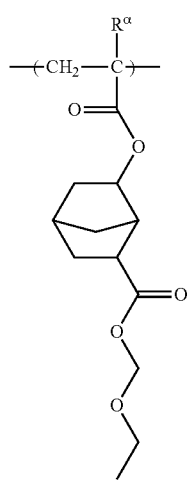
(a1-4-3)
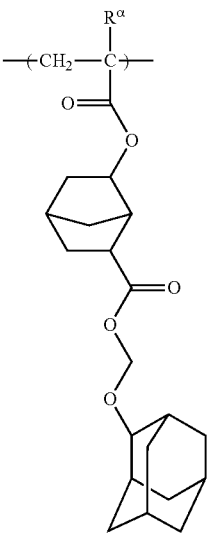
(a1-4-4)
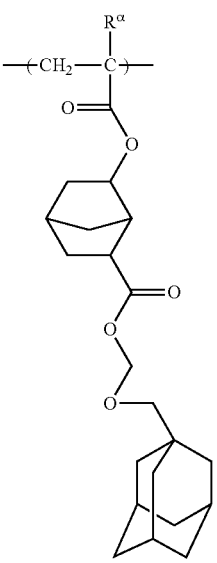
(a1-4-5)
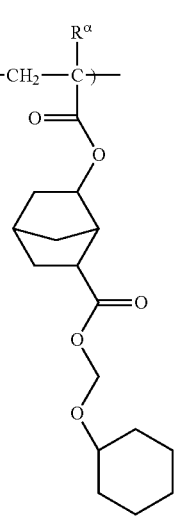

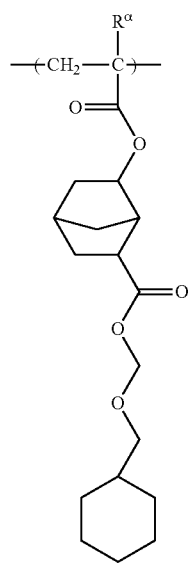
(a1-4-6)
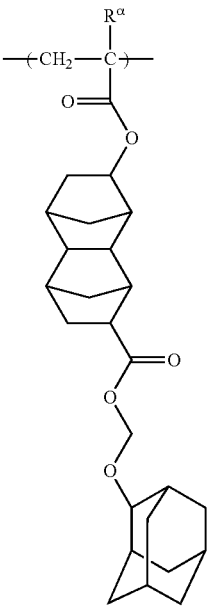
(a1-4-9)
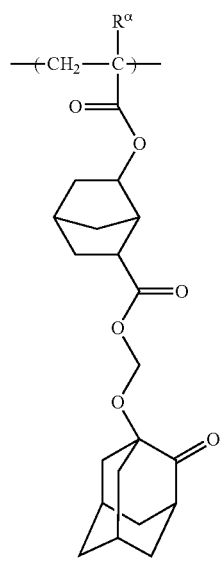
(a1-4-7)
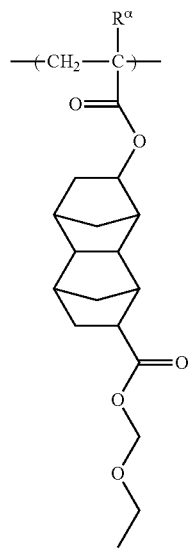
(a1-4-8)
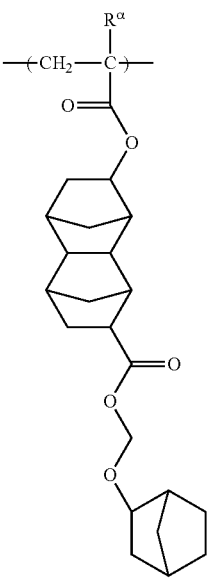
(a1-4-10)

(a1-4-11)
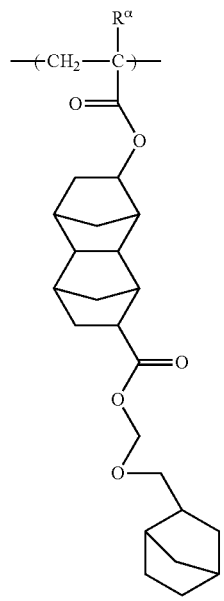
(a1-4-12)
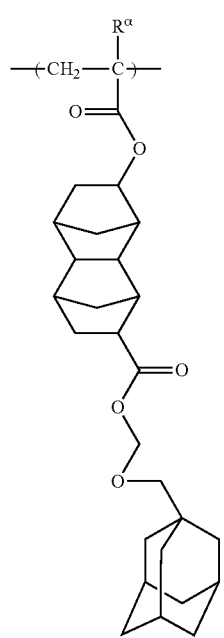
(a1-4-13)
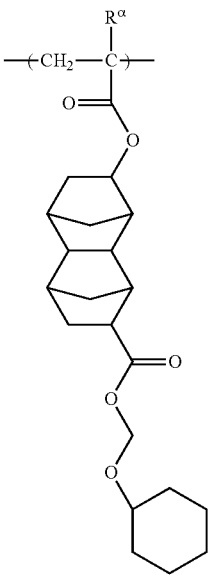
(a1-4-14)
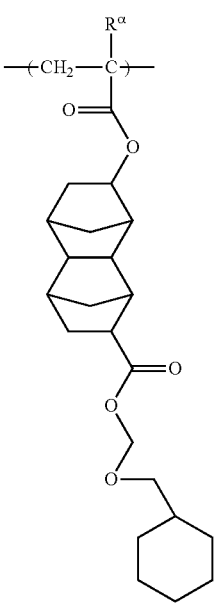

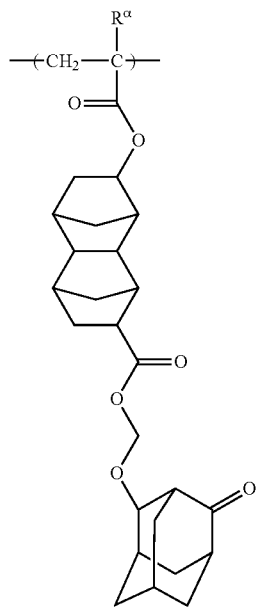

(a1-4-15)

In the present invention, as the structural unit (a1), it is preferable to include at least one structural unit selected from the group consisting of a structural unit represented by general formula (a1-0-11) shown below, a structural unit represented by general formula (a1-0-12) shown below, a structural unit represented by general formula (a1-0-13) shown below, a structural unit represented by general formula (a1-0-14) shown below, a structural unit represented by general formula (a1-0-15) shown below and a structural unit represented by general formula (a1-0-2) shown below.

Among these examples, as the structural unit (a1), it is preferable to include at least one structural unit selected from the group consisting of a structural unit represented by general formula (a1-0-11) shown below, a structural unit represented by general formula (a1-0-12) shown below, a structural unit represented by general formula (a1-0-13) shown below, a structural unit represented by general formula (a1-0-14) shown below and a structural unit represented by general formula (a1-0-15) shown below.

[Chemical Formula 18]

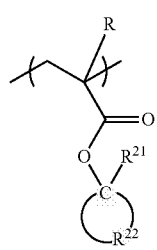

(a1-0-11)

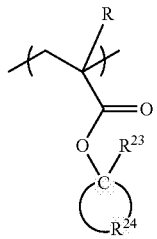

(a1-0-12)

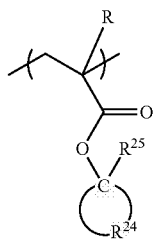

(a1-0-13)

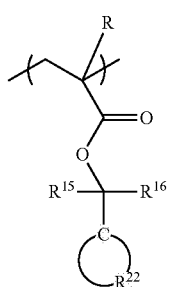

(a1-0-14)

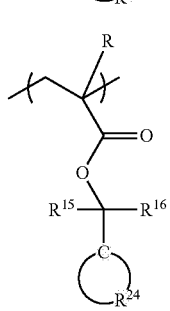

(a1-0-15)

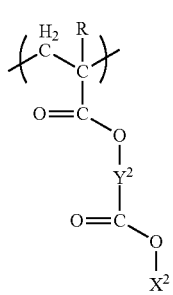

(a1-0-2)

In the formulas, R represents a hydrogen atom, an alkyl group of 1 to 5 carbon atoms or a halogenated alkyl group of 1 to 5 carbon atoms; $R^{21}$ represents an alkyl group; $R^{22}$ represents a group which forms an aliphatic monocyclic group with the carbon atom to which $R^{22}$ is bonded; $R^{23}$ represents a branched alkyl group; $R^{24}$ represents a group which forms an aliphatic polycyclic group with the carbon atom to which $R^{24}$ is bonded; $R^{25}$ represents a linear alkyl group of 1 to 5 carbon atoms; $R^{15}$ and $R^{16}$ each independently represents an alkyl group; $Y^2$ represents a divalent linking group; and $X^2$ an acid dissociable group.

In the formulas, R, $Y^2$ and $X^2$ are the same as defined above.

In general formula (a1-0-11), as the alkyl group for $R^{21}$, the same alkyl groups as those described above for $R^{14}$ in formulas (1-1) to (1-9) can be used, preferably a methyl group, an ethyl group or an isopropyl group.

As the aliphatic monocyclic group formed by $R^{22}$ and the carbon atoms to which $R^{22}$ is bonded, the same aliphatic cyclic groups as those described above for the aforementioned tertiary alkyl ester-type acid dissociable group and which are monocyclic can be used. Specific examples include groups in which one or more hydrogen atoms have been removed from a monocycloalkane. The monocycloalkane is preferably a 3- to 11-membered ring, more preferably a 3- to 8-membered ring, still more preferably a 4- to 6-membered ring, and most preferably a 5- or 6-membered ring.

The monocycloalkane may or may not have part of the carbon atoms constituting the ring replaced with an ether bond (—O—).

Further, the monocycloalkane may have a substituent such as an alkyl group of 1 to 5 carbon atoms, a fluorine atom or a fluorinated alkyl group of 1 to 5 carbon atoms.

As an examples of $R^{22}$ constituting such an aliphatic cyclic group, an alkylene group which may have an ether bond (—O—) interposed between the carbon atoms can be given.

Specific examples of structural units represented by general formula (a1-0-11) include structural units represented by the aforementioned formulas (a1-0-16) to (a1-1-23), (a1-1-27) and (a1-1-31). Among these, a structural unit represented by general formula (a1-0-02) shown below which includes the structural units represented by the aforementioned formulas (a1-0-16), (a1-1-17), (a1-1-20) to (a1-1-23), (a1-1-27), (a1-1-31), (a1-1-32) and (a1-1-33) is preferable. Further, a structural unit represented by general formula (a1-0-02') shown below is also preferable.

In the formulas, h represents an integer of 1 to 4, and preferably 1 or 2.

[Chemical Formula 19]

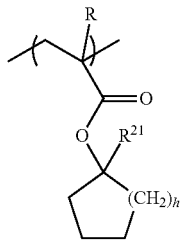

(a1-1-02)

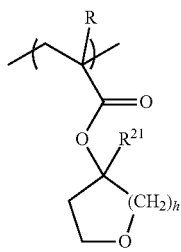

(a1-1-02')

In the formulae, R and $R^{21}$ are the same as defined above; and h represents an integer of 1 to 4.

In general formula (a1-0-12), as the branched alkyl group for $R^{23}$, the same alkyl groups as those described above for $R^{14}$ which are branched can be used, and an isopropyl group is particularly desirable.

As the aliphatic polycyclic group formed by $R^{24}$ and the carbon atoms to which $R^{24}$ is bonded, the same aliphatic cyclic groups as those described above for the aforementioned tertiary alkyl ester-type acid dissociable group and which are polycyclic can be used.

Specific examples of structural units represented by general formula (a1-0-12) include structural units represented by the aforementioned formulas (a1-0-26) and (a1-1-28) to (a1-1-30).

As the structural unit (a0-0-12), a structural unit in which the aliphatic polycyclic group formed by $R^{24}$ and the carbon atom to which $R^{24}$ is bonded is a 2-adamantyl group is preferable, and a structural unit represented by the aforementioned formula (a1-0-26) is particularly desirable.

In general formula (a1-0-13), R and $R^{24}$ are the same as defined above.

As the linear alkyl group for $R^{25}$, the same linear alkyl groups as those described above for $R^{14}$ in the aforementioned formulas (1-1) to (1-9) can be mentioned, and a methyl group or an ethyl group is particularly desirable.

Specific examples of structural units represented by general formula (a1-0-13) include structural units represented by the aforementioned formulas (a1-0-1), (a1-1-2) and (a1-1-7) to (a1-1-1-15) which were described above as specific examples of the structural unit represented by general formula (a1-1).

As the structural unit (a1-0-13), a structural unit in which the aliphatic polycyclic group formed by $R^{24}$ and the carbon atom to which $R^{24}$ is bonded is a 2-adamantyl group is preferable, and a structural unit represented by the aforementioned formula (a1-0-1) or (a1-1-2) is particularly desirable.

In general formula (a1-0-14), R and $R^{22}$ are the same as defined above. $R^{15}$ and $R^{16}$ are the same as $R^{15}$ and $R^{16}$ in the aforementioned general formulae (2-1) to (2-6), respectively.

Specific examples of structural units represented by general formula (a1-0-14) include structural units represented by the aforementioned formulae (a1-0-35) and (a1-1-36) which were described above as specific examples of the structural unit represented by general formula (a1-1).

In general formula (a1-0-15), R and $R^{24}$ are the same as defined above. $R^{15}$ and $R^{16}$ are the same as $R^{15}$ and $R^{16}$ in the aforementioned general formulae (2-1) to (2-6), respectively.

Specific examples of structural units represented by general formula (a1-0-15) include structural units represented by the aforementioned formulae (a1-0-4) to (a1-1-6) and (a1-1-34) which were described above as specific examples of the structural unit represented by general formula (a1-1).

Examples of structural units represented by general formula (a1-0-2) include structural units represented by the aforementioned formulas (a1-3) and (a1-4).

As a structural unit represented by general formula (a1-0-2), those in which $Y^2$ is a group represented by the aforementioned formula —$Y^{21}$—O—$Y^{22}$— or —$Y^{21}$—C(=O)—O—$Y^{22}$— is particularly desirable.

Preferable examples of such structural units include a structural unit represented by general formula (a1-0-01) shown below, a structural unit represented by general formula (a1-0-02) shown below, and a structural unit represented by general formula (a1-0-03) shown below.

[Chemical Formula 20]

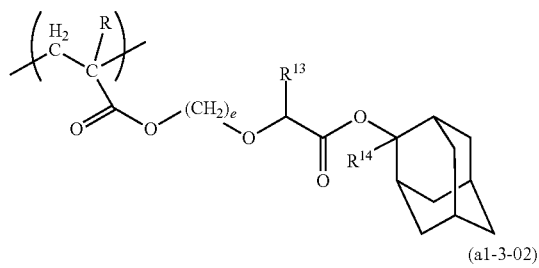

(a1-3-01)

(a1-3-02)

In the formulas, R is the same as defined above; $R^{13}$ represents a hydrogen atom or a methyl group; $R^{14}$ represents an alkyl group; e represents an integer of 1 to 10; and n' represents an integer of 0 to 3.

[Chemical Formula 21]

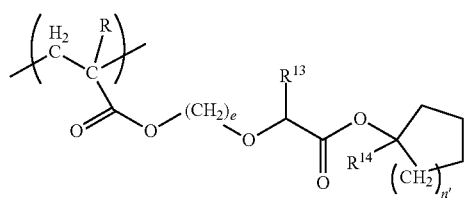

(a1-3-03)

In the formula, R is as defined above; each of $Y^{2\prime}$ and $Y^{2\prime\prime}$ independently represents a divalent linking group; X' represents an acid dissociable group; and w represents an integer of 0 to 3.

In general formulas (a1-0-01) and (a1-3-02), $R^{13}$ is preferably a hydrogen atom.

$R^{14}$ is the same as defined for $R^{14}$ in the aforementioned formulas (1-1) to (1-9).

e is preferably an integer of 1 to 8, more preferably an integer of 1 to 5, and most preferably 1 or 2.

n' is preferably 1 or 2, and most preferably 2.

Specific examples of structural units represented by general formula (a1-0-01) include structural units represented by the aforementioned formulas (a1-0-25) and (a1-3-26).

Specific examples of structural units represented by general formula (a1-0-02) include structural units represented by the aforementioned formulas (a1-0-27) and (a1-3-28).

In general formula (a1-0-03), as the divalent linking group for $Y^{2\prime}$ and $Y^{2\prime\prime}$, the same groups as those described above for $Y^2$ in general formula (a1-0-2) can be used.

As $Y^{2\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2\prime\prime}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable group for X', the same groups as those described above can be used. X' is preferably a tertiary alkyl ester-type acid dissociable group, more preferably the aforementioned group (i) in which a substituent is bonded to the carbon atom to which an atom adjacent to the acid dissociable group is bonded to on the ring skeleton to form a tertiary carbon atom. Among these, a group represented by the aforementioned general formula (1-1) is particularly desirable.

w represents an integer of 0 to 3, preferably an integer of 0 to 2, more preferably 0 or 1, and most preferably 1.

As the structural unit represented by general formula (a1-0-03), a structural unit represented by general formula (a1-0-03-1) or (a1-3-03-2) shown below is preferable, and a structural unit represented by general formula (a1-0-03-1) is particularly desirable.

[Chemical Formula 22]

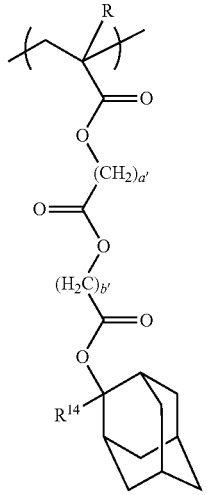

(a1-3-03-1)

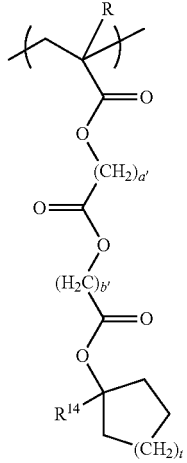

(a1-3-03-2)

In the formulas, R and $R^{14}$ are the same as defined above; a' represents an integer of 1 to 10; b' represents an integer of 1 to 10; and t represents an integer of 0 to 3.

In general formulas (a1-0-03-1) and (a1-3-03-2), a' is the same as defined above, preferably an integer of 1 to 8, more preferably 1 to 5, and most preferably 1 or 2.

b' is the same as defined above, preferably an integer of 1 to 8, more preferably 1 to 5, and most preferably 1 or 2.

t is preferably an integer of 1 to 3, and most preferably 1 or 2.

Specific examples of structural units represented by general formula (a1-0-03-1) or (a1-3-03-2) include structural units represented by the aforementioned formulas (a1-0-29) to (a1-3-32).

As the structural unit (a1) contained in the component (A1), 1 type of structural unit may be used, or 2 or more types may be used.

In the component (A1), the amount of the structural unit (a1) based on the combined total of all structural units constituting the component (A1) is preferably 15 to 70 mol %, more preferably 15 to 60 mol %, and still more preferably 20 to 55 mol %.

When the amount of the structural unit (a1) is at least as large as the lower limit of the above-mentioned range, a pattern can be easily formed using a resist composition prepared from the component (A1), and various lithography properties such as sensitivity, resolution, LWR and the like are improved. On the other hand, when the amount of the structural unit (a1) is no more than the upper limit of the above-mentioned range, a good balance can be reliably achieved with the other structural units.

[Structural Unit (a0)]

The structural unit (a0) is a structural unit containing an —$SO_2$— containing cyclic group.

By virtue of the structural unit (a0) containing a —$SO_2$— containing cyclic group, a resist composition containing the component (A1) including the structural unit (a0) is capable of improving the adhesion of a resist film to a substrate. Further, the —$SO_2$— containing cyclic group contributes to improvement in various lithography properties such as sensitivity, resolution, exposure latitude (EL margin), line width roughness (LWR), line edge roughness (LER) and mask reproducibility.

Here, an "—$SO_2$— containing cyclic group" refers to a cyclic group having a ring containing —$SO_2$— within the ring structure thereof, i.e., a cyclic group in which the sulfur atom (S) within —$SO_2$— forms part of the ring skeleton of the cyclic group.

In the —$SO_2$— containing cyclic group, the ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings.

The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

The —$SO_2$— containing cyclic group preferably has 3 to 30 carbon atoms, more preferably 4 to 20, still more preferably 4 to 15, and most preferably 4 to 12. Herein, the number of carbon atoms refers to the number of carbon atoms constituting the ring skeleton, excluding the number of carbon atoms within a substituent.

The —$SO_2$— containing cyclic group may be either a —$SO_2$— containing aliphatic cyclic group or a —$SO_2$— containing aromatic cyclic group. A —$SO_2$— containing aliphatic cyclic group is preferable.

Examples of the —$SO_2$— containing aliphatic cyclic group include aliphatic cyclic groups in which part of the carbon atoms constituting the ring skeleton has been substituted with a —$SO_2$— group or a —O—$SO_2$— group and has at least one hydrogen atom removed from the aliphatic hydrocarbon ring. Specific examples include an aliphatic hydrocarbon ring in which a —$CH_2$— group constituting the ring skeleton thereof has been substituted with a —$SO_2$— group and has at least one hydrogen atom removed therefrom; and an aliphatic hydrocarbon ring in which a —$CH_2$—$CH_2$— group constituting the ring skeleton has been substituted with a —O—$SO_2$— group and has at least one hydrogen atom removed therefrom.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The —$SO_2$— containing cyclic group may have a substituent. Examples of the substituent include an alkyl group, an alkoxy group, a halogen atom, a halogenated alkyl group, a hydroxy group, an oxygen atom (=O), —COOR", —OC(=O)R", a hydroxyalkyl group and a cyano group (wherein R" represents a hydrogen atom or an alkyl group).

The alkyl group for the substituent is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear or branched alkoxy group. Specific examples of the alkoxy group include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(=O)R" group, R" preferably represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxy group.

More specific examples of the —$SO_2$— containing cyclic group include groups represented by general formulas (3-1) to (3-4) shown below.

[Chemical Formula 23]

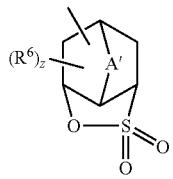
(3-1)

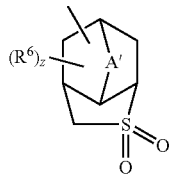
(3-2)

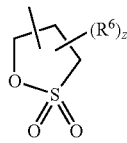
(3-3)

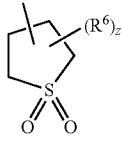
(3-4)

In the formulas, A' represents an oxygen atom, a sulfur atom or an alkylene group of 1 to 5 carbon atoms which may contain an oxygen atom or a sulfur atom; z represents an integer of 0 to 2; and $R^6$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group.

In general formulas (3-1) to (3-4) above, A' represents an oxygen atom (—O—), a sulfur atom (—S—) or an alkylene group of 1 to 5 carbon atoms which may contain an oxygen atom or a sulfur atom.

As the alkylene group of 1 to 5 carbon atoms represented by A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—$CH_2$—, —$CH_2$—O—$CH_2$—, —S—$CH_2$—, —$CH_2$—S—$CH_2$—.

As A', an alkylene group of 1 to 5 carbon atoms or —O— is preferable, more preferably an alkylene group of 1 to 5 carbon atoms, and most preferably a methylene group.

z represents an integer of 0 to 2, and is most preferably 0.

When z is 2, the plurality of $R^6$ may be the same or different from each other.

As the alkyl group, alkoxy group, halogenated alkyl group, —COOR", —OC(=O)R" and hydroxyalkyl group for $R^6$, the same alkyl groups, alkoxy groups, halogenated alkyl groups, —COOR", —OC(=O)R" and hydroxyalkyl groups as those described above as the substituent for the —$SO_2$— containing cyclic group can be mentioned.

Specific examples of the cyclic groups represented by general formulas (3-1) to (3-4) are shown below. In the formulas shown below, "Ac" represents an acetyl group.

[Chemical Formula 24]

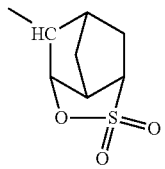
(3-1-1)

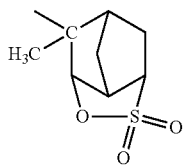
(3-1-2)

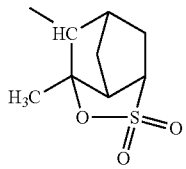
(3-1-3)

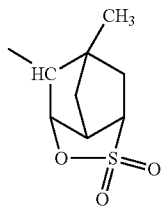
(3-1-4)

-continued
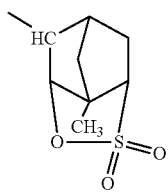
(3-1-5)
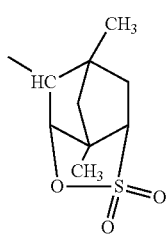
(3-1-6)
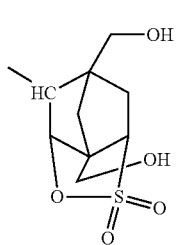
(3-1-7)
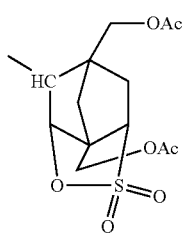
(3-1-8)
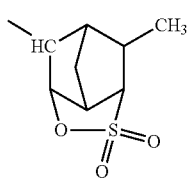
(3-1-9)
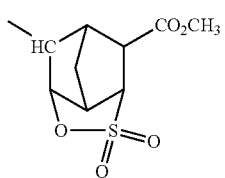
(3-1-10)
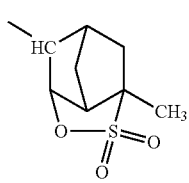
(3-1-11)
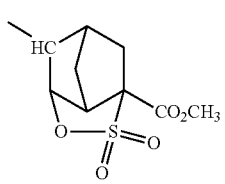
(3-1-12)
-continued
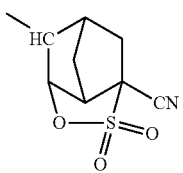
(3-1-13)
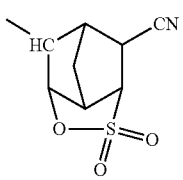
(3-1-14)
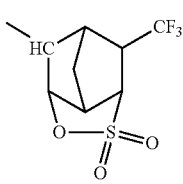
(3-1-15)
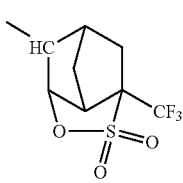
(3-1-16)
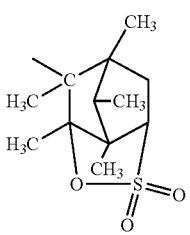
(3-1-17)
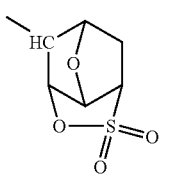
(3-1-18)
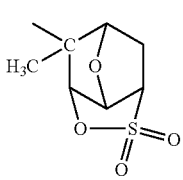
(3-1-19)
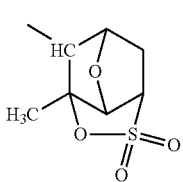
(3-1-20)

-continued
(3-1-21)
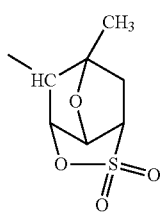
[Chemical Formula 25]
(3-1-22)
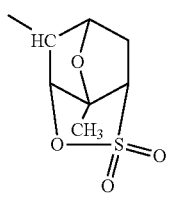
(3-1-23)
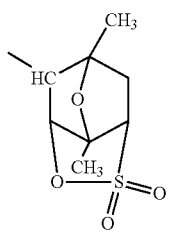
(3-1-24)
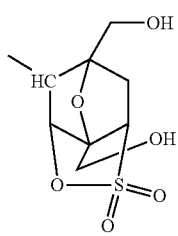
(3-1-25)
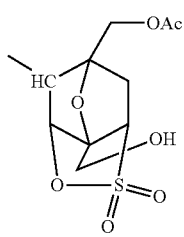
(3-1-26)
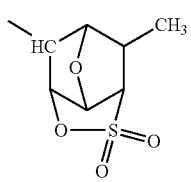
(3-1-27)
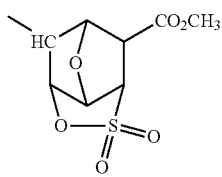
(3-1-28)
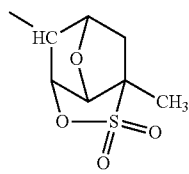
(3-1-29)
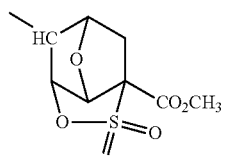
(3-1-30)
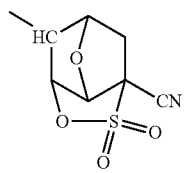
(3-1-31)
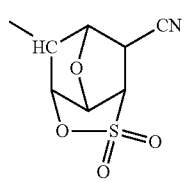
(3-1-32)
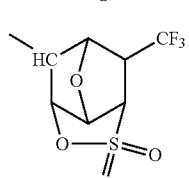
(3-1-33)
[Chemical Formula 26]
(3-2-1)
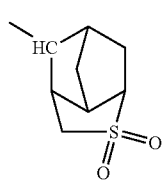
(3-2-2)
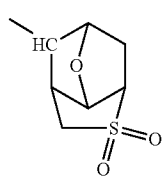
(3-3-1)

-continued

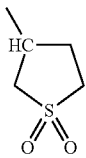
(3-4-1)

As the —SO$_2$— containing cyclic group, a group represented by the aforementioned general formula (3-1) is preferable, at least one member selected from the group consisting of groups represented by the aforementioned chemical formulas (3-1-1), (3-1-18), (3-3-1) and (3-4-1) is more preferable, and a group represented by chemical formula (a1-0-1) is most preferable.

As the structural unit (a0), there is no particular limitation as long as it is a structural unit having an —SO$_2$— containing cyclic group, and an arbitrary structural unit may be used.

The structural unit (a0) is preferably a structural unit derived from an acrylate ester which may have the hydrogen atom bonded to the carbon atom on the α-position substituted with a substituent and contains an —SO$_2$— containing cyclic group.

More specifically, examples of the structural unit (a0) include structural units represented by general formula (a0-0) shown below.

[Chemical Formula 27]

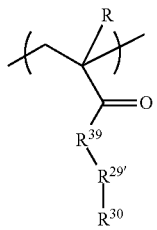
(a0-0)

In the formula, R represents a hydrogen atom, an alkyl group of 1 to 5 carbon atoms or a halogenated alkyl group of 1 to 5 carbon atoms; $R^{39}$ represents —O— or —NH—; $R^{30}$ represents a —SO$_2$— containing cyclic group; and $R^{29'}$ represents a single bond or a divalent linking group.

In formula (a0-0), R is the same as defined above.
In the formula (a0-0), $R^{39}$ represents —O— or —NH—.
In formula (a0-0), $R^{30}$ is the same as defined for the aforementioned —SO$_2$— containing group.

In the formula (a0-0), $R^{29'}$ may be either a single bond or a divalent linking group. In terms of the effects of the present invention, a divalent linking group is preferable.

As the divalent linking group for $R^{29}$, for example, the same divalent linking groups as those described for $Y^2$ in general formula (a1-0-2) explained above in relation to the structural unit (a1) can be mentioned. Among these, an alkylene group, a divalent alicyclic hydrocarbon group or a divalent linking group containing a hetero atom is preferable, and an alkylene group or a divalent linking group containing an ester bond (—C(=O)—O—) is preferable.

As the alkylene group, a linear or branched alkylene group is preferable. Specific examples include the same linear alkylene groups and branched alkylene groups as those described above for the aliphatic hydrocarbon group represented by $Y^2$.

As the divalent linking group containing an ester bond, a group represented by general formula: —R$^{20}$—C(=O)—O— (in the formula, R$^{20}$ represents a divalent linking group) is particularly desirable. Namely, the structural unit (a0) is preferably a structural unit represented by general formula (a0-0-1) shown below.

[Chemical Formula 28]

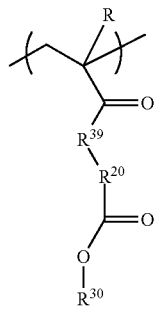
(a0-0-1)

In the formula, R represents a hydrogen atom, an alkyl group of 1 to 5 carbon atoms or a halogenated alkyl group of 1 to 5 carbon atoms; $R^{39}$ represents —O— or —NH—; $R^{20}$ represents a divalent linking group; and $R^{30}$ represents an —SO$_2$— containing cyclic group.

$R^{20}$ is not particularly limited. For example, the same divalent linking groups as those described for $R^{29'}$ in general formula (a0-0) can be mentioned.

As the divalent linking group for $R^{20}$, an alkylene group, a divalent alicyclic hydrocarbon group or a divalent linking group containing a hetero atom is preferable.

As the linear or branched alkylene group, the divalent alicyclic hydrocarbon group and the divalent linking group containing a hetero atom, the same linear or branched alkylene group, divalent alicyclic hydrocarbon group and divalent linking group containing a hetero atom as those described above as preferable examples of $R^{29'}$ can be mentioned.

Among these, a linear or branched alkylene group, or a divalent linking group containing an oxygen atom as a hetero atom is more preferable.

As the linear alkylene group, a methylene group or an ethylene group is preferable, and a methylene group is particularly desirable.

As the branched alkylene group, an alkylmethylene group or an alkylethylene group is preferable, and —CH(CH$_3$)—, —C(CH$_3$)$_2$— or —C(CH$_3$)$_2$CH$_2$— is particularly desirable.

As the divalent linking group containing a hetero atom, a divalent linking group containing an ether bond or an ester bond is preferable, and a group represented by the aforementioned formula —Y$^{21}$—O—Y$^{22}$—, —[Y$^{21}$—C(=O)—O]$_{m'}$—Y$^{22}$— or —Y$^{21}$—O—C(=O)—Y$^{22}$— is more preferable. $Y^{21}$, $Y^{22}$ and m' are the same as defined above.

Among these, a group represented by the formula —Y$^{21}$—O—C(=O)—Y$^{22}$—, and a group represented by the formula —(CH$_2$)$_c$—O—C(=O)—(CH$_2$)$_d$— is particularly desirable. c represents an integer of 1 to 5, preferably an integer of 1 to 3, and more preferably 1 or 2. d represents an integer of 1 to 5, preferably an integer of 1 to 3, and more preferably 1 or 2.

In particular, as the structural unit (a0), a structural unit represented by general formula (a1-0-11) or (a0-0-12) shown below is preferable, and a structural unit represented by general formula (a0-0-12) is more preferable.

[Chemical Formula 29]

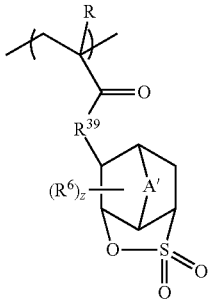
(a0-0-11)

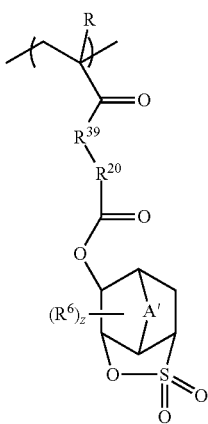
(a0-0-12)

In the formulae, R, A', $R^6$, z, $R^{39}$ and $R^{20}$ are the same as defined above.

In general formula (a0-0-11), A' is preferably a methylene group, an ethylene group, an oxygen atom (—O—) or a sulfur atom (—S—).

As the structural unit represented by general formula (a0-0-12), a structural unit represented by general formula (a0-0-12a) or (a0-0-12b) shown below is particularly desirable.

[Chemical Formula 30]

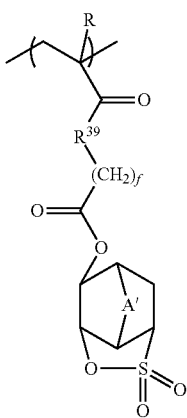
(a0-0-12a)

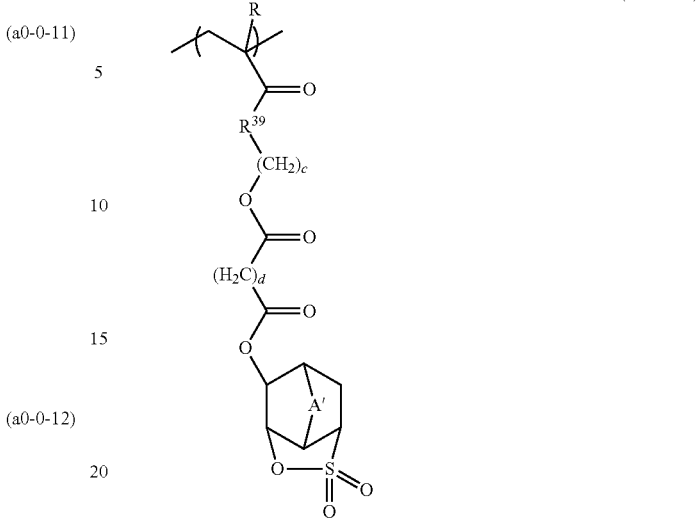
(a0-0-12b)

In the formulae, R, $R^{39}$ and A' are the same as defined above; c and d are the same as defined above; and f represents an integer of 1 to 5 (preferably an integer of 1 to 3).

As the structural unit (a0) contained in the component (A1), 1 type of structural unit may be used, or 2 or more types may be used.

In terms of achieving an excellent shape for a resist pattern formed using a positive resist composition containing the component (A1) and excellent lithography properties such as EL margin, LWR and mask reproducibility, the amount of the structural unit (a0) within the component (A1), based on the combined total of all structural units constituting the component (A1) is preferably 1 to 60 mol %, more preferably 5 to 55 mol %, still more preferably 10 to 50 mol %, and most preferably 15 to 45 mol %.

[Structural Unit (a2)]

The structural unit (a2) is a structural unit containing a lactone-containing cyclic group.

The term "lactone-containing cyclic group" refers to a cyclic group including one ring containing a —O—C(=O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water (especially in an alkali developing process).

As the lactone-containing cyclic group, there is no particular limitation, and an arbitrary group may be used.

Specific examples of lactone-containing monocyclic groups include a group in which one hydrogen atom has been removed from a 4- to 6-membered lactone ring, such as a group in which one hydrogen atom has been removed from β-propionolatone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

As the structural unit (a2), there is no particular limitation as long as it is a structural unit containing a lactone-containing cyclic group, and an arbitrary structural unit may be used.

The structural unit (a2) is preferably a structural unit derived from an acrylate ester which may have the hydrogen atom bonded to the carbon atom on the α-position substituted with a substituent and contains a lactone-containing cyclic group.

More specifically, examples of the structural unit (a2) include structural units represented by general formulas (a2-1) to (a2-5) shown below.

[Chemical Formula 31]

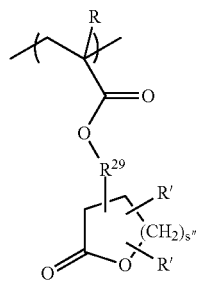

(a2-1)

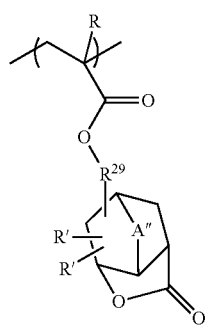

(a2-2)

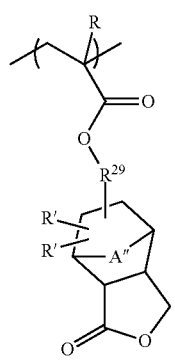

(a2-3)

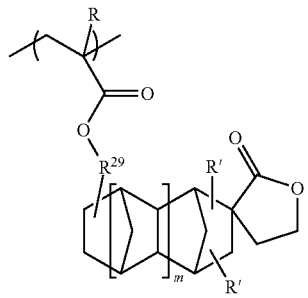

(a2-4)

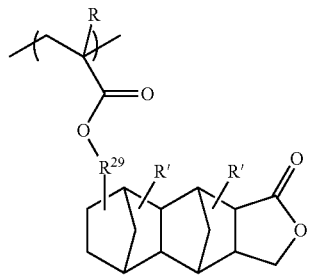

(a2-5)

In the formulas, R represents a hydrogen atom, an alkyl group of 1 to 5 carbon atoms or a halogenated alkyl group of 1 to 5 carbon atoms; each R' independently represents a hydrogen atom, an alkyl group, an alkoxy group, a halogen atom, a halogenated alkyl group, a hydroxy group, an oxygen atom (=O), —COOR", OC(=O)R", a hydroxyalkyl group or a cyano group, wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined above.

As the alkyl group, alkoxy group, halogen atom, halogenated alkyl group, —COOR", —OC(=O)R" and hydroxyalkyl group for R', the same alkyl groups, alkoxy groups, halogen atoms, halogenated alkyl groups, —COOR", —OC(=O)R" (R" is the same as defined above) and hydroxyalkyl groups as those described above as the substituent for the —SO$_2$— containing cyclic group can be mentioned.

As A", an alkylene group of 1 to 5 carbon atoms or —O— is preferable, more preferably an alkylene group of 1 to 5 carbon atoms, and most preferably a methylene group.

$R^{29}$ represents a single bond or a divalent linking group. Examples of divalent linking groups include the same divalent linking groups as those described above for $Y^2$ in general formula (a1-0-2). Among these, an alkylene group, an ester bond (—C(=O)—O—) or a combination thereof is preferable. The alkylene group as a divalent linking group for $R^{29}$ is preferably a linear or branched alkylene group. Specific examples include the same linear alkylene groups and branched alkylene groups as those described above for the aliphatic hydrocarbon group represented by $Y^2$.

s" is preferably 1 or 2.

Specific examples of structural units represented by general formulas (a2-1) to (a2-5) are shown below.

In the formulae shown below, $R^\alpha$ represents a hydrogen atom, a methyl group or a trifluoromethyl group.

[Chemical Formula 32]
(a2-1-1) 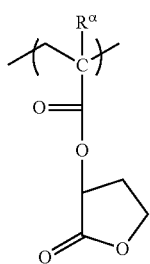
(a2-1-2) 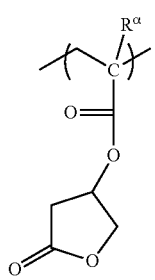
(a2-1-3) 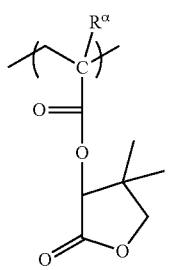
(a2-1-4) 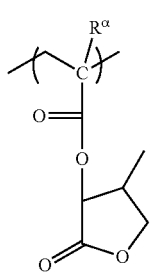
(a2-1-5) 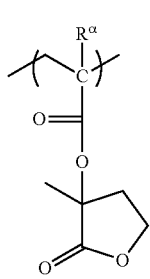
-continued
(a2-1-6) 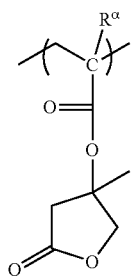
(a2-1-7) 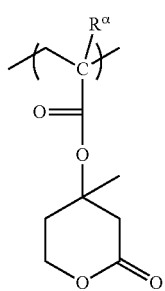
(a2-1-8) 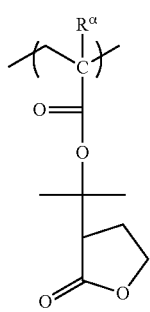
(a2-1-9) 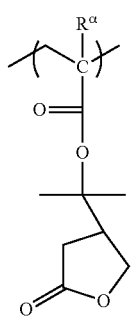
(a2-1-10) 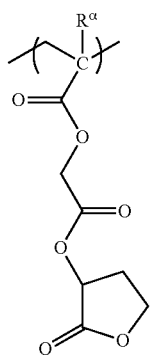

(a2-1-11)
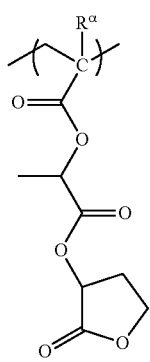
(a2-1-12)
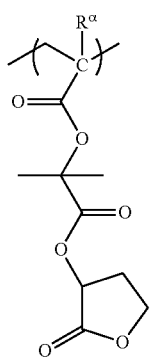
(a2-1-13)
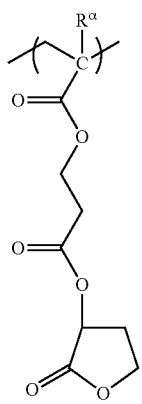
[Chemical Formula 33]
(a2-2-1)
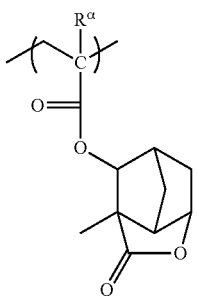
(a2-2-2)
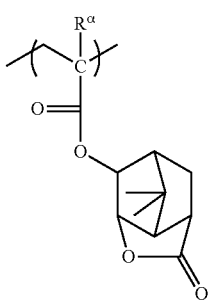
(a2-2-3)
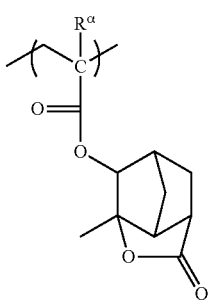
(a2-2-4)
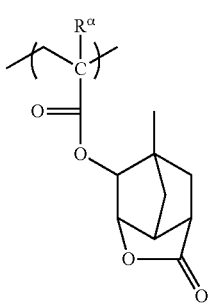
(a2-2-5)
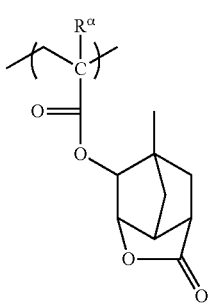
(a2-2-6)

-continued
(a2-2-7)
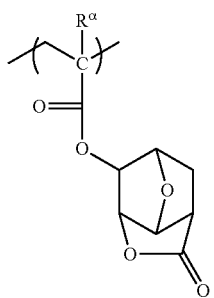
(a2-2-8)
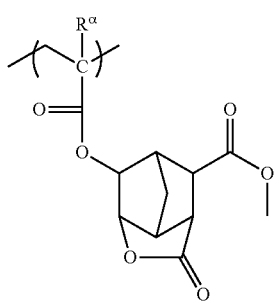
(a2-2-9)
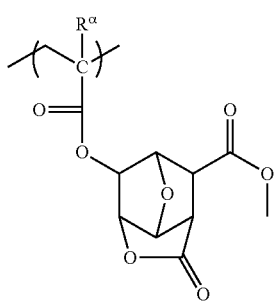
(a2-2-10)
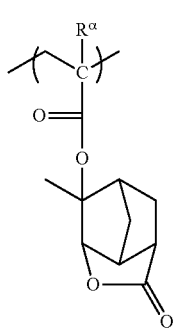
(a2-2-11)
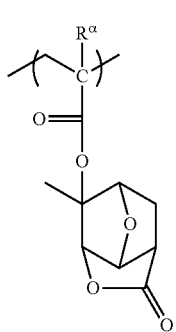
-continued
(a2-2-12)
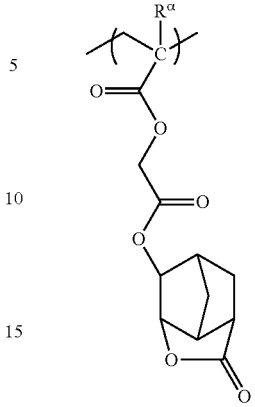
(a2-2-13)
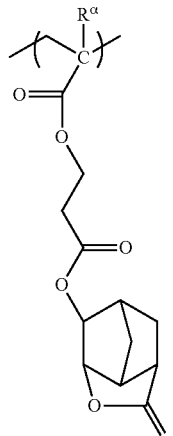
(a2-2-14)
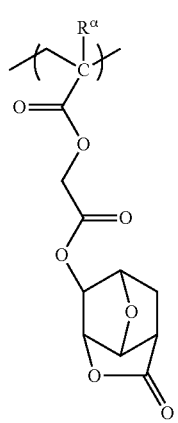

(a2-2-15) 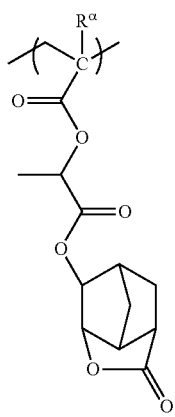
(a2-2-16) 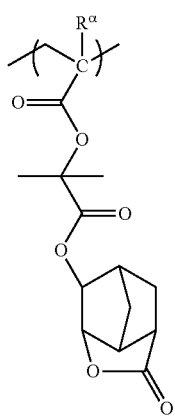
(a2-2-17) 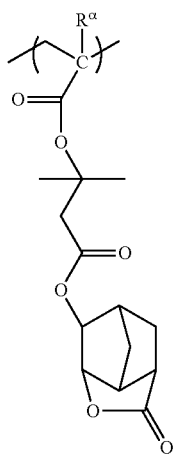
[Chemical Formula 34]
(a2-3-1) 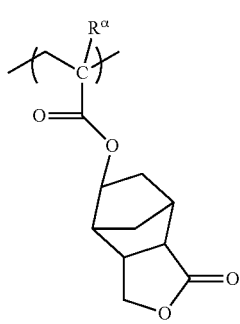
(a2-3-2) 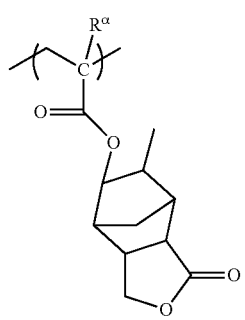
(a2-3-3) 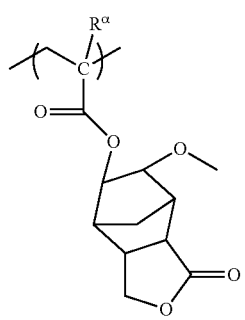
(a2-3-4) 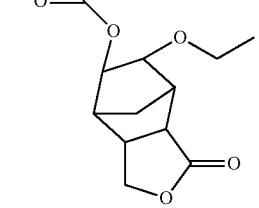
(a2-3-5) 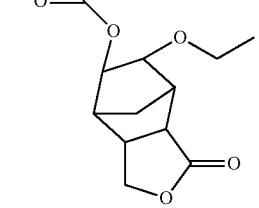
[Chemical Formula 35]
(a2-4-1) 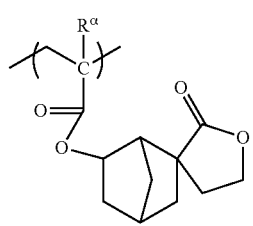

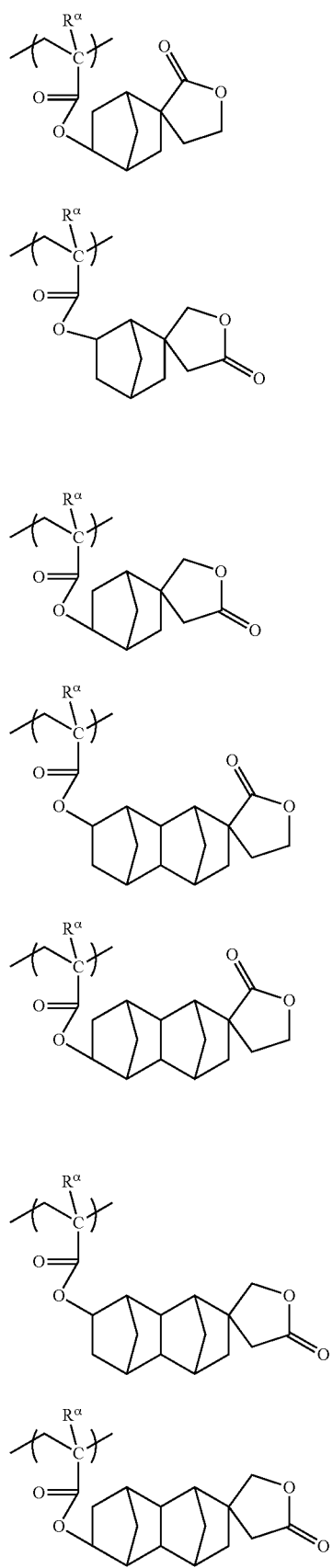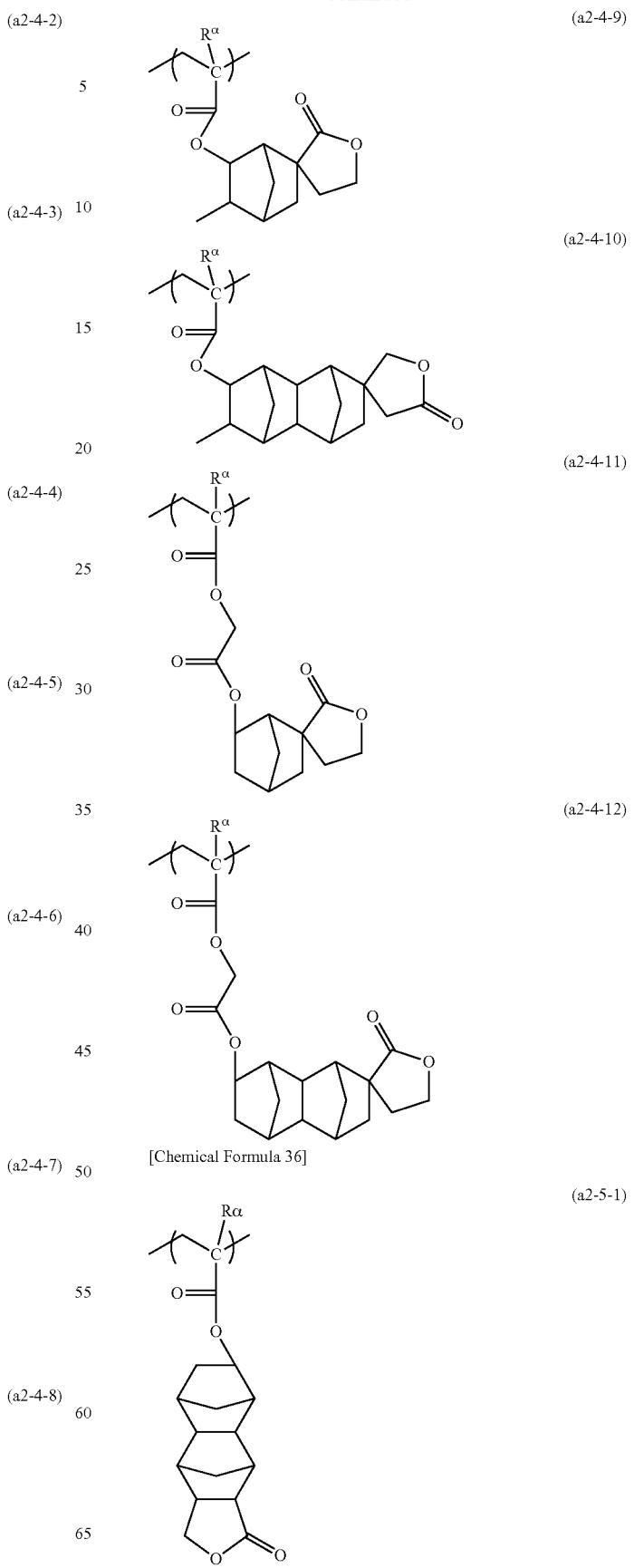

(a2-5-2)
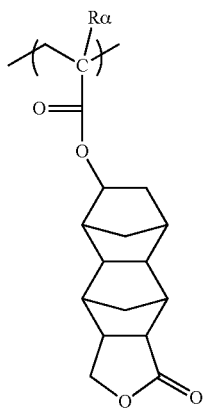

(a2-5-3)
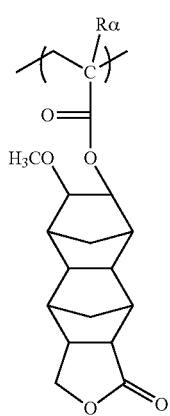

(a2-5-4)
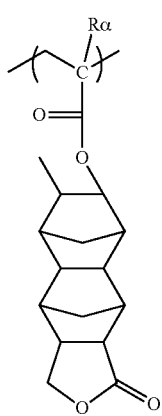

(a2-5-5)
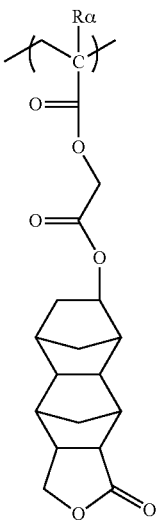

(a2-5-6)
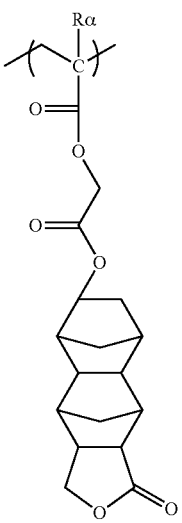

As the structural unit (a2) contained in the component (A1), 1 type of structural unit may be used, or 2 or more types may be used.

As the structural unit (a2), at least one structural unit selected from the group consisting of formulas (a2-1) to (a2-5) is preferable, and at least one structural unit selected from the group consisting of formulas (a2-1) to (a2-3) is more preferable. Of these, it is preferable to use at least one structural unit selected from the group consisting of structural units represented by formulas (a1-0-1), (a2-1-2), (a2-2-1), (a2-2-7), (a2-3-1) and (a2-3-5).

In the component (A1), the amount of the structural unit (a2) based on the combined total of all structural units constituting the component (A1) is preferably 5 to 60 mol %, more preferably 10 to 50 mol %, and still more preferably 10 to 45 mol %.

When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units.

[Structural Unit (a3)]

The structural unit (a3) is a structural unit containing a polar group-containing aliphatic hydrocarbon group (provided that the structural units that fall under the definition of structural units (a1), (a0) and (a2) are excluded).

When the component (A1) includes the structural unit (a3), the hydrophilicity of the component (A1) is enhanced, thereby contributing to improvement in resolution.

Examples of the polar group include a hydroxyl group, cyano group, carboxyl group, or hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and cyclic aliphatic hydrocarbon groups (cyclic groups). These cyclic groups can be selected appropriately from the multitude of groups that have been proposed for the resins of resist compositions designed for use with ArF excimer lasers. The cyclic group is preferably a polycyclic group, more preferably a polycyclic group of 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

As the structural unit (a2), there is no particular limitation as long as it is a structural unit containing a polar group-containing aliphatic hydrocarbon group, and an arbitrary structural unit may be used.

The structural unit (a3) is preferably a structural unit derived from an acrylate ester which may have the hydrogen atom bonded to the carbon atom on the α-position substituted with a substituent and contains a polar group-containing aliphatic hydrocarbon group.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 37]

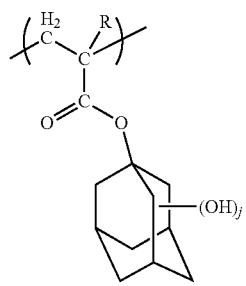

(a3-1)

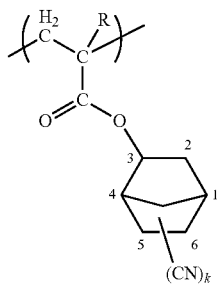

(a3-2)

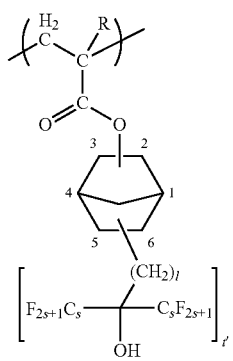

(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 type of structural unit may be used, or 2 or more types may be used.

The amount of the structural unit (a3) within the component (A1) based on the combined total of all structural units constituting the component (A1) is preferably 5 to 50 mol %, more preferably 5 to 40 mol %, and still more preferably 5 to 25 mol %.

When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

[Structural Unit (a5)]

The structural unit (a5) is a structural unit which generates base upon exposure.

The structural unit (a5) may be any structural unit having a portion capable of generating a base upon exposure, and examples thereof include a compound containing a carbamate group (a urethane bond), a compound containing an acyloxyimino group, an ionic compound (an anion-cation complex), and a compound containing a carbamoyloxyimino group.

Further, structural units having a ring structure are preferable, and examples thereof include structural units having a ring skeleton such as benzene, naphthalene, anthracene, xanthone, thioxanthone, anthraquinone or fluorene.

As the structural unit (a5), a structural unit derived from a compound having an ethylenic double bond is preferable.

In the present description, the expression "structural unit derived from a compound having an ethylenic double bond" refers to a structural unit that is formed by the cleavage of the ethylenic double bond of the compound having an ethylenic double bond.

Examples of the compound having an ethylenic double bond include acrylic acid or an ester thereof which may have the hydrogen atom bonded to the carbon atom on the α-position substituted with a substituent, acrylamide or a derivative thereof in which the hydrogen atom bonded to the carbon atom on the α-position may be substituted with a substituent, a vinylaromatic compound in which the hydrogen atom bonded to the carbon atom on the α-position may be substituted with a substituent, a cycloolefin or a derivative thereof, and a vinylsulfonate ester. Further examples include carbamic acid or an ester thereof in which the hydrogen atom of —$NH_2$ has been substituted with a vinyl group or the like.

Among these, acrylic acid or an ester thereof which may have the hydrogen atom bonded to the carbon atom on the α-position substituted with a substituent, acrylamide or a derivative thereof in which the hydrogen atom bonded to the carbon atom on the α-position may be substituted with a substituent, or a vinylaromatic compound in which the hydrogen atom bonded to the carbon atom on the α-position may be substituted with a substituent is preferable.

Examples of "acrylamide and derivatives thereof" include acrylamide in which the hydrogen atom bonded to the carbon atom on the α-position may be substituted with a substituent (hereafter, sometimes referred to as "(α-substituted)" acrylamide), and a compound in which either or both terminal hydrogen atoms on the amino group of acrylamide is substituted with a substituent.

As the substituent to be bonded to the carbon atom on the α-position of acrylamide and derivatives thereof, the same substituents as those described above for the substituent to be bonded to the carbon atom on the α-position of an α-substituted acrylate ester can be mentioned.

As the substituent which substitutes either or both terminal hydrogen atoms on the amino group of acrylamide, an organic group is preferable.

Examples of the compound in which in which either or both terminal hydrogen atoms on the amino group of (α-substituted) acrylamide is substituted with a substituent include a compound in which —C(=O)—O— bonded to the carbon atom on the α-position of the aforementioned (α-substituted) acrylate ester is replaced by —C(=O)—N($R^b$)— (in the formula, $R^b$ represents a hydrogen atom or an alkyl group of 1 to 5 carbon atoms).

In the formula, the alkyl group for $R^b$ is preferably linear or branched.

A "vinyl aromatic compound" is a compound having an aromatic ring and one vinyl group bonded to the aromatic ring, and examples thereof include styrene and derivatives thereof, and vinylnaphthalene and derivatives thereof.

As the substituent to be bonded to the carbon atom on the α-position of the vinyl aromatic compound (i.e., the carbon atom of the vinyl group which is bonded to the aromatic ring), the same substituents as those described above for the substituent to be bonded to the carbon atom on the α-position of an α-substituted acrylate ester can be mentioned.

Herebelow, a vinyl aromatic compound in which the hydrogen atom bonded to the carbon atom on the α-position is substituted with a substituent is sometimes referred to as "(α-substituted) vinyl aromatic compound".

Examples of "styrene and derivatives thereof" include styrene which may have the hydrogen atom bonded to the carbon atom on the α-position substituted with a substituent, and a hydrogen atom bonded to the benzene ring substituted with a substituent other than a hydroxy group (hereafter, sometimes referred to as "(α-substituted) styrene"); hydroxystyrene which may have the hydrogen atom bonded to the carbon atom on the α-position substituted with a substituent, and a hydrogen atom bonded to the benzene ring substituted with a substituent other than a hydroxy group (hereafter, sometimes referred to as "(α-substituted) hydroxystyrene"); a compound in which the hydrogen atom within the hydroxy group of (α-substituted) hydroxystyrene is substituted with an organic group; vinylbenzoic acid which may have the hydrogen atom bonded to the carbon atom on the α-position substituted with a substituent, and a hydrogen atom bonded to the benzene ring substituted with a substituent other than a hydroxy group and a carboxy group (hereafter, sometimes referred to as "(α-substituted) vinylbenzoic acid"); and a compound in which the hydrogen atom within the carboxy group of (α-substituted) vinylbenzoic acid is substituted with an organic group.

Hydroxystyrene is a compound which has 1 vinyl group and at least 1 hydroxy group bonded to a benzene ring. The number of hydroxy groups bonded to the benzene ring is preferably 1 to 3, and most preferably 1. The bonding position of the hydroxy group on the benzene ring is not particularly limited. When there is 1 hydroxy group, a para-4th position from the bonding position of the vinyl group is preferable. When there are 2 or more hydroxy groups, a desired combination of the bonding positions can be used.

Vinylbenzoic acid is a compound in which one vinyl group is bonded to the benzene ring of benzoic acid.

The bonding position of the vinyl group on the benzene ring is not particularly limited.

The substituent other than a hydroxy group and a carboxy group which may be bonded the benzene ring of styrene or a derivative thereof is not particularly limited, and examples thereof include a halogen atom, an alkyl group of 1 to 5 carbon atoms, and a halogenated alkyl group of 1 to 5 carbon atoms. Examples of the halogen atom include a fluorine atom, a chlorine atom, a bromine atom and an iodine atom, and a fluorine atom is particularly desirable.

Examples of "vinylnaphthalene and derivatives thereof" include vinylnaphthalene which may have the hydrogen atom bonded to the carbon atom on the α-position substituted with a substituent, and a hydrogen atom bonded to the naphthalene ring substituted with a substituent other than a hydroxy group (hereafter, sometimes referred to as "(α-substituted) vinylnaphthalene"); vinyl(hydroxynaphthalene) which may have the hydrogen atom bonded to the carbon atom on the α-position substituted with a substituent, and a hydrogen atom bonded to the naphthalene ring substituted with a substituent other than a hydroxy group (hereafter, sometimes referred to as "(α-substituted) vinyl(hydroxynaphthalene)"); and a compound in which the hydrogen atom within the hydroxy group of (α-substituted) vinyl(hydroxynaphthalene) is substituted with an organic group.

Vinyl(hydroxynaphthalene) is a compound which has 1 vinyl group and at least 1 hydroxy group bonded to a naphthalene ring. The vinyl group may be bonded to the 1st or 2nd position of the naphthalene ring. The number of hydroxy groups bonded to the naphthalene ring is preferably 1 to 3, and most preferably 1. The bonding position of the hydroxy group on the naphthalene ring is not particularly limited. When the vinyl group is bonded to the 1st or 2nd position of the naphthalene ring, the hydroxy group is preferably bonded to either one of the 5th to 8th position of the naphthalene ring. In particular, when the number of hydroxy group is 1, the hydroxy group is preferably bonded to either one of the 5th to 7th position of the naphthalene ring, and more preferably the 5th or 6th position. When there are 2 or more hydroxy groups, a desired combination of the bonding positions can be used.

As the substituent which may be bonded to the naphthalene ring of vinylnaphthalene and derivatives thereof, the same substituents as those described above for the substituent which may be bonded to the benzene ring of the (α-substituted) styrene can be mentioned.

A "carbamate ester" refers to a compound in which the hydrogen atom of the hydroxy group of carbamic acid (HO—C(=O)—NH$_2$) has been substituted with an organic group.

Examples of "carbamic acid or an ester thereof in which the hydrogen atom of —NH$_2$ has been substituted with a vinyl group or the like" include N-vinylcarbamic acid or an ester thereof, and N-allylcarbamic acid or an ester thereof. With respect to the CH$_2$=CH— group of these compounds, the hydrogen atom bonded to the carbon atom on the substituent side (the side on which —NH— or —CH$_2$—NH— is bonded), like the other compounds having an ethylenic double bond, may be substituted with a substituent. Hereafter, vinylcarbamic acid or a vinylcarbamic acid derivative, and the aforementioned compound in which the hydrogen atom bonded to the carbon atom on the substituent side has been substituted with a substituent are collectively referred to as a "(substituted) vinylcarbamic acid" or a "(substituted) vinylcarbamic acid derivative".

Specific examples of the structural unit derived from an (α-substituted) acrylic acid or an ester thereof include a structural unit represented by general formula (U-1) shown below.

Specific examples of the structural unit derived from an (α-substituted) acrylamide or a derivative thereof include a structural unit represented by general formula (U-2) shown below.

Among the structural units derived from an (α-substituted) vinylaromatic compound, specific examples of the structural unit derived from an (α-substituted) styrene or a derivative thereof include a structural unit represented by general formula (U-3) shown below. Further, specific examples of the structural unit derived from an (α-substituted) vinylnaphthalene or a derivative thereof include a structural unit represented by general formula (U-4) shown below.

Specific examples of the structural unit derived from an (α-substituted) vinylcarbamic acid derivative include a structural unit represented by general formula (U-5) shown below.

Examples of the structural unit (a5) include structural units represented by general formulae (U-1) to (U-4) shown below which have a portion capable of generating base upon exposure, and a structural unit represented by general formula (U-5) shown below.

[Chemical Formula 38]

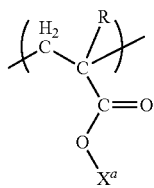
(U-1)

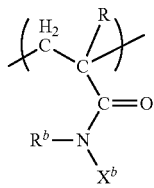
(U-2)

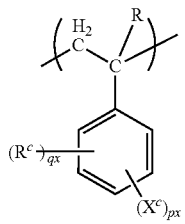
(U-3)

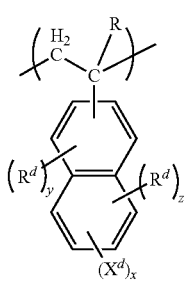
(U-4)

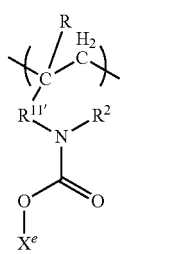
(U-5)

In the formulae, R represents a hydrogen atom, an alkyl group of 1 to 5 carbon atoms or a halogenated alkyl group of 1 to 5 carbon atoms; $X^a$, $X^b$ and $X^e$ each independently represents a hydrogen atom or an organic group; $X^c$ and $X^d$ each independently represents a hydrogen atom, a hydroxy group or an organic group; $R^b$ represents a hydrogen atom or an alkyl group of 1 to 5 carbon atoms; $R^c$ and $R^d$ each independently represents a halogen atom, —COOX$^e$ ($X^e$ represents a hydrogen atom or an organic group), an alkyl group of 1 to 5 carbon atoms or a halogenated alkyl group of 1 to 5 carbon atoms; px represents an integer of 0 to 3, qx represents an integer of 0 to 5, and px+qx=1 to 5, provided that, when qx is an integer of 2 or more, the plurality of $R^c$ groups may be the same or different from each other; x represents an integer of 0 to 3, y represents an integer of 0 to 3, z represents an integer of 0 to 4, and x+y+z=1 to 7, provided that, when y+z is an integer of 2 or more, the plurality of $R^d$ groups may be the same or different from each other; $R^{11'}$ represents a single bond or a divalent aliphatic hydrocarbon group, and $R^2$ represents a hydrogen atom, a linear, branched or cyclic alkyl group of 1 to 10 carbon atoms or an aryl group of 6 to 10 carbon atoms, provided that $R^{11'}$ and $R^2$ may be mutually bonded to form a ring with the nitrogen atom, and the alkyl group or the aryl group for $R^2$ may have a substituent.

As a preferable example of the structural unit (a5), a structural unit (a51) represented by general formula (a5-1) shown below can be given.

[Chemical Formula 39]

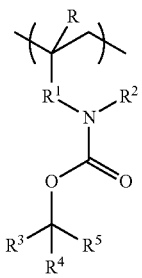

(a5-1)

In the formula, R is the same as defined above; $R^1$ represents a single bond or a divalent linking group, and $R^2$ represents a hydrogen atom, a linear, branched or cyclic alkyl group of 1 to 10 carbon atoms or an aryl group of 6 to 10 carbon atoms, wherein $R^1$ and $R^2$ may be mutually bonded to form a ring with the nitrogen atom, and the alkyl group or the aryl group for $R^2$ may have a substituent; $R^3$, $R^4$ and $R^5$ each independently represents a hydrogen atom, a linear, branched or cyclic alkyl group of 1 to 10 carbon atoms or an aryl group of 6 to 14 carbon atoms, wherein $R^3$ and $R^4$, $R^4$ and $R^5$, or $R^3$ and $R^5$ may be mutually bonded to form a ring with the carbon atom to which the $R^3$, $R^4$, and $R^5$ groups are bonded, and the alkyl group or the aryl group for $R^3$, $R^4$ and $R^5$ may have a substituent; provided that not all of $R^3$, $R^4$ and $R^5$ represents a hydrogen atom or an alkyl group.

In the formula (a5-1), R is the same as defined above.

In the formula (a5-1), $R^1$ represents a single bond or a divalent linking group.

The divalent linking group for $R^1$ is not particularly limited, and the same divalent linking groups as those described above for $Y^2$ in the aforementioned formula (a1-0-2) can be mentioned. Among these, as $R^1$, a single bond, a methylene group, an ethylene group, a phenylene group, phenylmethylene group, a phenylethylene group, a phenylpropylene group or a group represented by the aforementioned formula —C(=O)—O—$Y^{22}$— is preferable, and a single bond or a group represented by the aforementioned formula —C(=O)—O—$Y^{22}$— is more preferable.

In the formula (a5-1), $R^2$ represents a hydrogen atom, a linear, branched or cyclic alkyl group of 1 to 10 carbon atoms or an aryl group of 6 to 10 carbon atoms.

As the alkyl group and the aryl group for $R^2$, the "linear, branched or cyclic alkyl group of 1 to 10 carbon atoms or aryl group of 6 to 10 carbon atoms" described above as examples of the divalent hydrocarbon group for the aforementioned $Y^2$ can be mentioned.

The alkyl group and the aryl group for $R^2$ may have a substituent. Examples of the substituent for $R^2$ include the same substituents as those for the divalent hydrocarbon group (linear or branched aliphatic hydrocarbon group, alicyclic hydrocarbon group or aromatic hydrocarbon group) represented by $Y^2$.

In the formula (a5-1), $R^1$ and $R^2$ may be mutually bonded to form a ring with the nitrogen atom. As the ring, a ring having 3 to 8 carbon atoms is preferable, and a ring having 4 to 6 carbon atoms is particularly desirable.

Specific examples of the ring include a group in which $R^1$ is a group represented by the formula —C(=O)—O—$Y^{22}$—, and a ring is formed by $Y^{22}$, $R^2$ and the nitrogen atom bonded thereto.

In the formula (a5-1), $R^3$, $R^4$ and $R^5$ each independently represents a hydrogen atom, a linear, branched or cyclic alkyl group of 1 to 10 carbon atoms or an aryl group of 6 to 14 carbon atoms. However, not all of $R^3$, $R^4$ and $R^5$ represents a hydrogen atom or an alkyl group.

As the alkyl group and the aryl group for $R^3$, $R^4$ and $R^5$, the "linear, branched or cyclic alkyl group of 1 to 10 carbon atoms or aryl group of 6 to 14 carbon atoms" described above as examples of the divalent hydrocarbon group for the aforementioned $Y^2$ can be mentioned.

The alkyl group for $R^3$, $R^4$ and $R^5$ may have a substituent. In this case, examples of the substituent for $R^3$, $R^4$ and $R^5$ include the same substituents as those for the divalent hydrocarbon group (linear or branched aliphatic hydrocarbon group or alicyclic hydrocarbon group) represented by $Y^2$.

Further, the aryl group for $R^3$, $R^4$ and $R^5$ may have a substituent. In this case, examples of the substituent for $R^3$, $R^4$ and $R^5$ include a linear, branched or cyclic alkyl group of 1 to 6 carbon atoms, an alkoxy group of 1 to 6 carbon atoms, a nitro group, a halogen atom, cyano group and a trifluoromethyl group.

Among these, as $R^3$, $R^4$ and $R^5$, it is preferable that at least one of the three groups represents an aryl group of 6 to 14 carbon atoms which may have a substituent.

In the formula (a5-1), $R^3$ and $R^4$, $R^4$ and $R^5$, or $R^3$ and $R^5$ may be mutually bonded to form a ring with the carbon atom bonded thereto. As the ring, a non-aromatic ring having 3 to 10 carbon atoms is preferable, and a non-aromatic ring having 4 to 6 carbon atoms is particularly desirable.

As shown by the reaction formula below, the structural unit (a51) represented by the aforementioned general formula (a5-1) is decomposed to generate an amine compound (base), a carbon dioxide gas and other compound.

[Chemical Formula 40]

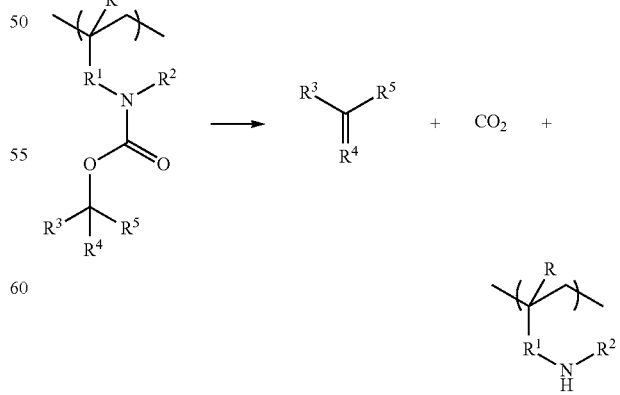

In the formula, R, $R^1$, $R^2$, $R^3$, $R^4$ and $R^5$ are the same as defined above.

Specific examples of the structural unit (a51) are shown below.
In the formulae below, $R^\alpha$, R, $R^1$, $R^2$, $R^3$, $R^4$ and $R^5$ are the same as defined above.
[Chemical Formula 41]
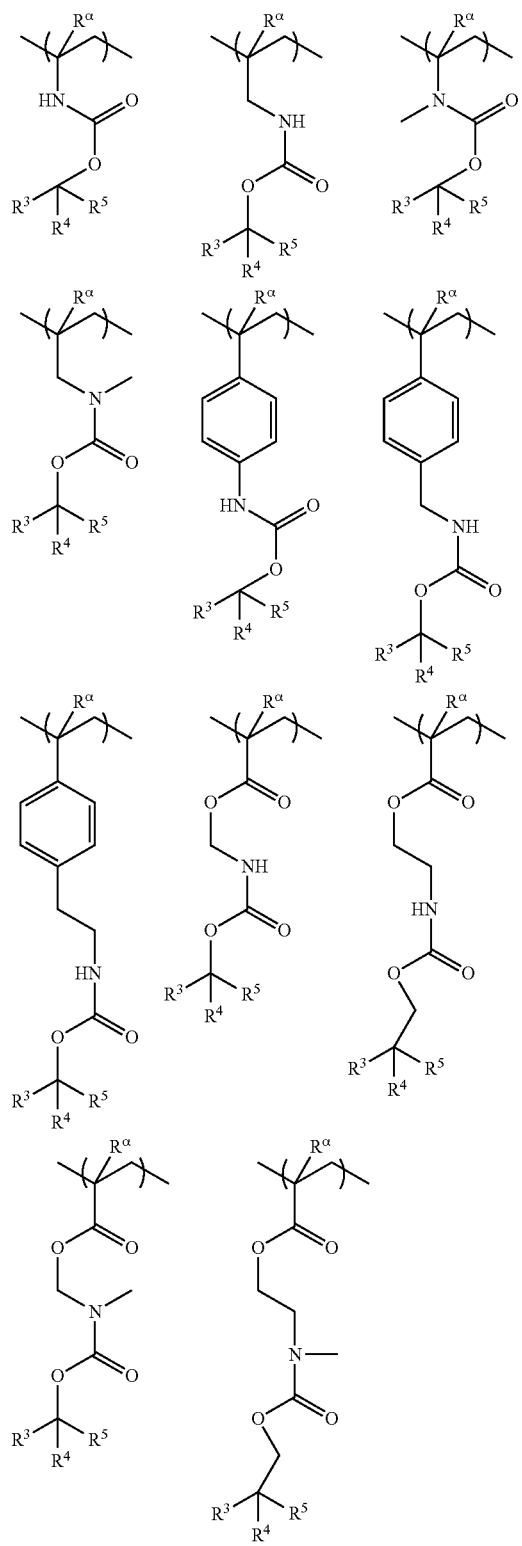
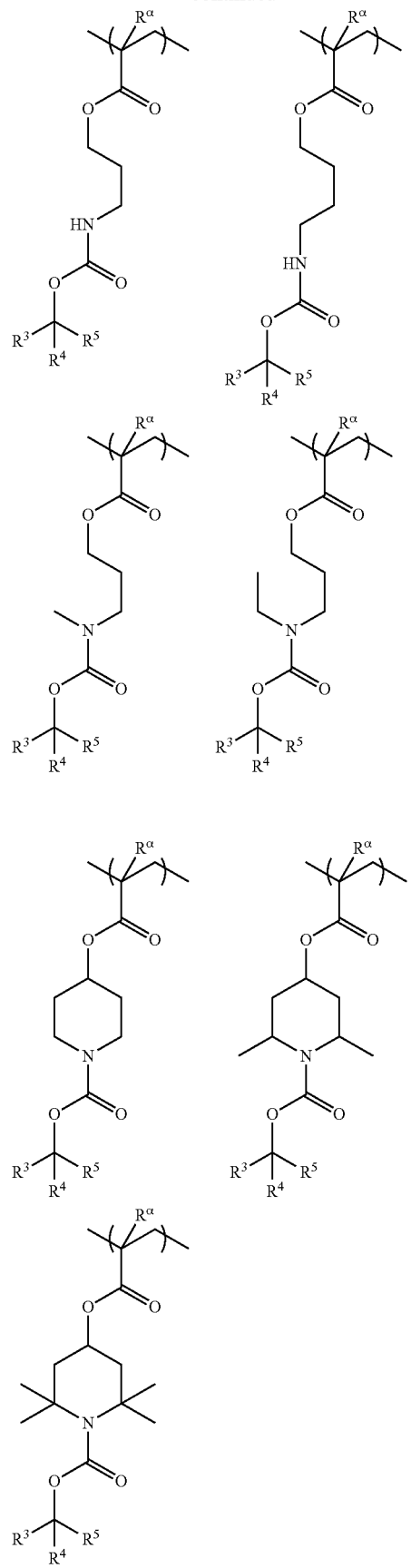

[Chemical Formula 42]
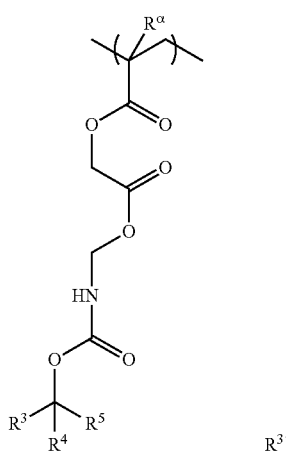 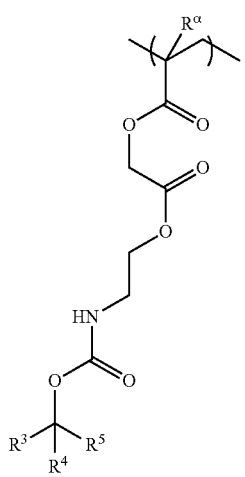
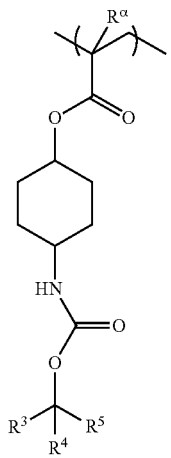 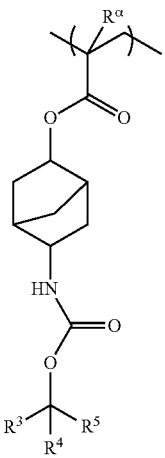
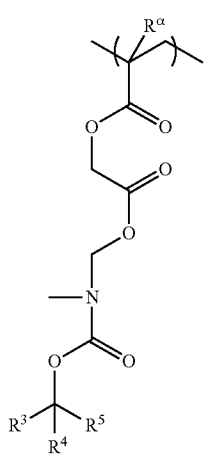 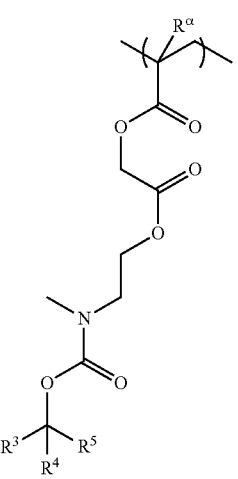
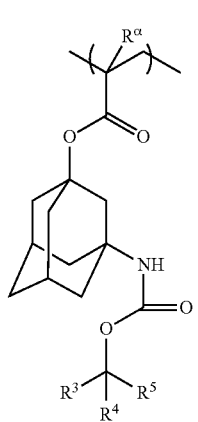 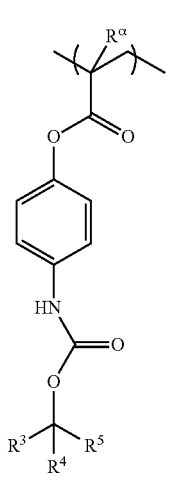
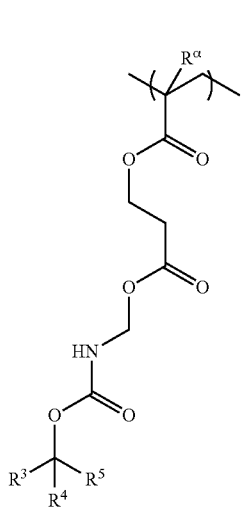 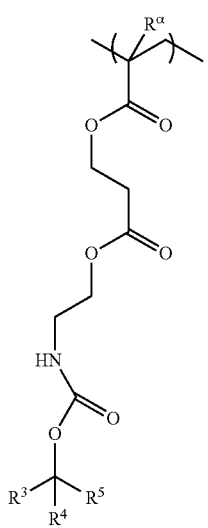
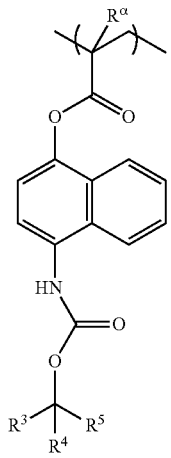 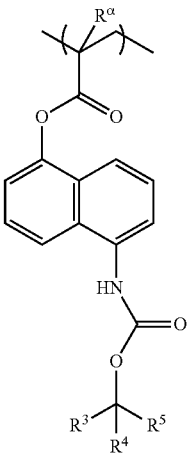

[Chemical Formula 43]
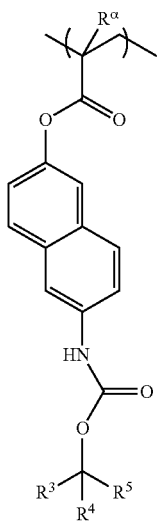
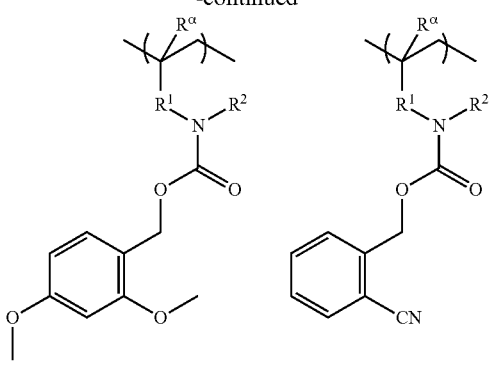
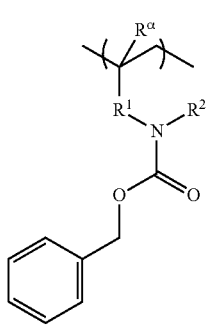
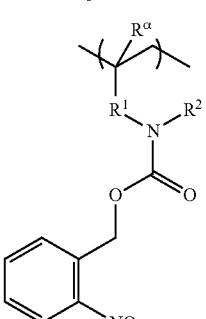
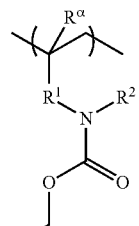
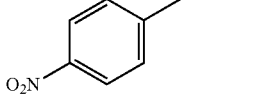
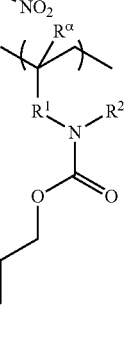
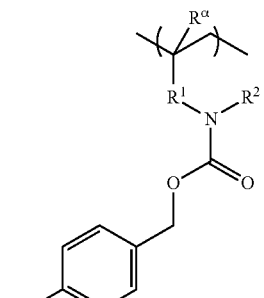
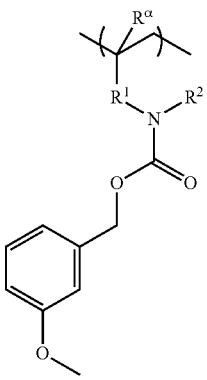
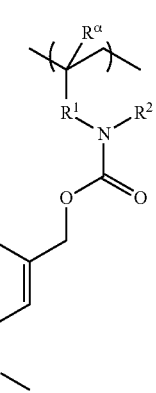
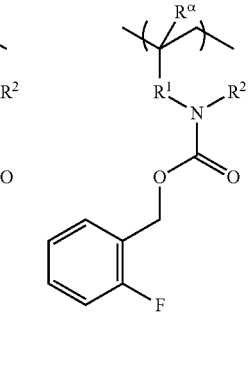

-continued

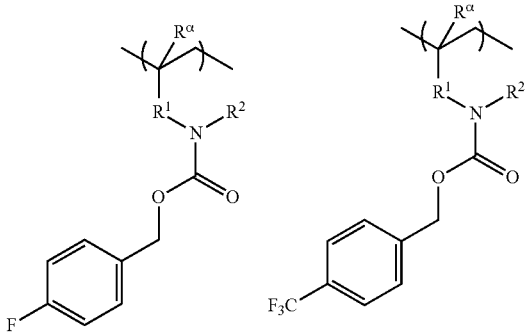

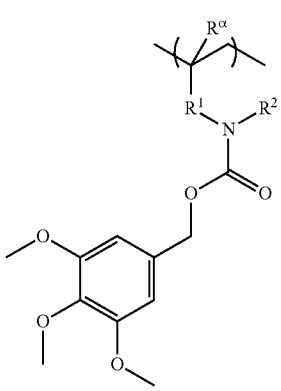

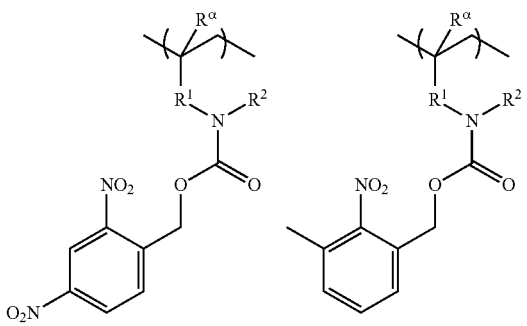

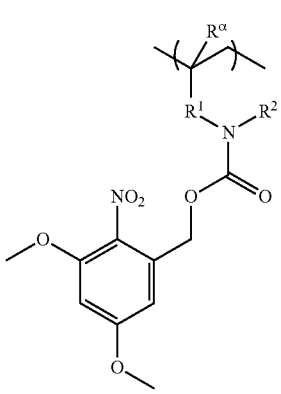

In the component (A1), as the structural unit (a5), one type of structural unit may be used alone, or two or more types of structural units may be used in combination.

In the component (A1), the amount of the structural unit (a5) based on the combined total of all structural units constituting the component (A1) is preferably 1 to 50 mol %, more preferably 1 to 30 mol %, and still more preferably 1 to 20 mol %.

When the amount of the structural unit (a5) is at least as large as the lower limit of the above-mentioned range, the film retentiveness of the resist film at exposed portions becomes excellent, and the resolution and the shape of the formed resist pattern is further improved. On the other hand, when the amount of the structural unit (a5) is no more than the upper limit of the above-mentioned range, a good balance can be reliably achieved with the other structural units. Also, the transparency of the formed resist film becomes excellent.

In the component (A1), the amount of the structural unit (a5) based on the combined total of all structural units constituting the component (A1) is preferably 0.5 to 50 mol %, more preferably 0.5 to 30 mol %, and still more preferably 0.5 to 20 mol %. When the amount of the structural unit (a5) is within the above-mentioned range, the film retentiveness of the resist film at exposed portions becomes excellent, and the resolution and the shape of the formed resist pattern are further improved.

[Other Structural Unit]

The component (A1) may also have a structural unit other than the above-mentioned structural units (a1), (a0), (a2) and (a3), as long as the effects of the present invention are not impaired.

As such a structural unit, any other structural unit which cannot be classified as the aforementioned structural units can be used without any particular limitation, and any of the multitude of conventional structural units used within resist resins for ArF excimer lasers or KrF excimer lasers (and particularly for ArF excimer lasers) can be used.

Examples of the other structural unit include a structural unit (a4) derived from an acrylate ester which may have the hydrogen atom bonded to the carbon atom on the α-position substituted with a substituent and contains an acid non-dissociable aliphatic polycyclic group, a structural unit (a6) derived from hydroxystyrene which may have the hydrogen atom bonded to the carbon atom on the α-position substituted with a substituent, and a structural unit (a7) derived from styrene which may have the hydrogen atom bonded to the carbon atom on the α-position substituted with a substituent.

(Structural Unit (a4))

The structural unit (a4) is a structural unit derived from an acrylate ester which may have the hydrogen atom bonded to the carbon atom on the α-position substituted with a substituent and contains an acid non-dissociable aliphatic polycyclic group.

In the structural unit (a4), examples of this polycyclic group include the same polycyclic groups as those described above in relation to the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 44]

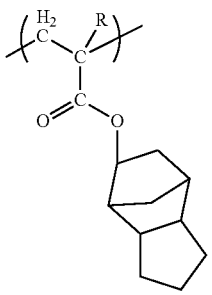
(a4-1)

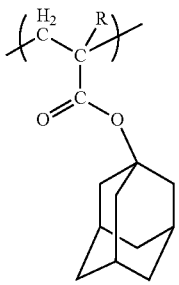
(a4-2)

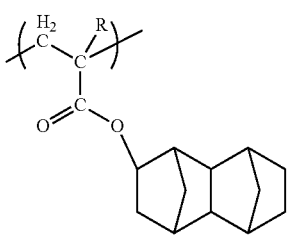
(a4-3)

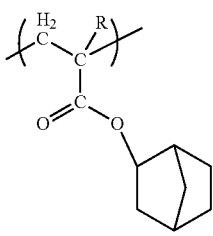
(a4-4)

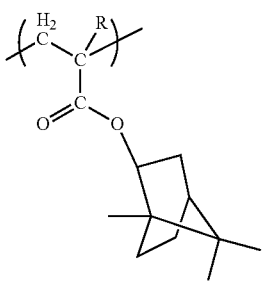
(a4-5)

In the formulae, R is the same as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

(Structural Unit (a6))

The structural unit (a6) is a structural unit derived from hydroxystyrene which may have the hydrogen atom bonded to the carbon atom on the α-position substituted with a substituent.

A "structural unit derived from a hydroxystyrene" refers to a structural unit that is formed by the cleavage of the ethylenic double bond of a hydroxystyrene.

As the substituent which may substitute the hydrogen atom on the α-position of hydroxystyrene, the same substituents as those described above for the substituent on the α-position of an acrylate ester explained in relation to the structural unit (a1) can be given. Specific examples thereof include an alkyl group of 1 to 5 carbon atoms, a halogenated alkyl group of 1 to 5 carbon atoms and a hydroxyalkyl group. Among these, a hydrogen atom or an alkyl group of 1 to 5 carbon atoms is preferable.

The benzene ring of hydroxystyrene may have a substituent other than a hydroxy group bonded thereto. Examples of the substituent include a halogen atom, an alkyl group of 1 to 5 carbon atoms and a halogenated alkyl group of 1 to 5 carbon atoms. Examples of the halogen atom include a fluorine atom, a chlorine atom, a bromine atom and an iodine atom, and a fluorine atom is particularly desirable. Among these, as the substituent, an alkyl group of 1 to 5 carbon atoms is preferable.

As the structural unit (a6), in terms of obtaining excellent solubility in an organic solvent, excellent solubility in an alkali developing solution and excellent etching resistance, a structural unit represented by the aforementioned general formula (U-3) in which $X^c$ represents a hydroxy group, and px represents an integer of 1 to 3 is preferable.

When the structural unit (a6) is included in the component (A1), the amount of the structural unit (a6) based on the combined total of all the structural units that constitute the component (A1) is preferably within the range from 50 to 90 mol %, more preferably from 55 to 85 mol %, and still more preferably 60 to 80 mol %.

(Structural Unit (a7))

The structural unit (a7) is a structural unit derived from styrene which may have the hydrogen atom bonded to the carbon atom on the α-position substituted with a substituent.

A "structural unit derived from styrene" refers to a structural unit that is formed by the cleavage of the ethylenic double bond of styrene.

As the substituent which may substitute the hydrogen atom on the α-position of styrene, the same substituents as those described above for the substituent on the α-position of an acrylate ester explained in relation to the structural unit (a1) can be given. Among these, a hydrogen atom or an alkyl group of 1 to 5 carbon atoms is preferable.

The benzene ring of styrene may have a substituent bonded thereto. As the substituent, the same substituents as those described above for the substituent which may be bonded to the benzene ring of hydroxystyrene explained in relation to the structural unit (a6) can be mentioned. Among these, an alkyl group of 1 to 5 carbon atoms is preferable.

As the structural unit (a7), in terms of controlling the solubility in an alkali developing solution and improving the heat resistance and the dry etching resistance, a structural unit represented by the aforementioned general formula (U-4) in which $X^c$ represents an alkyl group of 1 to 5 carbon atoms is preferable.

When the structural unit (a7) is included in the component (A1), the amount of the structural unit (a7) based on the combined total of all the structural units that constitute the component (A1) is preferably within the range from 10 to 50 mol %, more preferably from 15 to 45 mol %, and still more preferably 20 to 40 mol %.

The component (A) is preferably a polymer including the structural unit (a1).

Specific examples of the component (A1) include a copolymer consisting of a repeating structure of a structural unit (a1) and a structural unit (a2); a copolymer consisting of a repeating structure of a structural unit (a1) and a structural unit (a0); a copolymer consisting of a repeating structure of a structural unit (a1), a structural unit (a2) and a structural unit (a3); a copolymer consisting of a repeating structure of a structural unit (a1), a structural unit (a2) and a structural unit (a5); a copolymer consisting of a repeating structure of a structural unit (a1), a structural unit (a0) and a structural unit (a5); a copolymer consisting of a repeating structure of a structural unit (a1), a structural unit (a0) and a structural unit (a3); a copolymer consisting of a repeating structure of a structural unit (a1), a structural unit (a0), a structural unit (a2) and a structural unit (a3); and a copolymer consisting of a repeating structure of a structural unit (a1), a structural unit (a0), a structural unit (a2), a structural unit (a3) and a structural unit (a5).

The weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) is not particularly limited, but is preferably 1.0 to 5.0, more preferably 1.0 to 3.0, and most preferably 1.0 to 2.5. Here, Mn is the number average molecular weight.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

As the monomers for deriving the corresponding structural units, commercially available monomers may be used, or the monomers may be synthesized by a conventional method.

As the component (A), one type may be used alone, or two or more types may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved, such as improvement in MEF and circularity, and reduction of roughness.

[Component (A2)]

Examples of the component (A2) include low molecular weight compounds that have a molecular weight of at least 500 and less than 4,000, contains a hydrophilic group, and also contains an acid dissociable group described above in connection with the component (A1). Specific examples include compounds containing a plurality of phenol skeletons in which part or all of the hydrogen atoms within hydroxyl groups have been substituted with the aforementioned acid dissociable groups.

Examples of the low-molecular weight compound include low molecular weight phenolic compounds in which a portion of the hydroxyl group hydrogen atoms have been substituted with an aforementioned acid dissociable group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3', 4'-trihydroxyphenyl)propane, tris(4-hydroxyphenyl) methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl) isopropyl]-4-[1,1-bis(4-hydroxyphenyl)ethyl]benzene, and dimers, trimers, tetramers, pentamers and hexamers of formalin condensation products of phenols such as phenol, m-cresol, p-cresol and xylenol. Needless to say, the low molecular weight phenol compound is not limited to these examples. In particular, a phenol compound having 2 to 6 triphenylmethane skeletons is preferable in terms of resolution and line width roughness (LWR). Also, there are no particular limitations on the acid dissociable group, and suitable examples include the groups described above.

In the resist composition used in the present invention, the amount of the component (A) can be appropriately adjusted depending on the thickness of the resist film to be formed, and the like.

<Acidic Compound Component which is Decomposed by Exposure to Exhibit Decreased Acidity; Component (J)>

The component (J) is an acidic compound component which is decomposed by exposure to exhibit decreased acidity. The component (J) prior to exposure has an acid strength capable of increasing the solubility of the component (A) in an alkali developing solution. After exposure, the component (J) is decomposed by the exposure energy to exhibit a decreased acidity. By the decrease in the acidity at exposed portions, the solubility of the component (A) in an alkali developing solution cannot be increased, or only slightly increases the solubility of the component (A) in an alkali developing solution. As a result, an excellent dissolution contrast can be obtained between the exposed portions and unexposed portions.

An acid "has an acid strength sufficient for increasing the solubility of the base component (A) in an alkali developing solution" includes acid, for example, when a polymeric compound (A1) having a structural unit (a1) is used, by conducting baking (PEB) after exposure (PEB; step (3) described later), the acid is capable of causing cleavage of at least part of the bond within the structure of the acid decomposable group in the structural unit (a1).

In the present invention, the component (J) contains a compound represented by general formula (J1) shown below (an ammonium salt; hereafter, this compound is sometimes referred to as "compound (J1)").

The compound (J1) is an ammonium salt having a fluorinated alkylsulfonate anion which is a strong acid. By virtue of the anion moiety being a strong acid, the compound (J1) exhibits acidity (proton donor ability) prior to exposure, and increases the solubility of the component (A) in an alkali developing solution.

On the other hand, by subjecting the component (J1) to exposure, a decomposition reaction involving decarboxylation proceeds, so that the bond between the nitrogen atom and the carbon atom of the carbonyl group is cleaved. As a result, an ammonium salt derived from a decomposition product $(H_2N^+(X^2)—X^1—Y—O-A-C(Q^1)(Q^2)—SO_3^-)$, carbon dioxide, a residual group derived from a decomposition product (a compound containing an aromatic ring having —NO and —C(Rx)=O bonded thereto and may have $R^1$ as a substituent, and an amine (WH) derived from the countercation. With respect to the ammonium salt derived from the decomposition product, after the generation thereof, in the molecules thereof or between the molecules, the proton on acidic portion is trapped by basic portion newly generated by photoexcitation decomposition and exhibiting a pKa larger than WH. As a result, the acidity becomes smaller than the ammonium salt compound (J1).

[Chemical Formula 45]

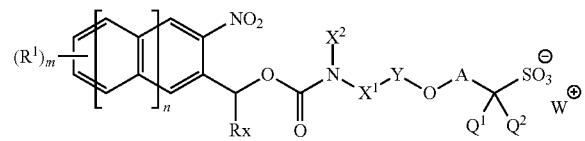

(J1)

In the formula, $R^1$ represents a hydrogen atom, a hydroxy group, a halogen atom, a linear or branched alkoxy group, a hydrocarbon group which may have a substituent, or a nitro group; m represents an integer of 0 to 4; n represents an integer of 0 to 3; Rx represents a hydrogen atom or a hydrocarbon group which may have a substituent; $X^1$ represents a divalent linking group and $X^2$ represents a hydrogen atom or a hydrocarbon group which may have a substituent, provided that $X^1$ and $X^2$ may be mutually bonded to form a ring with the nitrogen atom; Y represents a single bond or a carbonyl group, and A represents an alkylene group of 1 to 6 carbon atoms, provided that part of the methylene group constituting the alkylene group may be replaced with an oxygen atom or a carbonyl group, part or all of the hydrogen atoms constituting the alkylene group may be substituted with an aliphatic hydrocarbon group of 1 to 6 carbon atoms which may have a fluorine atom, and —Y—O-A- does not represent —C(=O)—O—C(=O)—; $Q^1$ and $Q^2$ each independently represents a fluorine atom or a linear or branched fluorinated alkyl group of 1 to 6 carbon atoms; and $W^+$ represents a primary, secondary or tertiary ammonium coutercation which exhibits a pKa smaller than a pKa of $H_2N^+(X^2)—X^1—Y—O-A-C(Q^1)(Q^2)—SO_3^-$ generated by decomposition upon exposure.

In formula (J1), $R^1$ represents a hydrogen atom, a hydroxy group, a halogen atom, a linear or branched alkoxy group, a hydrocarbon group which may have a substituent, or a nitro group.

Examples of the halogen atom for $R^1$ include a fluorine atom, a chlorine atom, a bromine atom and an iodine atom, and a fluorine atom is preferable.

As the linear or branched alkoxy group for $R^1$, an alkoxy group of 1 to 6 carbon atoms is preferable. Specific examples include a group in which an oxygen atom (—O—) is bonded to an alkyl group such as a methyl group, an ethyl group, a propyl group, an isopropyl group, an n-butyl group, an isobutyl group, a tert-butyl group, a pentyl group, an isopentyl group, a neopentyl group or a hexyl group. Among these, a methoxy group and an ethoxy group is preferable.

The hydrocarbon group of for $R^1$ which may have a substituent may be either an aromatic hydrocarbon group or an aliphatic hydrocarbon group.

The aromatic hydrocarbon group as the hydrocarbon group for $R^1$ is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 to 3, and most preferably 1 or 2.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used.

In the latter example, as the substituent for the aromatic hydrocarbon group, an alkyl group, an alkoxy group, a halogen atom, a halogenated alkyl group, a hydroxyl group, an oxygen atom (=O), a nitro group or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

As the alkoxy group and the halogen atom as the substituent for the aromatic hydrocarbon group, the same alkoxy groups and halogen atoms as those described above for $R^1$ can be mentioned.

Example of the halogenated alkyl group as the substituent for the aforementioned aromatic hydrocarbon group include groups in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

The aliphatic hydrocarbon group as the hydrocarbon group for $R^1$ may be either a saturated aliphatic hydrocarbon group, or an unsaturated aliphatic hydrocarbon group. Further, the aliphatic hydrocarbon group may be linear, branched or cyclic.

In the aliphatic hydrocarbon group, part of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom. As the "hetero atom", there is no particular limitation as long as it is an atom other than carbon atom and hydrogen, and examples thereof include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting part of the carbon atoms include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O), a cyano group and a nitro group. The alkoxy group, the halogen atom and the halogenated alkyl group as the substituent are the same as defined for the alkoxy group, the halogen atom and the halogenated alkyl group as the substituent for the aromatic hydrocarbon group.

As the aliphatic hydrocarbon group for the hydrocarbon group represented by $R^1$, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group as the hydrocarbon group for $R^1$ preferably has 2 to 10 carbon atoms, more preferably 2 to 5, still more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The cyclic aliphatic hydrocarbon group (aliphatic cyclic group) as the hydrocarbon group for $R^1$ is preferably an aliphatic cyclic group of 3 to 30 carbon atoms which may have a substituent.

The aliphatic cyclic group may be either a monocyclic group or a polycyclic group. The aliphatic cyclic group preferably has 5 to 30 carbon atoms, more preferably 5 to 20, still more preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L6) and (S1) to (S4) shown below.

[Chemical Formula 46]

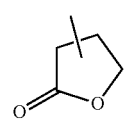

(L1)

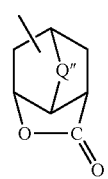

(L2)

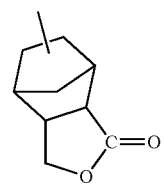

(L3)

-continued (L4) 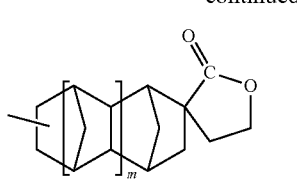

(L5) 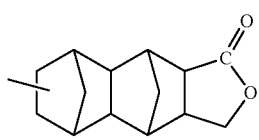

(L6) 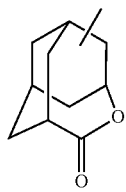

(S1) 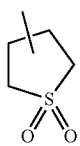

(S2) 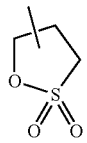

(S3) 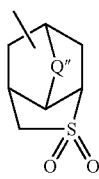

(S4) 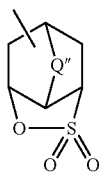

In the formula, Q" represents an alkylene group of 1 to 5 carbon atoms, —O—, —S—, —O—$R^{94}$— or —S—$R^{95}$— (wherein each of $R^{94}$ and $R^{95}$ independently represents an alkylene group of 1 to 5 carbon atoms); and m represents 0 or 1.

In the formulas, the alkylene group for Q" and $R^{94}$ to $R^{95}$ is preferably a linear or branched alkylene group, and has 1 to 5 carbon atoms, preferably 1 to 3.

Specific examples of alkylene groups include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH ($CH_3$)—, —C($CH_3$)$_2$$CH_2$— and —CH($CH_2CH_3$)$CH_2$—, and —CH($CH_2CH_1$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O). The alkyl group, the alkoxy group and the halogen atom as the substituent are the same as defined for the substituent for the aromatic hydrocarbon group.

Among these, as $R^1$, an alkoxy group, an aryl group or a nitro group is preferable, and particularly in terms of improvement in the decomposition efficiency during exposure, a nitro group is more preferable. It is preferable that the nitro group substitutes the hydrogen atom bonded to the carbon atom adjacent to the carbon atom having —CH(Rx)-O— bonded thereto (the ortho position of —CH(Rx)-O— in the case where n is 0 so that the ring is a benzene ring).

In formula (J1), m represents an integer of 0 to 4, preferably an integer of 0 to 2, more preferably 0 or 1, and most preferably 0. When m is 2 or more, the plurality of $R^1$ may be the same or different from each other.

In formula (J1), n represents an integer of 0 to 3. When n represents 0, it means that the aromatic ring in the formula is a benzene ring. n is preferably an integer of 0 to 2, more preferably 0 or 1, and most preferably 0.

In formula (J1), Rx represents a hydrogen atom or a hydrocarbon group which may have a substituent.

The hydrocarbon group for Rx which may have a substituent is the same as defined for the hydrocarbon group for $R^1$ which may have a substituent. The hydrocarbon group is preferably a chain-like aliphatic hydrocarbon group or an aromatic hydrocarbon group which may have a substituent, more preferably a chain-like alkyl group of 1 to 6 carbon atoms or an aromatic hydrocarbon group which may have a nitro group, and most preferably a methyl group or a phenyl group substituted with a nitro group (preferably substituted on the ortho position).

In formula (J1), $X^1$ represents a divalent linking group.

The divalent linking group for $X^1$ is not particularly limited, and is preferably a divalent hydrocarbon group which may have a substituent, a divalent linking group containing a hetero atom, —$X^{11}$—CH[N($X^{2'}$)$X^{1'}$—Y'—O-A'-C($Q^{1"}$)($Q^{2'}$)—$SO_3^-$]—$X^{12}$— or —$X^{11}$—CH[O-A'-C($Q^{1"}$)($Q^{2'}$)—$SO_3^-$]—$X^{12}$—.

The divalent hydrocarbon group which may have a substituent and the divalent linking group containing a hetero atom are the same as defined for those described above for $Y^2$ in the aforementioned formula (a1-0-2).

$X^{11}$ is a divalent hydrocarbon group which may have a substituent. As the divalent hydrocarbon group, the same groups as those described above for the "divalent hydrocarbon group which may have a substituent" for $Y^2$ in the aforementioned formula (a1-0-2) can be mentioned. As $X^{11}$, a linear aliphatic hydrocarbon group is preferable, more preferably a linear alkylene group, still more preferably a linear alkylene group of 1 to 5 carbon atoms, and a methylene group or an ethylene group is particularly desirable.

$X^{12}$ represents a single bond or a divalent hydrocarbon group which may have a substituent, and the divalent hydrocarbon group is the same as defined for the divalent hydrocarbon group represented by $X^{11}$. Among these, as $X^{12}$, a single bond is preferable.

$X^{1\prime}$, $X^{2\prime}$, $Y'$, $A'$, $Q^{1\prime}$ and $Q^{2\prime}$ are the same as defined for $X^1$, $X^2$, $Y$, $A$, $Q^1$ and $Q^2$.

By virtue of $X^1$ having —$X^{11}$—CH[N($X^{2\prime}$)$X^{1\prime}$—$Y'$—O-$A'$-C($Q^{1\prime}$)($Q^{2\prime}$)—$SO_3^-$]—$X^{12}$— or —$X^{11}$—CH[O-$A'$-C($Q^{1\prime}$)($Q^{2\prime}$)—$SO_3^-$]-$X^{12}$—, the acidity of the anion moiety of the compound (J1) can be increased.

Among these, as $X^1$, a linear or branched alkylene group, an aliphatic hydrocarbon group having a ring in the structure thereof, —$X^{11}$—CH[N($X^{2\prime}$)$X^{1\prime}$—$Y'$—O-$A'$-C($Q^1$)($Q^2$)—$SO_3^-$]—$X^{12}$— or —$X^{11}$—CH[O-$A'$-C($Q^1$)($Q^2$)—$SO_3^-$]—$X^{12}$— is preferable; and a linear or branched alkylene group of 1 to 6 carbon atoms is more preferable.

In formula (J1), $X^2$ represents a hydrogen atom or a hydrocarbon group which may have a substituent. The hydrocarbon group which may have a substituent is the same as defined for $R^1$.

As $X^2$, a hydrogen atom or an aliphatic hydrocarbon group which may have a substituent is preferable, and a hydrogen atom or a linear or branched alkyl group is more preferable.

In formula (J1), $X^1$ and $X^2$ may be mutually bonded to form a ring with the nitrogen atom. As the ring to be formed, a ring having 3 to 8 carbon atoms is preferable, and a ring having 4 to 6 carbon atoms is particularly desirable. Specific examples of the ring include an ethyleneimine ring, a pyrrolidine ring and a piperidine ring.

In formula (J1), Y represents a single bond or a carbonyl group. However, —Y—O-A- does not represent —C(=O)—O—C(=O)—. That is, when A (described later) has a carbonyl group on the terminal that comes into contact with the oxygen atom bonded to Y, Y does not represent a carbonyl group.

Further, when A does not have a carbonyl group, Y is preferably a carbonyl group.

In formula (J1), A represents an alkylene group of 1 to 6 carbon atoms, provided that part of the methylene group constituting the alkylene group may be replaced with an oxygen atom or a carbonyl group, part or all of the hydrogen atoms constituting the alkylene group may be substituted with an aliphatic hydrocarbon group of 1 to 6 carbon atoms which may have a fluorine atom. As the alkylene group for A, the same linear or branched alkylene groups as those described above for the divalent linking group represented by $Y^2$ can be mentioned.

Among these, as A, a methylene group or a carbonyl group is preferable.

In formula (J1), $Q^1$ and $Q^2$ each independently represents a fluorine atom or a linear or branched fluorinated alkyl group of 1 to 6 carbon atoms.

The fluorination ratio of the fluorinated alkyl group is preferably from 10 to 100%, more preferably from 50 to 100%, and it is most preferable that all hydrogen atoms are substituted with fluorine atoms because the acid strength increases. Specific examples of such fluorinated alkyl groups include a trifluoromethyl group, a heptafluoro-n-propyl group and a nonafluoro-n-butyl group.

Specific examples of preferable anion moieties for the compound (J1) are shown below.

[Chemical Formula 47]

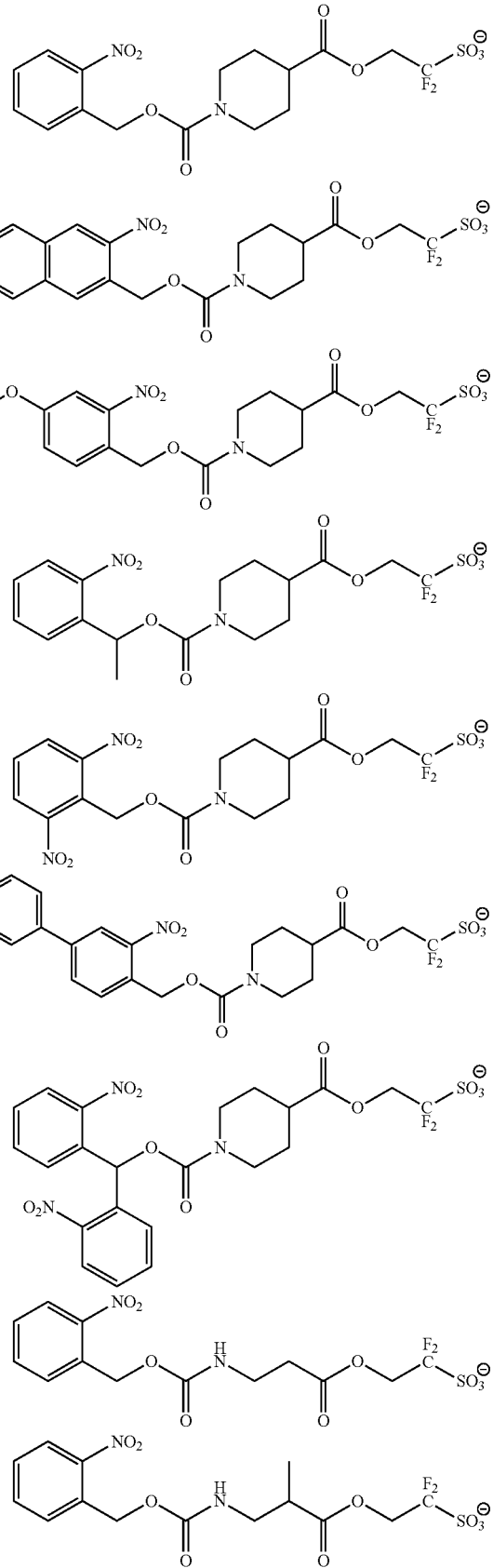

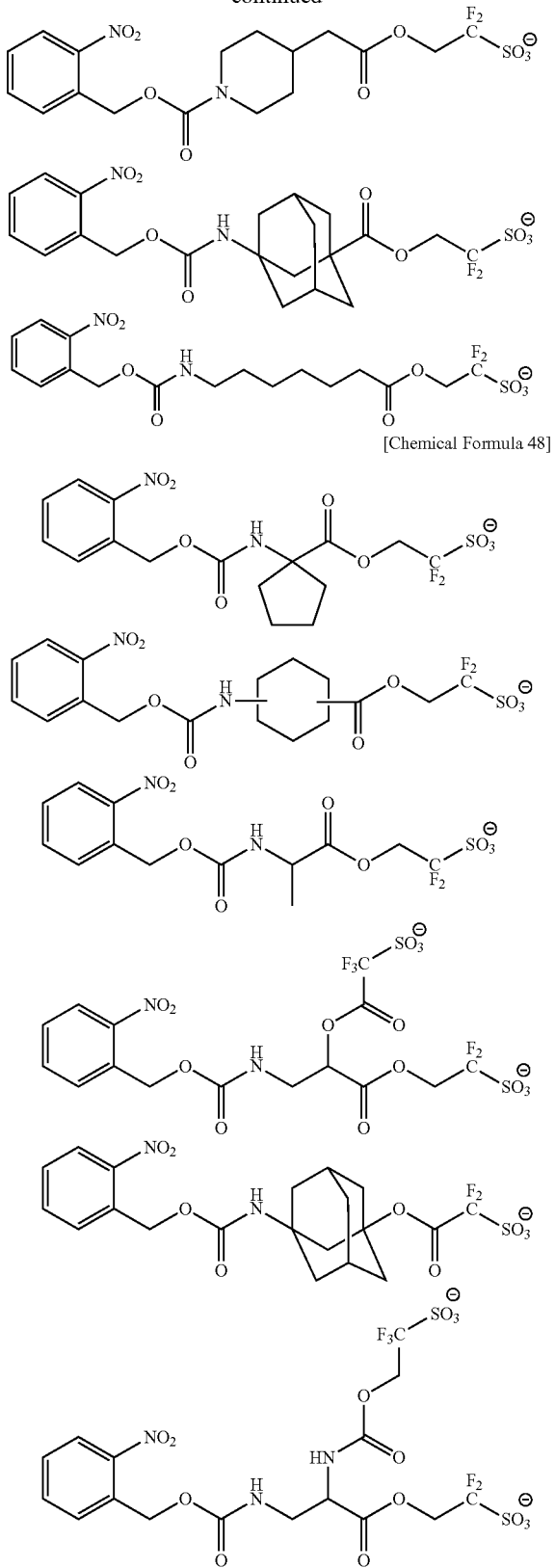

In formula (J1), W⁺ represents a primary, secondary or tertiary ammonium coutercation which exhibits a pKa smaller than a pKa of the ammonium salt derived from a decomposition product generated by decomposition upon exposure $(NH_2^+(X^2)—X^1—Y—O-A-C(Q^1)(Q^2)—SO_3^-)$.

As W⁺ in formula (J1), there is not particular limitation as long as it satisfies the above pKa, and can be appropriately selected depending on the type and pKa of anion moiety in formula (J1), type and pKa of the ammonium salt derived from a decomposition product, and the like. Specifically, W⁺ preferably has a pKa of 1 to 6. When the pKa is no more than 6, the basicity of the cation can be rendered satisfactorily weak, and the component (J) itself becomes an acidic compound prior to exposure. Further, the pKa can be rendered smaller than the pKa of the ammonium salt from a decomposition product. Further, when the pKa is at least 1, a salt can be more reliably formed with the counteranion prior to exposure, and it becomes possible to appropriately control the acidity of the component (J).

The structure of W⁺ is not particularly limited as long as it satisfies the above requirements and contains a nitrogen atom, and examples thereof include a cation represented by general formula (J1c-1) shown below.

[Chemical Formula 49]

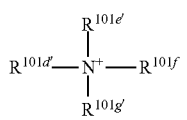

(J1c-1)

In the formula, $R^{101d\prime}$, $R^{101e\prime}$, $R^{101f\prime}$ and $R^{101g\prime}$ each independently represents a hydrogen atom, a linear, branched or cyclic alkyl group, an alkenyl group, an oxoalkyl group or an oxoalkenyl group of 1 to 12 carbon atoms, an aryl group of 6 to 20 carbon atoms, an aralkyl group of 7 to 12 carbon atoms, an aryloxoalkyl group, or a combination thereof, and part or all of the hydrogen atoms of these groups may be substituted with a fluorine atom, an alkoxy group or an amino group, and one or more —$CH_2$— within the alkyl group may be replaced with —NH—. $R^{101d\prime}$ and $R^{101e\prime}$, or $R^{101d\prime}$, $R^{101e\prime}$ and $R^{101f\prime}$ may be mutually bonded with the nitrogen atom to form a ring, provided that, when a ring is formed, each of $R^{101d\prime}$ and $R^{101e\prime}$, or each of $R^{101\prime}$, $R^{101e\prime}$ and $R^{101f\prime}$ independently represents an alkylene group of 3 to 10 carbon atoms, or forms a heterocyclic group containing the nitrogen atom in the ring thereof.

In formula (J1c-1), $R^{101d\prime}$, $R^{101e\prime}$, $R^{101f\prime}$ and $R^{101g\prime}$ independently represents a hydrogen atom, a linear, branched or cyclic alkyl group, an alkenyl group, an oxoalkyl group or an oxoalkenyl group of 1 to 12 carbon atoms, an aryl group or an arylalkyl group of 6 to 20 carbon atoms, an aralkyl group of 7 to 12 carbon atoms or an aryloxoalkyl group.

As the alkyl group for $R^{101d\prime}$ to $R^{101g\prime}$, the same alkyl groups as those described above for $R^1$ can be mentioned, preferably has 1 to 10 carbon atoms, and a methyl group, an ethyl group, a propyl group or a butyl group is particularly desirable.

The alkenyl group for $R^{101d\prime}$ to $R^{101g\prime}$ preferably has 2 to 10 carbon atoms, more preferably 2 to 5, and still more preferably 2 to 4. Specific examples thereof include a vinyl group, a propenyl group (an allyl group), a butynyl group, a 1-methylpropenyl group and a 2-methylpropenyl group.

The oxoalkyl group for $R^{101d\prime}$ to $R^{101g\prime}$ preferably has 2 to 10 carbon atoms, and examples thereof include a 2-oxoethyl group, a 2-oxopropyl group, a 2-oxocyclopentyl group and a 2-oxocyclohexyl group.

Examples of the oxoalkenyl group for $R^{101d'}$ to $R^{101g'}$ include an oxo-4-cyclohexenyl group and a 2-oxo-4-propenyl group.

As the aryl group for $R^{101d'}$ to $R^{101g'}$, the same aryl groups as those described above as the aromatic hydrocarbon group for $R^1$ can be mentioned, and a phenyl group or a naphthyl group is preferable.

Examples of the aralkyl group and aryloxoalkyl group for $R^{101d'}$ to $R^{101g'}$ include a benzyl group, a phenylethyl group, a phenethyl group, a 2-phenyl-2-oxoethyl group, a 2-(1-naphthyl)-2-oxoethyl group and a 2-(2-naphthyl)-2-oxoethyl group.

When $R^{101d'}$ to $R^{101g'}$ are constituted of only an alkyl group and/or a hydrogen atom, it is preferable that at least one of the hydrogen atoms or carbon atoms is substituted with a halogen atom such as a fluorine atom, an alkoxy group or a sulfur atom, and it is more preferable that a hydrogen atom within an alkyl group is substituted with a fluorine atom.

Further, $R^{101d}$ and $R^{101e}$, or $R^{101d}$, $R^{101e}$ and $R^{101f}$ may be mutually bonded to form a ring with the nitrogen atom. Examples of the formed ring include a pyrrolidine ring, a piperidine ring, a hexamethylene imine ring, an azole ring, a pyridine ring, a pyrimidine ring, an azepine ring, a pyrazine ring, a quinoline ring and a benzoquinoline ring.

Further, the ring may contain an oxygen atom in the ring skeleton thereof, and preferable examples of rings which contain an oxygen atom include an oxazole ring and an isooxazole ring.

As the cation moiety represented by general formula (J1c-1), cation moieties represented by general formulae (J1c-11) to (J1c-14) shown below are preferable.

[Chemical Formula 50]

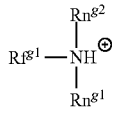
(J1c-11)

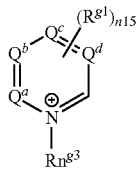
(J1c-12)

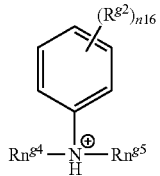
(J1c-13)

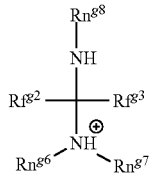
(J1c-14)

In the formulae, $Rf^{g1}$, $Rf^{g2}$ and $Rf^{g3}$ each independently represents a fluorinated alkyl group of 1 to 12 carbon atoms; $Rn^{g1}$ and $Rn^{g2}$ each independently represents a hydrogen atom, an alkyl group of 1 to 5 carbon atoms or a fluorinated alkyl group of 1 to 5 carbon atoms, provided that $Rn^{g1}$ and $Rn^{g2}$ may be mutually bonded to form a ring; $Q^a$ to $Q^d$ each independently represents a carbon atom or a nitrogen atom; $Rn^{g3}$ represents a hydrogen atom or a methyl group; $Rn^{g4}$, $Rn^{g5}$, $Rn^{g6}$, $Rn^{g7}$ and $Rn^{g8}$ each independently represents a hydrogen atom, an alkyl group of 1 to 5 carbon atoms or an aromatic hydrocarbon group; $R^{g1}$ and $R^{g2}$ each independently represents a hydrocarbon group; n15 and n16 each independently represents an integer of 0 to 4, provided that, when n15 and n16 is 2 or more, the plurality of $R^{g1}$ and $R^{g2}$ which substitute the hydrogen atoms of the adjacent carbon atom may be bonded to form a ring.

In formulae (J1c-11) and (J1c-14), $Rf^{g1}$ to $Rf^{g3}$ each independently represents a fluorinated alkyl group of 1 to 12 carbon atoms, and is preferably a fluorinated alkyl group of 1 to 5 carbon atoms in which 50% or more of the hydrogen atoms of the alkyl group have been fluorinated.

In formulae (J1c-13) and (J1c-14), $Rn^{g4}$ to $Rn^{g8}$ each independently represents an alkyl group of 1 to 5 carbon atoms or an aromatic hydrocarbon group, and is the same as defined for the alkyl group of 1 to 5 carbon atoms and aryl groups as those described above in the explanation of $R^{101d'}$, $R^{101e'}$, $R^{101f'}$ and $R^{101g'}$ in formula (J1c-1).

In formulae (J1c-12) and (J1c-13), n15 and n16 each independently represents an integer of 0 to 4, preferably an integer of 0 to 2, and more preferably 0.

In formulae (J1c-12) and (J1c-13), $R^{g1}$ and $R^{g2}$ each independently represents a hydrocarbon group, and is preferably an alkyl group or alkenyl group of 1 to 12 carbon atoms. The alkyl group and the alkenyl group are the same as defined for those described in the explanation of formula (J1c-1).

When n15 and n16 are 2 or more, the plurality of $R^{g1}$ and $R^{g2}$ may be the same or different from each other. Further, when n15 and n16 is 2 or more, the plurality of $R^{g1}$ and $R^{g2}$ which substitute the hydrogen atoms of the adjacent carbon atom may be bonded to form a ring. Examples of the formed ring include a benzene ring and a naphthalene ring. That is, the compound represented by formula (J1c-12) or (J1c-13) may be a condensed ring compound formed by condensation of 2 or more rings.

Specific examples of compounds represented by any one of the aforementioned formulae (J1c-11) to (J1c-14) are shown below.

[Chemical Formula 51]

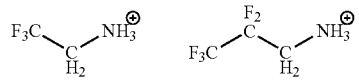

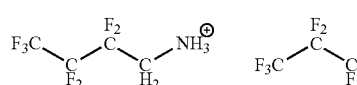

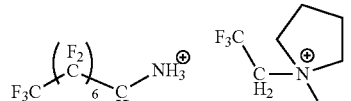

[Chemical Formula 52]

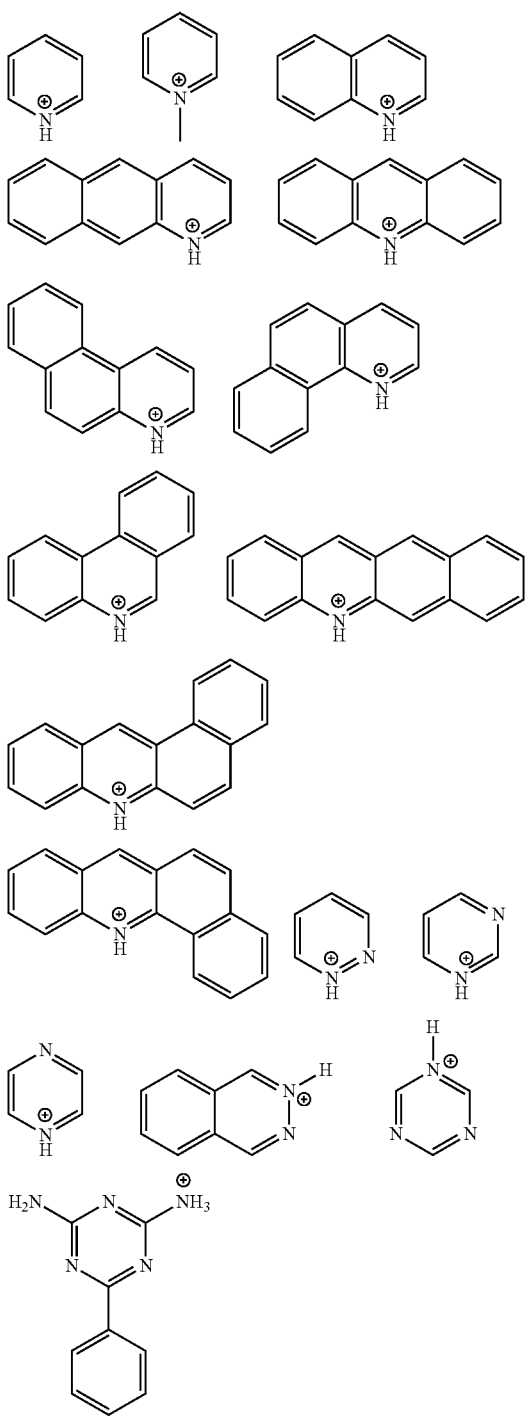

[Chemical Formula 53]

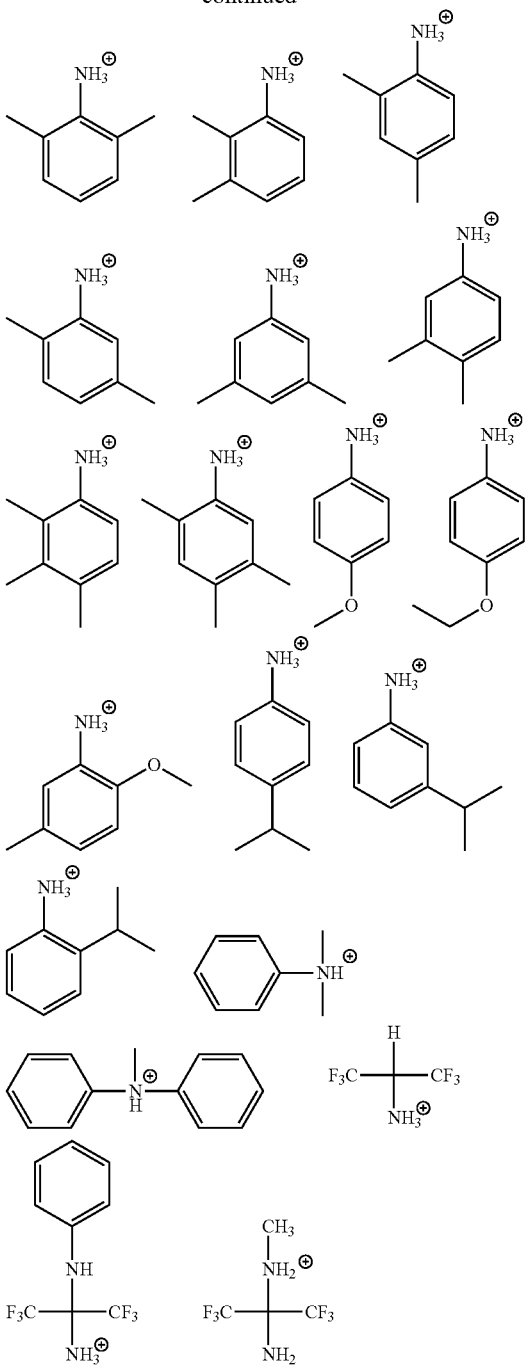

Further, $W^+$ may be a divalent cation. In the case where $W^+$ is a divalent cation, and only one $SO_3^-$ is present in the compound (J1), the molar ratio of the anion moiety:the cation moiety in the component (J) becomes 2:1. Likewise, in the case where $W^+$ is a monovalent cation as that represented by the aforementioned formula (J1c-1), and two $SO_3^-$ are present in the compound (J1) (the case where $X^1$ has $SO_3^-$), the molar ratio of the anion moiety: the cation moiety in the component (J) becomes 1:2.

Specific examples of the divalent ammonium cation include an ammonium cation represented by formula (J1c-2) shown below.

[Chemical Formula 54]

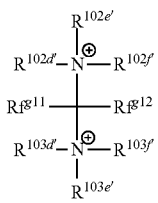

(J1c-2)

In the formula, $Rf^{g11}$ and $Rf^{g12}$ are the same as defined for $Rf^{g1}$ to $Rf^{g3}$; $R^{102d\prime}$, $R^{102e\prime}$, $R^{102f\prime}$, $R^{103d\prime}$, $R^{103e\prime}$ and $R^{103f\prime}$ are the same as defined for $R^{101d\prime}$ to $R^{101f\prime}$; $R^{102d\prime}$ and $R^{102e\prime}$, $R^{102e\prime}$ and $R^{102f\prime}$, $R^{103d\prime}$ and $R^{103e\prime}$, or $R^{103e\prime}$ and $R^{103f\prime}$ may be mutually bonded with the nitrogen atom to form a ring, provided that, when a ring is formed, each of $R^{102d\prime}$ and $R^{102e\prime}$, each of $R^{102e\prime}$ and $R^{102f\prime}$, each of $R^{103}d\prime$ and $R^{103e\prime}$, or each of $R^{103e\prime}$ and $R^{103f\prime}$ independently represents an alkylene group of 3 to 10 carbon atoms, or forms a heterocyclic group containing the nitrogen atom in the ring thereof.

A specific example of a compound represented by the formula (J1c-2) is shown below.

[Chemical Formula 55]

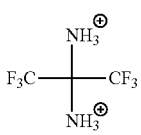

As the component (J), one type of compound may be used alone, or two or more types may be used in combination. Further, the component (J) may contain a component other than the compound (J1).

In the resist composition, the amount of the component (J), relative to 100 parts by weight of the component (A) is preferably from 0.5 to 30 parts by weight, more preferably from 1 to 20 parts by weight, and most preferably from 2 to 15 parts by weight. When the amount of the component (J) is within the above-mentioned range, the storage stability and the lithography properties become excellent.

<Photobase Generator Component; Component (C)>

The resist composition of the present invention may contain a component (C) which does not fall under the definition of the component (A) and the component (J). By virtue of the component (C) being decomposed during exposure by the exposure energy to generate a base, an excellent dissolution contrast can be obtained.

The component (C) may be any compound which does not fall under the definition of the component (A) and the component (J), and is capable of being decomposed by irradiation of radiation to generate a base, and examples thereof include a compound containing a carbamate group (a urethane bond), a compound containing an acyloxyimino group, an ionic compound (an anion-cation complex), and a compound containing a carbamoyloxyimino group. Among these, a compound containing a carbamate group (a urethane bond), a compound containing an acyloxyimino group, and an ionic compound (an anion-cation complex) are preferable.

Further, compounds having a ring structure within a molecule thereof are preferable, and examples thereof include compounds having a ring skeleton such as benzene, naphthalene, anthracene, xanthone, thioxanthone, anthraquinone or fluorene.

Among these, as the component (C), in terms of photodegradability, a compound represented by general formula (C1) shown below (hereafter, referred to as "component (C1)") is particularly desirable. When the compound is irradiated by radiation, at least the bond between the nitrogen atom in the formula (C1) and the carbon atom of the carbonyl group adjacent to the nitrogen atom is cleaved, thereby generating an amine or ammonia and carbon dioxide. After the decomposition, it is preferable that the product containing —$N(R^{01})(R^{02})$ has a high boiling point. Further, in terms of suppressing diffusion during post exposure bake (PEB), it is preferable that the product containing —$N(R^{01})(R^{02})$ has a large molecular weight or a highly bulky skeleton.

[Chemical Formula 56]

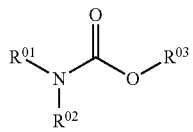

(C1)

In the formula, $R^{01}$ and $R^{02}$ each independently represents a hydrogen atom or a monovalent hydrocarbon group which may contain a hetero atom, provided that $R^{01}$ and $R^{02}$ may be mutually bonded to form a cyclic group with the adjacent nitrogen atom; and $R^{03}$ represents a monovalent photoactive group.

In formula (C1), the hetero atom which may be contained in the hydrocarbon group for $R^{01}$ and $R^{02}$ is an atom other than hydrogen and carbon, and examples thereof include an oxygen atom, a nitrogen atom, a sulfur atom and a halogen atom. Examples of the halogen atom include a fluorine atom, a chlorine atom, a bromine atom and an iodine atom.

The hydrocarbon group may be either an aromatic hydrocarbon group or an aliphatic hydrocarbon group, and is preferably an aliphatic hydrocarbon group.

In formula (C1), the aromatic hydrocarbon group for $R^{01}$ and $R^{02}$ is a hydrocarbon group having an aromatic ring.

The aromatic hydrocarbon group for $R^{01}$ and $R^{02}$ preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of the aromatic hydrocarbon group include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

Further, when the aromatic hydrocarbon group has an aliphatic hydrocarbon group bonded to the aromatic ring, part of the carbon atoms constituting the aliphatic hydrocarbon group may be substituted with a substituent group containing a hetero atom, or part or all of the hydrogen atoms constituting the aliphatic hydrocarbon group may be substituted with a substituent group. As examples of the "aliphatic hydrocarbon group" and the "divalent linking group containing a hetero atom", the same aliphatic hydrocarbon groups and divalent linking groups containing a hetero atom as those described later for $R^{01}$ and $R^{02}$ can be mentioned.

Examples of the aromatic hydrocarbon group in which part of the carbon atoms constituting the aromatic ring has been substituted with a hetero atom include a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom.

Examples of the substituent group which substitutes the hydrogen atom bonded to the aromatic ring of the aforementioned aromatic hydrocarbon group include an alkyl group, an alkoxy group, a halogen atom, a halogenated alkyl group, a hydroxyalkyl group, a hydroxy group, an oxygen atom (=O), —COOR", —OC(=O)R", a cyano group, a nitro group, —NR"$_2$, —$R^{9'}$—N($R^{10'}$)—C(=O)—O—$R^{5'}$, and a nitrogen-containing heterocyclic group.

The alkyl group for the substituent is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear or branched alkoxy group. Specific examples of the alkoxy group include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

The hydroxyalkyl group for the substituent preferably has 1 to 6 carbon atoms, and specific examples thereof include the aforementioned alkyl groups for the substituent in which at least one hydrogen atom has been substituted with a hydroxy group.

In the —COOR" group, the —OC(=O)R" group and the —NR"$_2$ group, R" represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The two R" groups within the —NR"$_2$ group may be the same or different from each other.

In formula —$R^{9'}$—N($R^{10'}$)—C(=O)—O—$R^{5'}$, $R^{9'}$ represents a divalent hydrocarbon group which may contain a hetero atom, $R^{10'}$ represents a hydrogen atom or a monovalent hydrocarbon group which may contain a hetero atom, and $R^{5'}$ represents a monovalent organic group which has an aliphatic ring or an aromatic ring.

Examples of the hydrocarbon group for $R^{9'}$ include groups in which one hydrogen atom has been removed from the hydrocarbon group for $R^{01}$ in the aforementioned formula (C1).

As examples of $R^{10'}$ and $R^{5'}$, the same groups as those described above for $R^{2}$ and $R^{3}$ in formula (C1) can be given, respectively.

In formula —$R^{9'}$—N($R^{10'}$)—C(=O)—O—$R^{5'}$, $R^{10'}$ may be bonded to $R^{9'}$ to form a ring.

With respect to $R^{01}$ and $R^{02}$ in formula (C1), when $R^{01}$ has —$R^{9'}$—N($R^{10'}$)—C(=O)—O—$R^{5'}$ as a substituent, $R^{10'}$ may be bonded to $R^{02}$ in formula (C1) to form a ring.

With respect to $R^{01}$ and $R^{02}$ in formula (C1), when $R^{01}$ has —$R^{9'}$—N($R^{10'}$)—C(=O)—O—$R^{5'}$ as a substituent, the compound represented by formula (C1) is preferably a compound represented by the following general formula: $R^{5'}$—O—C(=O)—N($R^{10'}$)—$R^{4}$—N($R^{2}$)—C(=O)—O—$R^{3}$ [in the formula, $R^{2}$, $R^{3}$, $R^{10'}$ and $R^{5'}$ are the same as defined above; and $R^{4}$ represents a divalent aliphatic hydrocarbon group].

Examples of the divalent aliphatic hydrocarbon group for $R^{4}$ include groups in which one hydrogen atom has been removed from the aliphatic hydrocarbon groups for $R^{01}$ and $R^{02}$ described later.

The "nitrogen-containing heterocyclic group" as the aforementioned substituent is a group in which one or more hydrogen atoms have been removed from a nitrogen-containing heterocyclic compound containing a nitrogen atom in the ring skeleton thereof. The nitrogen-containing heterocyclic compound may have a carbon atom or a hetero atom other than nitrogen (e.g., an oxygen atom, a sulfur atom or the like) within the ring skeleton thereof.

The nitrogen-containing heterocyclic compound may be either aromatic or aliphatic. When the nitrogen-containing heterocyclic compound is aliphatic, it may be either saturated or unsaturated. Further, the nitrogen-containing heterocyclic compound may be either monocyclic or polycyclic.

The nitrogen-containing heterocyclic compound preferably has 3 to 30 carbon atoms, more preferably 5 to 30, and still more preferably 5 to 20.

Specific examples of monocyclic nitrogen-containing heterocyclic compound include pyrrole, pyridine, imidazole, pyrazole, 1,2,3-triazole, 1,2,4-triazole, pyrimidine, pyrazine, 1,3,5-triazine, tetrazole, piperidine, piperazine, pyrrolidine and morpholine.

Specific examples of polycyclic nitrogen-containing heterocyclic compound include quinoline, isoquinoline, indole, pyrrolo[2,3-b]pyridine, indazole, benzimidazole, benzotriazole, carbazole, acridine, 1,5-diazabicyclo[4.3.0]-5-nonene, 1,8-diazabicyclo[5.4.0]-7-undecene, hexamethylenetetramine and 1,4-diazabicyclo[2.2.2]octane.

The nitrogen-containing heterocyclic compound may have a substituent. Examples of the substituent include the same groups as those described above for the substituent group which substitutes a hydrogen atom bonded to the aromatic ring contained in the aforementioned aromatic hydrocarbon group.

In formula (C1), the aliphatic hydrocarbon group for $R^{01}$ and $R^{02}$ refers to a hydrocarbon group that has no aromaticity.

The aliphatic hydrocarbon group for $R^{01}$ and $R^{02}$ may be either saturated (an alkyl group) or unsaturated. In general, the aliphatic hydrocarbon group is preferably saturated. Further, the aliphatic hydrocarbon group may be linear, branched or cyclic, or a combination thereof. Examples of the combination include a group in which a cyclic aliphatic hydrocarbon group is bonded to a terminal of a linear or branched aliphatic hydrocarbon group, and a group in which a cyclic aliphatic hydrocarbon group is interposed within a linear or branched aliphatic hydrocarbon group.

The linear or branched alkyl group preferably has 1 to 20 carbon atoms, more preferably 1 to 15, and still more preferably 1 to 10.

Specific examples of linear alkyl groups include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

Specific examples of branched alkyl groups include a 1-methylethyl group (an isopropyl group), a 1-methylpropyl group, a 2-methylpropyl group, a 1-methylbutyl group, a 2-methylbutyl group, a 3-methylbutyl group, a 1-ethylbutyl group, a 2-ethylbutyl group, a tert-butyl group, a 1-methylpentyl group, a 2-methylpentyl group, a 3-methylpentyl group and a 4-methylpentyl group.

The cyclic alkyl group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12. As the aliphatic cyclic group, a group in which one hydrogen atom has been removed from a monocycloalkane or a polycycloalkane such as a bicycloalkane, tricycloalkane or tetracycloalkane can be used. Specific examples of the group in which one hydrogen atom has been removed from a monocycloalkane include a cyclopentyl group and a cyclohexyl group. Examples of the group in which one hydrogen atom has been removed from a polycycloalkane include an adamantyl group, a norbornyl group, an isobornyl group, a tricyclodecyl group and a tetracyclododecyl group.

The aliphatic hydrocarbon group may have a substituent. For example, part of the carbon atoms constituting the aliphatic hydrocarbon group may be replaced by a divalent linking group containing a hetero atom, and part or all of the hydrogen atoms constituting the aliphatic hydrocarbon group may be substituted with a substituent.

With respect to the divalent linking group containing a hetero atom, examples of hetero atoms include the same hetero atoms as those described above which replaces part of the carbon atoms constituting the aromatic ring contained in the aforementioned aromatic hydrocarbon group. Examples of the divalent linking group containing a hetero atom include divalent non-hydrocarbon groups containing a hetero atom, such as —O—, —C(=O)—, —C(=O)—O—, a carbonate bond (—O—C(=O)—O—), —S—, —S(=O)$_2$—, —S(=O)$_2$—O—, —NH—, —NR$^{04}$— (R$^{04}$ represents a substituent such as an alkyl group or an acyl group), —NH—C(=O)— and =N—. Further, a combination of any one of these "non-hydrocarbon groups containing a hetero atom" with a divalent aliphatic hydrocarbon group can also be used. Examples of the divalent aliphatic hydrocarbon group include groups in which one hydrogen atom has been removed from the aforementioned aliphatic hydrocarbon group, and a linear or branched aliphatic hydrocarbon group is preferable.

As the substituent for the aliphatic hydrocarbon group in the latter example, the same groups as those described above for the substituent group which substitutes a hydrogen atom bonded to the aromatic ring contained in the aforementioned aromatic hydrocarbon group can be mentioned.

In the aforementioned general formula (C1), $R^{01}$ and $R^{02}$ may be mutually bonded to form a cyclic group with the adjacent nitrogen atom.

The cyclic group may be either an aromatic cyclic group or an aliphatic cyclic group. When the cyclic group is an aliphatic cyclic group, it may be either saturated or unsaturated. In general, the aliphatic cyclic group is preferably saturated.

The cyclic group may have a nitrogen atom other than the nitrogen atom bonded to $R^{01}$ and $R^{02}$ within the ring skeleton thereof. Further, the cyclic group may have a carbon atom or a hetero atom other than nitrogen (e.g., an oxygen atom, a sulfur atom or the like) within the ring skeleton thereof.

The cyclic group may be either a monocyclic group or a polycyclic group.

When the cyclic group is monocyclic, the number of atoms constituting the skeleton of the cyclic group is preferably from 4 to 7, and more preferably 5 or 6. That is, the cyclic group is preferably a 4- to 7-membered ring, and more preferably a 5- or 6-membered ring. Specific examples of monocyclic groups include groups in which the hydrogen atom of —NH— has been removed from a heteromonocyclic group containing —NH— in the ring structure thereof, such as piperidine, pyrrolidine, morpholine, pyrrole, imidazole, pyrazole, 1,2,3-triazole, 1,2,4-triazole, tetrazole or piperazine.

When the cyclic group is polycyclic, the cyclic group is preferably bicyclic, tricyclic or tetracyclic. Further, the number of atoms constituting the skeleton of the cyclic group is preferably from 7 to 12, and more preferably from 7 to 10. Specific examples of polycyclic nitrogen-containing heterocyclic groups include groups in which the hydrogen atom of —NH— has been removed from a heteropolycyclic group containing —NH— in the ring structure thereof, such as indole, isoindole, carbazole, benzimidazole, indazole or benzotriazole.

The cyclic group may have a substituent. Examples of the substituent include the same groups as those described above for the substituent group which substitutes a hydrogen atom bonded to the aromatic ring contained in the aforementioned aromatic hydrocarbon group.

As a cyclic group formed by $R^{01}$ and $R^{02}$ mutually bonded with the adjacent nitrogen atom, a group represented by general formula (II) shown below is particularly desirable.

[Chemical Formula 57]

(II)

In the formula, $R^{05}$ and $R^{06}$ each independently represents a hydrogen atom or an alkyl group; $R^{07}$ represents a linear alkylene group of 1 to 3 carbon atoms which may have a carbon atom substituted with an oxygen atom or a nitrogen atom and may have a hydrogen atom substituted with a substituent.

In formula (II), as the alkyl group for $R^{05}$ and $R^{06}$, the same alkyl groups as those described above as the aliphatic hydrocarbon group for $R^{01}$ and $R^{02}$ can be mentioned, a linear or branched alkyl group is preferable, and a methyl group is particularly desirable.

Examples of the alkylene group for $R^{07}$ which may have a carbon atom substituted with an oxygen atom or a nitrogen atom include —$CH_2$—, —$CH_2$—O—, —$CH_2$—NH—, —$CH_2$—$CH_2$—, —$CH_2$—O—$CH_2$—, —$CH_2$—NH—$CH_2$—, —$CH_2$—$CH_2$—$CH_2$—, —$CH_2$—$CH_2$—O—$CH_2$—, and —$CH_2$—$CH_2$—NH—$CH_2$—.

As the substituent which substitutes a hydrogen atom in the alkylene group, the same groups as those described above for the substituent group which substitutes a hydrogen atom bonded to the aromatic ring contained in the aforementioned aromatic hydrocarbon group can be mentioned. The hydrogen atom to be substituted with a substituent may be a hydrogen atom bonded to a carbon atom, or a hydrogen atom bonded to a nitrogen atom.

In formula (C1), $R^{03}$ represents a monovalent photoactive group.

The term "photoactive group" refers to a group which absorbs the exposure energy of the exposure.

As the photoactive group, a ring-containing group is preferable, and may be either a hydrocarbon ring or a hetero ring. Preferable examples thereof include groups having a ring structure described above for $R^{01}$ and $R^{02}$, and groups having an aromatic ring. Specific examples of preferable ring skeletons for the ring-containing group include benzene, biphenyl, indene, naphthalene, fluorene, anthracene, phenanthrene, xanthone, thioxanthone and anthraquinone.

Further, these ring skeletons may have a substituent. In terms of efficiency in the generation of a base, as the substituent, a nitro group is particularly desirable.

As the component (C1), a compound represented by general formula (C1-11) or (C1-12) shown below is particularly desirable.

[Chemical Formula 58]

(C1-11)

(C1-12)

In the formulae, $R^{4a}$ and $R^{4b}$ each independently represents a ring skeleton selected from benzene, biphenyl, indene, naphthalene, fluorene, anthracene, phenanthrene, xanthone, thioxanthone and anthraquinone which may have a substituent; $R^{1a}$ and $R^{2a}$ each independently represents an alkyl group of 1 to 15 carbon atoms or a cycloalkyl group; $R^{11a}$ represents an alkyl group of 1 to 5 carbon atoms; m" represents 0 or 1; n" represents 0 to 3; and each p" independently represents 0 to 3.

In formulae (C1-11) and (C1-12), in terms of efficiency in generation of a base, it is preferable that $R^{4a}$ and $R^{4b}$ has a nitro group as a substituent, and it is particularly desirable that the ortho position is substituted.

In terms of suppressing the diffusion length of the generated base, it is preferable that each of $R^{1a}$ and $R^{2a}$ is a cycloalkyl group of 5 to 10 carbon atoms.

m" is preferably 1. n" is preferably 0 to 2. p" is preferably 0 or 1.

Specific examples of the component (C1) are shown below.

[Chemical Formula 59]

(C1-11-1)

(C1-11-2)

(C1-11-3)

(C1-11-4)

(C1-11-5)

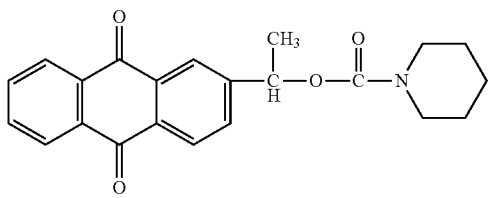

[Chemical Formula 60]

(C1-12-1)

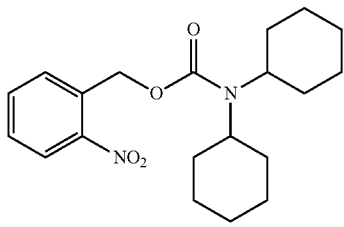

(C1-12-2)

(C1-12-3)

(C1-12-4)

Further, as a preferable example of the component (C), a compound represented by general formula (C2) shown below (hereafter, referred to as "component (C2)") can also be mentioned.

After absorbing the exposure energy by the exposure conducted in step (2), the component (C2) has the (—CH=CH—C(=O)—) portion isomerized to a cis isomer, and is further cyclized by heating, thereby generating a base ($NHR^1R^2$).

The component (C2) is preferable in that, not only a base can be generated, but also the effect of rendering the resist composition hardly soluble in an alkali developing solution in step (4) can be obtained.

[Chemical Formula 61]

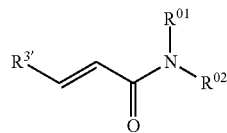

(C2)

In formula (C2), $R^{01}$ and $R^{02}$ are respectively the same as defined for $R^{01}$ and $R^{02}$ in the aforementioned formula (C1); and $R^{3'}$ represents an aromatic cyclic group having a hydroxy group on the ortho position.

In the aforementioned formula (C2), it is preferable that $R^{01}$ and $R^{02}$ are mutually bonded together with the adjacent nitrogen atom to form a cyclic group represented by the aforementioned formula (II). Further, $R^{01}$ and $R^{02}$ are preferably the same as defined for $R^{1a}$ and $R^{2a}$ in the aforementioned formula (C1-12).

As the aromatic cyclic group for $R^{3'}$, the same groups having an aromatic ring as those described above for $R^{03}$ in the aforementioned formula (C1) can be mentioned. As the ring skeleton, benzene, biphenyl, indene, naphthalene, fluorene, anthracene and phenanthrene are preferable, and a benzene ring is more preferable.

The aromatic cyclic group for $R^{3'}$ may have a substituent other than the hydroxy group on the ortho position. Examples of the substituent include a halogen atom, a hydroxy group, a mercapto group, a sulfide group, a silyl group, a silanol group, a nitro group, a nitroso group, a sulfino group, a sulfo group, a sulfonate group, a phosphino group, a phosphinyl group, a phosphono group, a phosphonate group, an amino group, an ammonio group, and a monovalent organic group such as an alkyl group.

Specific examples of the component (C2) are shown below.

[Chemical Formula 62]

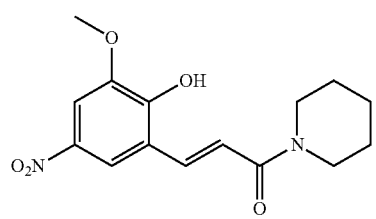

(C2-1)

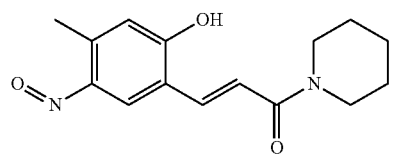

(C2-2)

Further, as a preferable example of the component (C), a compound represented by general formula (C3) shown below (hereafter, referred to as "component (C3)") can also be mentioned.

After absorbing the exposure energy by the exposure conducted in step (2), the component (C3) undergoes decarboxylation, and then reacts with water to generate amine (base).

[Chemical Formula 63]

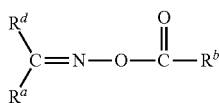

(C3)

In the formula, $R^a$ and $R^d$ each independently represents a hydrogen atom or a hydrocarbon group of 1 to 30 carbon atoms which may have a substituent (provided that, when both $R^a$ and $R^d$ represent a hydrocarbon group of 1 to 30 carbon atoms which may have a substituent, $R^a$ and $R^d$ are mutually bonded to form a ring); and $R^b$ represents an aryl group which may have a substituent or an aliphatic cyclic group which may have a substituent.

In the aforementioned formula (C3), $R^a$ represents a hydrogen atom or a hydrocarbon group of 1 to 30 carbon atoms which may have a substituent.

The hydrocarbon group of 1 to 30 carbon atoms for $R^a$ which may have a substituent is the same as defined for the hydrocarbon group of 1 to 30 carbon atoms represented by $R^1$ in the aforementioned formula (J1) which may have a substituent.

As the aliphatic cyclic group for $R^a$ which may have a substituent, an aliphatic polycyclic group which may have a substituent is preferable. As the aliphatic polycyclic group, the aforementioned group in which one or more hydrogen atoms have been removed from a polycycloalkane, and groups represented by formulas (L2) to (L6), (S3) and (S4) are preferable.

When $R^a$ in the aforementioned formula (C3) represents a hydrocarbon group of 1 to 30 carbon atoms which may have a substituent, $R^a$ may form a ring with the adjacent carbon atom. The formed ring may be either monocyclic or polycyclic. The number of carbon atoms (including the carbon atom bonded thereto) is preferably 5 to 30, and more preferably 5 to 20.

Specifically, among the cyclic aliphatic hydrocarbon groups (aliphatic cyclic groups) for $R^a$ described above, aliphatic cyclic groups of 5 to 30 carbon atoms can be given as examples (provided that the carbon atom bonded thereto is regarded as part of the ring).

It is preferable that $R^a$ in the aforementioned formula (C3) is a hydrogen atom or a cyclic group which may have a substituent. The cyclic group may be either an aromatic hydrocarbon group which may have a substituent, or an aliphatic cyclic group which may have a substituent.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by formulas (L2) to (L6), (S3) and (S4) are preferable.

As the aromatic hydrocarbon group which may have a substituent, a naphthyl group which may have a substituent, or a phenyl group which may have a substituent is preferable.

Examples of the aryl group for $R^b$ in the aforementioned formula (C3) include the aromatic hydrocarbon groups described above for $R^a$, excluding arylalkyl groups. As the aryl group for $R^b$, a phenyl group is more preferable.

The aliphatic cyclic group for $R^b$ in the aforementioned formula (C3) is the same as defined for the aliphatic cyclic group for $R^a$ in the aforementioned formula (C3). The aliphatic cyclic group for $R^b$ is preferably an aliphatic polycyclic group, more preferably a group in which one or more hydrogen atoms have been removed from a polycycloalkane, and most preferably a group in which one or more hydrogen atoms have been removed from adamantane.

As the substituent which the aromatic hydrocarbon group or the aliphatic cyclic group for $R^b$ may have, the same substituents as those described above for $R^a$ in the aforementioned formula (C3) can be mentioned.

$R^d$ in the aforementioned formula (C3) is the same as defined for $R^a$ in the aforementioned formula (C3).

It is preferable that $R^d$ in the aforementioned formula (C3) is a cyclic group which may have a substituent.

The cyclic group may be either an aromatic hydrocarbon group which may have a substituent, or an aliphatic cyclic group which may have a substituent, and an aromatic cyclic group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by formulas (L2) to (L6), (S3) and (S4) are preferable.

$R^d$ in the aforementioned formula (C3) is more preferably a naphthyl group which may have a substituent, or a phenyl group which may have a substituent, and most preferably a phenyl group which may have a substituent.

When both $R^a$ and $R^d$ represent a hydrocarbon group of 1 to 30 carbon atoms which may have a substituent, $R^a$ and $R^d$ are mutually bonded to form a ring. The formed ring may be either monocyclic or polycyclic. The number of carbon atoms (including the carbon atom bonded to $R^a$ and $R^d$ in the aforementioned formula (C3) is preferably 5 to 30, and more preferably 5 to 20.

Specifically, among the cyclic aliphatic hydrocarbon groups (aliphatic cyclic groups) for $R^a$ described above, aliphatic cyclic groups of 5 to 30 carbon atoms can be given as examples, provided that the carbon atom bonded to $R^a$ and $R^d$ is regarded as part of the ring.

Specific examples of the component (C3) are shown below.

[Chemical Formula 64]

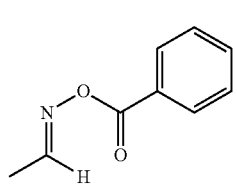

(C3-1)

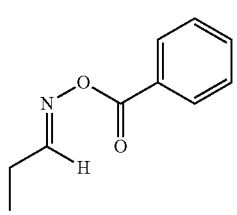

(C3-2)

-continued
(C3-3)
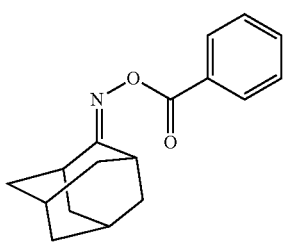
(C3-4)
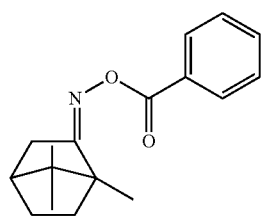
(C3-5)
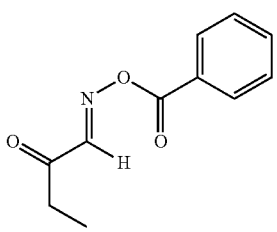
(C3-6)
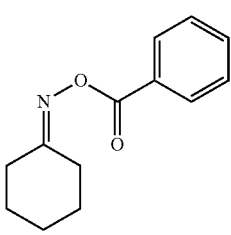
(C3-7)
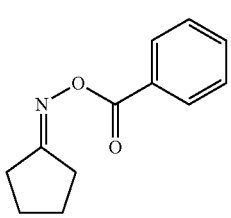
(C3-8)
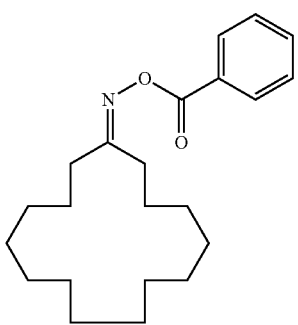
-continued
(C3-9)
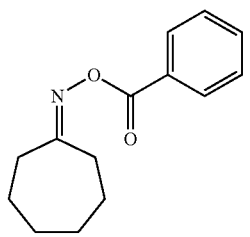
(C3-10)
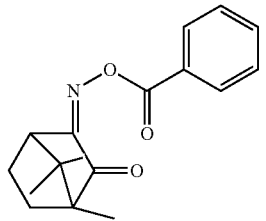
[Chemical Formula 65]
(C3-11)
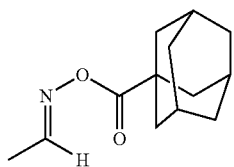
(C3-12)
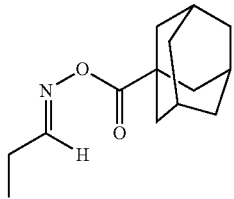
(C3-13)
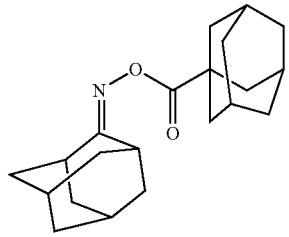
(C3-14)
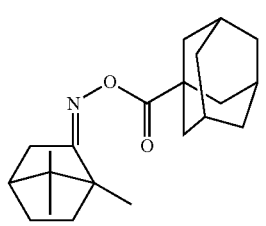
(C3-15)
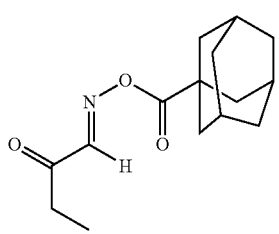

-continued (C3-16)

(C3-17)

(C3-18)

(C3-19)

(C3-20)

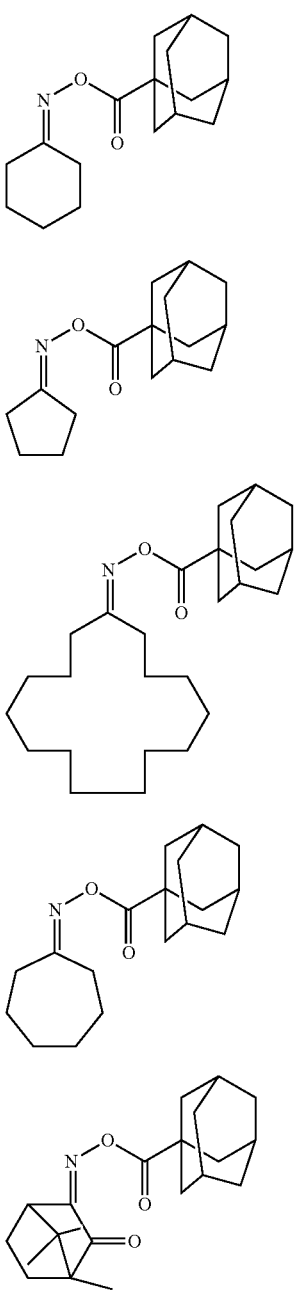

Further, as a preferable example of the component (C), the following compounds (C4) containing an acyloxyimino group can also be mentioned.

[Chemical Formula 66]

(C4-1)

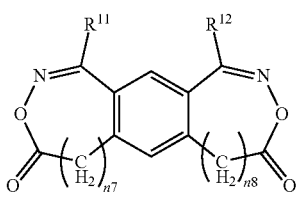

-continued (C4-2)

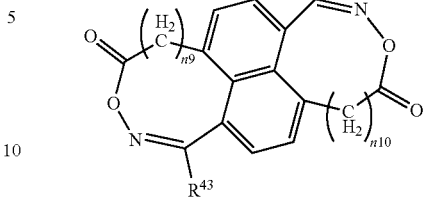

In the formulae, $R^{11}$, $R^{12}$, $R^{43}$ and $R^{44}$ each independently represents a hydrogen atom or an alkyl group of 1 to 5 carbon atoms; and n7 to n10 each independently represents 0 to 3.

Furthermore, as the component (C), other than the above examples, any of the known photo-base generators used in conventional chemically amplified resist compositions can be used.

Examples of such photo-base generators include ion-type photo-base generators (anion-cation complexes); triphenylsulfonium compounds; triphenylmethanol; photoactive carbamates, such as benzylcarbamate and benzoin carbamate; amides, such as o-carbamoylhydroxylamide, o-carbamoyloxime, aromatic sulfoneamide, alphalactum and N-(2-allylethynyl)amide; oximeesters; α-aminoacetophenone; cobalt complexes; and those exemplified in Japanese Unexamined Patent Application, First Publication No. 2007-279493.

As the component (C), one type of organic compound may be used alone, or two or more types of organic compounds may be used in combination.

Among the above examples, as the component (C), a component (C1) is preferable, and at least one member selected from the group consisting of compounds represented by the aforementioned general formula (C1-11) or (C1-12) is more preferable.

In the resist composition, the amount of the component (C), relative to 100 parts by weight of the component (A) is preferably from 0.05 to 50 parts by weight, more preferably from 1 to 30 parts by weight, and most preferably from 5 to 20 parts by weight. When the amount of the component (C) is at least as large as the lower limit of the above-mentioned range, the film retentiveness of the resist film at exposed portions becomes excellent, and the effects of the present invention are improved. On the other hand, when the amount of the component (C) is no more than the upper limit of the above-mentioned range, the transparency of the resist film can be maintained.

<Component (G); Acidic Compound Component>

The resist composition of the present invention may further contain an acidic compound component (G) which does not fall under the definition of the component (A), the component (J) and the component (C).

In the present invention, as the component (G), there is no particular limitation as long as it does not fall under the definition of the component (A), the component (J) and the component (C).

In the present invention, as the component (G), an acidic salt having an acid strength sufficient for increasing the solubility of the component (A) in an alkali developing solution, and is not decomposed by exposure to exhibit decreased acid strength (hereafter, referred to as "component (G1)") or an acid other than acid salts, and is not decomposed by exposure to exhibit decreased acid strength (acids which do not form a salt, acids which are not ionic; hereafter, referred to as "component (G2)") can be used.

[Component (G1)]

Examples of the component (G1) include an ionic compound (salt compound) having a nitrogen-containing cation and a counteranion. The component (G1) itself exhibits acidity even in the form of a salt, and acts as a proton donor.

Hereafter, the cation moiety and the anion moiety of the component (G1) will be described.

(Cation Moiety of Component (G1))

The cation moiety of the component (G1) is not particularly limited as long as it contains a nitrogen atom, and is the same as defined for the cation moiety of the component (J1) described above.

(Anion Moiety of Component (G1))

The anion moiety of the component (G1) is not particularly limited, and any of those generally used the anion moiety of a salt used in a resist composition, and is not decomposed by exposure to exhibit decreased acid strength may be appropriately selected for use.

Among these, as the anion moiety of the component (G1), those which forms a salt with the cation moiety to form a component (G1) that is capable of increasing the solubility of the component (A) in an alkali developing solution is preferable.

That is, the anion moiety of the component (G1) preferably has a strong acidity. Specifically, the pKa of the anion moiety is more preferably 0 or less, still more preferably −15 to −1, and most preferably −13 to −3. When the pKa of the anion moiety is no more than 0, the acidity of the anion can be rendered satisfactorily strong relative to a cation having a pKa of 7 or less, and the component (G1) itself becomes an acidic compound. On the other hand, when the pKa of the anion moiety is −15 or more, deterioration of the storage stability caused by the component (G1) being excessively acidic can be prevented.

As the anion moiety of the component (G1), an anion moiety having at least one anion group selected from a sulfonate anion, a carboxylate anion, a sulfonylimide anion, a bis(alkylsulfonyl)imide anion and a tris(alkylsulfonyl)methide anion is preferable.

Specific examples include anions represented by general formula: "$R^{4"}SO_3^-$ ($R^{4"}$ represents a linear, branched or cyclic alkyl group which may have a substituent, a halogenated alkyl group, an aryl group or an alkenyl group)".

In the aforementioned general formula "$R^{4"}SO_3^-$", $R^{4"}$ represents a linear, branched or cyclic alkyl group which may have a substituent, a halogenated alkyl group, an aryl group or an alkenyl group.

The linear or branched alkyl group for the aforementioned $R^{4"}$ preferably has 1 to 10 carbon atoms, more preferably 1 to 8, and most preferably 1 to 4.

The cyclic alkyl group for the aforementioned $R^{4"}$ preferably has 4 to 15 carbon atoms, more preferably 4 to 10 carbon atoms, and most preferably 6 to 10 carbon atoms.

When $R^{4"}$ represents an alkyl group, examples of "$R^{41}SO_3^-$" include alkylsulfonates, such as methanesulfonate, n-propanesulfonate, n-butanesulfonate, n-octanesulfonate, 1-adamantanesulfonate, 2-norbornanesulfonate and d-camphor-10-sulfonate.

The halogenated alkyl group for the aforementioned $R^{4"}$ is an alkyl group in which part or all of the hydrogen atoms thereof have been substituted with a halogen atom. The alkyl group preferably has 1 to 5 carbon atoms, and is preferably a linear or branched alkyl group, and more preferably a methyl group, an ethyl group, a propyl group, an isopropyl group, an n-butyl group, a tert-butyl group, a tert-pentyl group or an isopentyl group. Examples of the halogen atom which substitutes the hydrogen atoms include a fluorine atom, a chlorine atom, an iodine atom and a bromine atom.

In the halogenated alkyl group, it is preferable that 50 to 100% of all hydrogen atoms within the alkyl group (prior to halogenation) have been substituted with a halogen atom, and it is preferable that all hydrogen atoms have been substituted with a halogen atom.

As the halogenated alkyl group, a fluorinated alkyl group is preferable. The fluorinated alkyl group preferably has 1 to 10 carbon atoms, more preferably 1 to 8 carbon atoms, and most preferably 1 to 4 carbon atoms.

Further, the fluorination ratio of the fluorinated alkyl group is preferably from to 100%, more preferably from 50 to 100%, and it is most preferable that all hydrogen atoms are substituted with fluorine atoms because the acid strength increases.

Specific examples of such fluorinated alkyl groups include a trifluoromethyl group, a heptafluoro-n-propyl group and a nonafluoro-n-butyl group.

The aryl group for $R^{4"}$ is preferably an aryl group of 6 to 20 carbon atoms.

The alkenyl group for $R^{4"}$ is preferably an alkenyl group of 2 to 10 carbon atoms.

With respect to $R^{4"}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4"}$ may have one substituent, or two or more substituents.

Examples of the substituent include a halogen atom, a hetero atom, an alkyl group, and a group represented by the formula $X^3$-Q'- (in the formula, Q' represents a divalent linking group containing an oxygen atom; and $X^3$ represents a hydrocarbon group of 3 to 30 carbon atoms which may have a substituent).

Examples of halogen atoms and alkyl groups include the same halogen atoms and alkyl groups as those described above with respect to the halogenated alkyl group for $R^{4"}$.

Examples of hetero atoms include an oxygen atom, a nitrogen atom, and a sulfur atom.

In the group represented by formula $X^3$-Q'-, Q' represents a divalent linking group containing an oxygen atom.

Q' may contain an atom other than an oxygen atom. Examples of atoms other than oxygen include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an amido bond (—C(=O)—NH—), a carbonyl group (—C(=O)—) and a carbonate bond (—O—C(=O)—O—); and combinations of the aforementioned non-hydrocarbon, hetero atom-containing linking groups with an alkylene group. Furthermore, the combinations may have a sulfonyl group (—$SO_2$—) bonded thereto.

Specific examples of such combinations include —$R^{91}$—O—, —$R^{92}$—O—C(=O)—, —C(=O)—O—$R^{93}$—O—C(=O)—, —$SO_2$—O—$R^{94}$—O—C(=O)—, and —$R^{95}$—$SO_2$—O—$R^{94}$—O—C(=O)— (in the formula, $R^{91}$ to $R^{95}$ independently represents an alkylene group).

The alkylene group for $R^{91}$ to $R^{95}$ is preferably a linear or branched alkylene group, and preferably has 1 to 12 carbon atoms, more preferably 1 to 5, and most preferably 1 to 3.

Specific examples of alkylene groups include a methylene group [—$CH_2$—]; alkylmethylene groups such as —CH($CH_3$)—, —CH($CH_2CH_3$)—, —C($CH_3$)$_2$—, —C($CH_3$)

($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

As Q', a divalent linking group containing an ester bond or an ether bond is preferable, and —$R^{91}$—O—, —$R^{92}$—O—C(=O)— or —C(=O)—O—$R^{93}$—O—C(=O)— is more preferable.

In the group represented by the formula: $X^3$-Q'-, the hydrocarbon group for $X^3$ is the same as the hydrocarbon groups of 1 to 30 carbon atoms for $R^a$ in the aforementioned formula (C3).

Among these, as $X^3$, a linear alkyl group which may have a substituent, or a cyclic group which may have a substituent is preferable. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, or any one of groups represented by the aforementioned formulae (L2) to (L6), (S3) and (S4) are preferable.

Among these examples, as the aforementioned $R^{4'''}$, a halogenated alkyl group or a group having $X^3$-Q'- as a substituent is preferable.

When the $R^{4'''}$ group has $X^3$-Q'- as a substituent, as $R^{4'''}$, a group represented by the formula: $X^3$-Q'-$Y^3$— (in the formula, Q' and $X^3$ are the same as defined above, and $Y^3$ represents an alkylene group of 1 to 4 carbon atoms which may have a substituent or a fluorinated alkylene group of 1 to 4 carbon atoms which may have a substituent is preferable.

In the group represented by the formula $X^3$-Q'-$Y^3$—, as the alkylene group for $Y^3$, the same alkylene group as those described above for Q' in which the number of carbon atoms is 1 to 4 can be used.

As the fluorinated alkylene group, the aforementioned alkylene group in which part or all of the hydrogen atoms has been substituted with fluorine atoms can be used.

Specific examples of $Y^3$ include —$CF_2$—, —$CF_2CF_2$—, —$CF_2CF_2CF_2$—, —CF($CF_3$)$CF_2$—, —CF($CF_2CF_3$)—, —C($CF_3$)$_2$—, —$CF_2CF_2CF_2CF_2$—, —CF($CF_3$)$CF_2CF_2$—, —$CF_2$CF($CF_3$)$CF_2$—, —CF($CF_3$)CF($CF_3$)—, —C($CF_3$)$_2$$CF_2$—, —CF($CF_2CF_3$)$CF_2$—, —CF($CF_2CF_2CF_3$)—, —C($CF_3$)($CF_2CF_3$)—; —CHF—, —$CH_2CF_2$—, —$CH_2CH_2CF_2$—, —$CH_2CF_2CF_2$—, —CH($CF_3$)$CH_2$—, —CH($CF_2CF_3$)—, —C($CH_3$)($CF_3$)—, —$CH_2CH_2CH_2CF_2$—, —$CH_2CH_2CF_2CF_2$—, —CH($CF_3$)$CH_2CH_2$—, —$CH_2$CH($CF_3$)$CH_2$—, —CH($CF_3$)CH($CF_3$)—, —C($CF_3$)$_2CH_2$—; —$CH_2$—, —$CH_2CH_2$—, —$CH_2CH_2CH_2$—, —CH($CH_3$)$CH_2$—, —CH($CH_2CH_3$)—, —C($CH_3$)$_2$—, —$CH_2CH_2CH_2CH_2$—, —CH($CH_3$) $CH_2CH_2$—, —$CH_2$CH($CH_3$)$CH_2$—, —CH($CH_3$)CH ($CH_3$)—, —C($CH_3$)$_2CH_2$—, —CH($CH_2CH_3$)$CH_2$—, —CH($CH_2CH_2CH_3$)—, and —C($CH_3$)($CH_2CH_3$)—.

$Y^3$ is preferably a fluorinated alkylene group, and most preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —CF($CF_3$)$CF_2$—, —$CF_2CF_2CF_2CF_2$—, —CF($CF_3$)$CF_2CF_2$—, —$CF_2$CF($CF_3$)$CF_2$—, —CF($CF_3$)CF($CF_3$)—, —C($CF_3$)$_2$$CF_2$—, —CF($CF_2CF_3$)$CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

Specific examples of groups represented by formula $R^{4'''}SO^{3-}$ in which $R^{4'''}$ represents $X_3$Q'-Y-3 include anions represented by the following formulae (b1) to (b9).

[Chemical Formula 67]

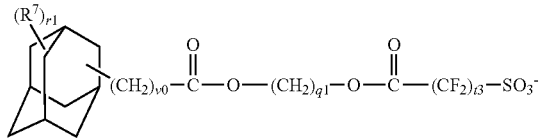

(b1)

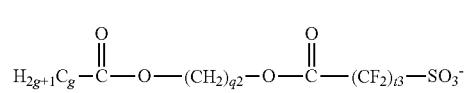

(b2)

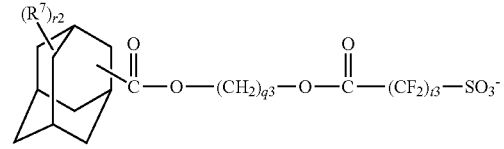

(b3)

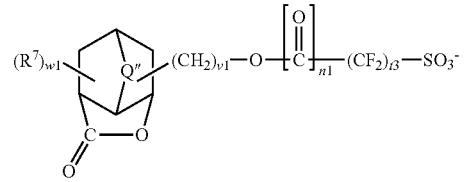

(b4)

(b5)

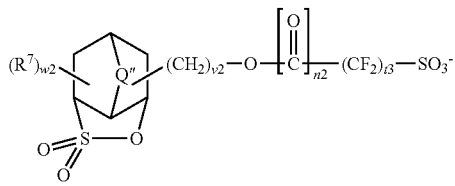

[Chemical Formula 68]

(b6)

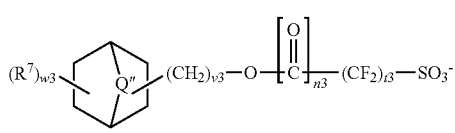

(b7)

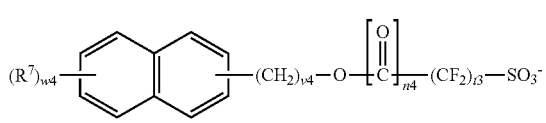

(b8)

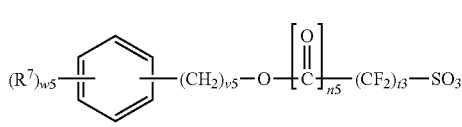

(b9)

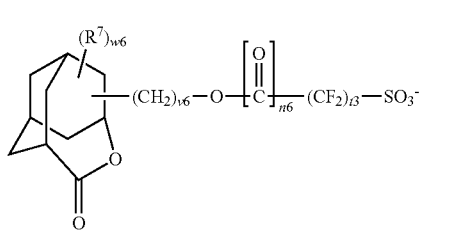

In the formulae, q1 and q2 each independently represents an integer of 1 to 5; q3 represents an integer of 1 to 12; t3 represents an integer of 1 to 3; r1 and r2 each independently represents an integer of 0 to 3; g represents an integer of 1 to 20; $R^7$ represents a substituent; n1 to n6 each independently represents 0 or 1; v0 to v6 each independently represents an integer of 0 to 3; w1 to w6 each independently represents an integer of 0 to 3; and Q" is the same as defined above.

As the substituent for $R^7$, the same groups as those which the aforementioned aliphatic hydrocarbon group or aromatic hydrocarbon group for $R^a$ in the aforementioned formula (C3) may have as a substituent can be used.

If there are two or more of the $R^7$ group, as indicated by the values r1, r2, and w1 to w6, then the two or more of the $R^7$ groups may be the same or different from each other.

Further, as preferable examples of the anion moiety of the component (G1), an anion represented by general formula (G1a-3) shown below and an anion moiety represented by general formula (G1a-4) shown below can also be mentioned.

[Chemical Formula 69]

(G1a-3)

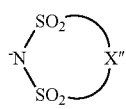

(G1a-4)

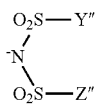

In the formulas, X" represents an alkylene group of 2 to 6 carbon atoms in which at least one hydrogen atom has been substituted with a fluorine atom; and each of Y" and Z" independently represents an alkyl group of 1 to 10 carbon atoms in which at least one hydrogen atom has been substituted with a fluorine atom.

In formula (G1a-3), X" represents a linear or branched alkylene group in which at least one hydrogen atom has been substituted with a fluorine atom, and the alkylene group preferably has 2 to 6 carbon atoms, more preferably 3 to 5 carbon atoms, and most preferably 3 carbon atoms.

In formula (G1a-4), each of Y" and Z" independently represents a linear or branched alkyl group in which at least one hydrogen atom has been substituted with a fluorine atom, and the alkyl group preferably has 1 to 10 carbon atoms, more preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved.

The amount of fluorine atoms within the alkylene group or alkyl group, i.e., fluorination ratio, is preferably from 70 to 100%, more preferably from 90 to 100%, and it is particularly desirable that the alkylene group or alkyl group be a perfluoroalkylene or perfluoroalkyl group in which all hydrogen atoms are substituted with fluorine atoms.

As the anion moiety of the component (G1), an anion represented by the aforementioned formula "$R^{4"}SO_3^-$" (in particular, any one of anions represented by the aforementioned formulae (b1) to (b9) which is a group in which $R^{4"}$ is "$X^3$-$Q'$-$Y^3$-") or an anion represented by the aforementioned formula (G1a-3) is most preferable.

As the component (G1), one type of compound may be used alone, or two or more types may be used in combination.

In the resist composition, the amount of the component (G1) within the component (G) is preferably 40% by weight or more, still more preferably 70% by weight or more, and may be even 100% by weight. When the amount of the component (G1) is at least as large as the lower limit of the above-mentioned range, the storage stability and the lithography properties become excellent.

In the resist composition, the amount of the component (G1), relative to 100 parts by weight of the component (A) is preferably from 0.5 to 30 parts by weight, more preferably from 1 to 20 parts by weight, and most preferably from 2 to 15 parts by weight. When the amount of the component (G1) is within the above-mentioned range, the lithography properties become excellent.

[Component (G2)]

The component (G2) is a component which does not fall under the definition of the component (G1), and the component (G2) itself exhibits acidity, so as to act as a proton donor. Examples of the component (G2) include a non-ionic acid which does not form a salt.

As the component (G2), there is no particular limitation as long as it is an acid exhibiting an acid strength sufficient for increasing the solubility of the base component (A) in an alkali developing solution, and is not decomposed by exposure to exhibit decreased acid strength. As the component (G2), in terms of the reactivity with the acid dissociable group of the base component and ease in increasing the solubility of the resist film in an alkali developing solution, an imine acid or a sulfonic acid compound is preferable, and examples thereof include sulfonylimide, bis(alkylsulfonyl)imide, tris(alkylsulfonyl)methide, and any of these compounds which have a fluorine atom.

In particular, a compound represented by any one of general formulae (G2-1) to (G2-3) shown below (preferably a compound represented by general formula (G2-2)), a compound in which an anion represented by any one of general formulae (b1) to (b8) described above has "—$SO_3^-$" replaced by "—$SO_3H$", a compound in which an anion represented by general formula (G1a-3) or (G1a-4) described above has "$N^-$" replaced by "NH", and camphorsulfonic acid are preferable. Other examples include acid components such as a fluorinated alkyl group-containing carboxylic acid, a higher fatty acid, a higher alkylsulfonic acid, and a higher alkylarylsulfonic acid.

[Chemical Formula 70]

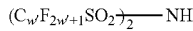
(G2-1)

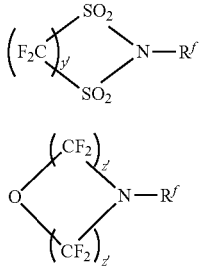
(G2-2)

(G2-3)

In formula (G2-1), w' represents an integer of 1 to 5. In formula (G2-2), $R^f$ represents a hydrogen atom or an alkyl group (provided that part or all of the hydrogen atoms within the alkyl group may be substituted with a fluorine atom, a hydroxy group, an alkoxy group, a carboxy group or an amino group); and y' represents 2 or 3. In formula (G2-3), $R^f$ is the same as defined above; and z' represents 2 or 3.

Examples of compounds represented by the aforementioned formula (G2-1) include $(C_4F_9SO_2)_2NH$ and $(C_3F_7SO_2)_2NH$.

In the aforementioned formula (G2-2), the alkyl group for $R^r$ preferably has 1 or 2 carbon atoms, and more preferably 1.

Examples of the alkoxy group which may substitute the hydrogen atom(s) within the alkyl group include a methoxy group and an ethoxy group.

Examples of a compound represented by the aforementioned formula (G2-2) include a compound represented by a chemical formula (G2-21) shown below.

[Chemical Formula 71]

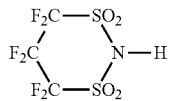
(G2-21)

In the aforementioned formula (G2-3), $R^f$ is the same as defined for $R^f$ in formula (G2-2).

Examples of a compound represented by the aforementioned formula (G2-3) include a compound represented by a chemical formula (G2-31) shown below.

[Chemical Formula 72]

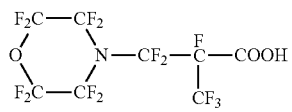
(G2-31)

As the fluorinated alkyl group-containing carboxylic group, for example, $C_{10}F_{21}COOH$ can be mentioned.

Examples of the higher fatty acid include higher fatty acids having an alkyl group of 8 to 20 carbon atoms, and specific examples thereof include dodecanoic acid, tetradecanoic acid, and stearic acid.

The alkyl group of 8 to 20 carbon atoms may be either linear or branched. Further, the alkyl group of 8 to 20 carbon atoms may have a phenylene group, an oxygen atom or the like interposed within the chain thereof. Furthermore, the alkyl group of 8 to 20 carbon atoms may have part of the hydrogen atoms substituted with a hydroxy group or a carboxy group.

Examples of the higher alkylsulfonic acid include sulfonic acids having an alkyl group preferably with an average of 9 to 21 carbon atoms, more preferably 12 to 18 carbon atoms, and specific examples thereof include decanesulfonic acid, dodecanesulfonic acid, tetradecanesulfonic acid, tetradecanesulfonic acid, pentadecanesulfonic acid and octadecanesulfonic acid.

Examples of the higher alkylarylsulfonic acid include alkylbenzenesulfonic acids and alkylnaphthalenesulfonic acids having an alkyl group preferably with an average of 6 to 18 carbon atoms, more preferably 9 to 15 carbon atoms, and specific examples thereof include dodecylbenzenesulfonic acid and decylnaphthalenesulfonic acid.

Examples of the acid components include alkyldiphenyletherdisulfonic acids preferably with an average of 6 to 18 carbon atoms, more preferably 9 to 15, and preferable examples thereof include dodecyldiphenyletherdisulfonic acid.

Examples of the component (G2) other than those described above include organic carboxylic acid, a phosphorus oxo acid or derivative thereof.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

When the component (G) includes a component (G2), as the component (G2), one type of compound may be used, or two or more types may be used in combination. Among these, as the component (G2), at least one member selected from the group consisting of sulfonylimide, bis(alkylsulfonyl)imide, tris(alkylsulfonyl)methide and any of these compounds having a fluorine atom is preferable, and it is most preferable to use at least one of these compounds having a fluorine atom.

Further, when the resist composition contains the component (G2), the amount of the component (G2) relative to 100 parts by weight of the component (A) is preferably within a range from 0.5 to 20 parts by weight, more preferably from 1 to 15 parts by weight, and still more preferably from 1 to 10 parts by weight. When the amount of the component (G2) is at least as large as the lower limit of the above-mentioned range, the solubility of the resist film in an alkali developing solution is likely to be increased. On the other hand, when the amount of the component (G2) is no more than the upper limit of the above-mentioned range, an excellent sensitivity can be obtained.

<Other Components>

In the resist composition of the present invention, a component other than the aforementioned components, such as an acid amplifier component, a fluorine-containing compound, a silicon-containing compound, an amine or the like can be blended.

[Acidic Amplifier Component; Component (H)]

In the present invention, the component (H) is decomposed by an acid to generate a free acid, and the free acid further decomposes the component (H) to further generate free acid. In this manner, by the action of acid, the component (H) is serially decomposed, and generates many free acid molecules.

The component (H) is not particularly limited, as long as it is decomposable by the action of an acid, and is capable of further generating acid to self-catalytically amplify acid. Preferable examples of the component (H) include compounds having a bridged-carbon ring skeleton structure.

Here, the term "compound having a bridged-carbon ring skeleton structure" refers to a compound which has a structure of a bridging bond formed by a plurality of carbon rings in a molecule thereof.

By virtue of the compound having a bridged-carbon ring skeleton structure having a bridging bond, the molecule becomes rigid, and the thermal stability of the compound is improved.

The number of carbon rings is preferably from 2 to 6, and more preferably 2 or 3.

The bridged carbon ring may have part or all of the hydrogen atoms substituted with an alkyl group, an alkoxy group or the like. The alkyl group preferably has 1 to 6 carbon atoms, more preferably 1 to 3, and specific examples of the alkyl group include a methyl group, an ethyl group and a propyl group. The alkoxy group preferably has 1 to 6 carbon atoms, more preferably 1 to 3, and specific examples of the alkoxy group include a methoxy group and an ethoxy group. The bridged carbon ring may have an unsaturated bond such as a double bond.

In the present invention, it is most preferable that the bridged carbon has, on the ring thereof a hydroxy group and a sulfonate group represented by general formula (Hs) shown below bonded to the carbon atom adjacent to the carbon atom having the hydroxy group bonded thereto.

[Chemical Formula 73]

In the formula, $R^o$ represents an aliphatic group, an aromatic group or a heterocyclic group.

In the aforementioned formula (Hs), $R^o$ represents an aliphatic group, an aromatic group or a heterocyclic group.

Examples of the aliphatic group for $R^o$ include a chain-like or cyclic alkyl group or an alkenyl group, and preferably has 1 to 12 carbon atoms, more preferably 1 to 10 carbon atoms.

The aromatic group may be either a monocyclic group or a polycyclic group, and specific examples thereof include aryl groups.

The heterocyclic group may be a monocyclic group or a polycyclic group, and specific examples thereof include groups which are derived from various conventional heterocyclic compounds.

The aforementioned aliphatic group, aromatic group and heterocyclic group may have a substituent, and examples of the substituent include a halogen atom, an alkyl group, an alkoxy group, an amino group, a substituted amino group and an oxygen atom ($=O$).

Specific examples of the aforementioned aliphatic group and the aromatic group include a methyl group, an ethyl group, a propyl group, a butyl group, an acyl group, a hexyl group, a vinyl group, a propylene group, an allyl group, a cyclohexyl group, a cyclooctyl group, a bicyclohydrocarbon group, a tricyclohydrocarbon group, a phenyl group, a tolyl group, a benzyl group, a phenethyl group, a naphthyl group, a naphthylmethyl group, and substitution products thereof.

Examples of the heterocyclic group include groups derived from various heterocyclic groups, such as a 5-membered ring compound containing one hetero atom or a condensed ring compound thereof (e.g., furan, thiophene, pyrrole, benzofuran, thionaphthene, indole or carbazole); a 5-membered ring compound containing two hetero atoms or a condensed ring compound thereof (e.g., oxazole, thiazole or pyrazole); a 6-membered ring compound containing one hetero atom or a condensed ring compound thereof (e.g., pyran, pyrone, coumarin, pyridine, quinoline, isoquinoline or acridine); and a 5-membered ring compound containing two hetero atoms or a condensed ring compound thereof (e.g., pyridazine, pyrimidine, pyrazine or phthalazine).

In the present invention, when the component (H) has, on the bridged carbon ring, a hydroxy group and a sulfonate group represented by the aforementioned general formula (Hs), such a component (H) is decomposed by the action of an acid to generate a new acid ($R^oSO_3H$).

In this manner, one acid increases in one reaction, and the reaction is accelerated as the reaction proceeds, thereby serially decomposing the component (H).

In such a case, the strength of the generated acid in terms of the acid dissociation constant (pKa) is preferably 3 or less, and most preferably 2 or less. When the pKa is 3 or less, the generated acid itself is likely to induce the self-decomposition. On the other hand, when the generated acid has a weaker strength, it becomes difficult to induce the self-decomposition.

Examples of the free acid ($R^0SO_3H$) generated by the above reaction include methanesulfonic acid, ethanesulfonic acid, propanesulfonic acid, butanesulfonic acid, pentanesulfonic acid, hexanesulfonic acid, heptanesulfonic acid, octanesulfonic acid, cyclohexanesulfonic acid, camphorsulfonic acid, trifluoromethanesulfonic acid, 2,2,2-trifluoroethanesulfonic acid, benzenesulfonic acid, p-toluenesulfonic acid, p-bromobenzenesulfonic acid, p-nitrobenzenesulfonic acid, 2-thiophenesulfonic acid, 1-naphthalenesulfonic acid and 2-naphthalenesulfonic acid.

Specific examples of the component (H) include compounds represented by general formulae (H1) to (H4) shown below (hereafter, the compounds corresponding to general formulae are respectively referred to as "compounds (H1) to (H4)").

[Chemical Formula 74]

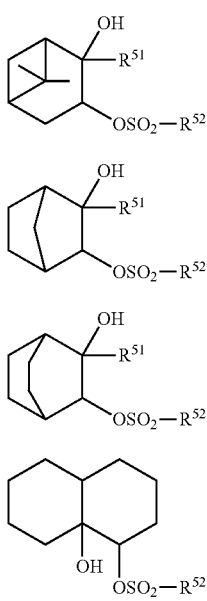

In the formulae, $R^{51}$ represents a hydrogen atom, an aliphatic group or an aromatic group; and $R^{52}$ represents an aliphatic group, an aromatic group or a heterocyclic group.

In the aforementioned general formulae (H1) to (H3), $R^{51}$ represents a hydrogen atom, an aliphatic group or an aromatic group. The aliphatic group and the aromatic group for $R^{51}$ is the same as defined for the aliphatic group and the aromatic group for the aforementioned $R^0$. As $R^{51}$, an aliphatic group or an aromatic group is preferable, an aliphatic group is more preferable, a lower alkyl group is still more preferable, and a methyl group is most preferable.

In the aforementioned general formulae (H1) to (H4), $R^{52}$ represents an aliphatic group, an aromatic group or a heterocyclic group, and is the same as defined for $R^0$. As $R^{52}$, an aliphatic group or an aromatic group is preferable, and an aliphatic group is more preferable.

With respect to the compounds (H1) to (H4), the compound (H1) has a bridge bond on the 1st and 3rd positions of the bicyclo compound, the compounds (H2) and (H3) has a bridge bond on the 1st and 4th positions of the bicyclo compound, and the compound (H4) has a bridge bond on the 1st and 6th positions of the bicyclo compound (decarine).

Therefore, in the compounds (H1) to (H4), the conformation change of the cyclohexane ring is greatly suppressed, and hence, the ring structure exhibits rigidity.

As the component (H), for example, a compound in which the bridged carbon has, on the ring thereof, a hydroxy group and a sulfonate group represented by general formula (Hs) bonded to the carbon atom adjacent to the carbon atom having the hydroxy group bonded thereto (such as the compounds (H1) to (H4)) can be readily synthesized by recting a diol compound with a halide of the sulfonic acid. The diol compound has two isomers, namely, cis-isomer and trans-isomer, but the cis-isomer is thermally stable, and is therefore preferably used. Further, such a compound can be stably stored as long as an acid does not coexist.

Specific examples of preferable component (H) are shown below.

[Chemical Formula 75]

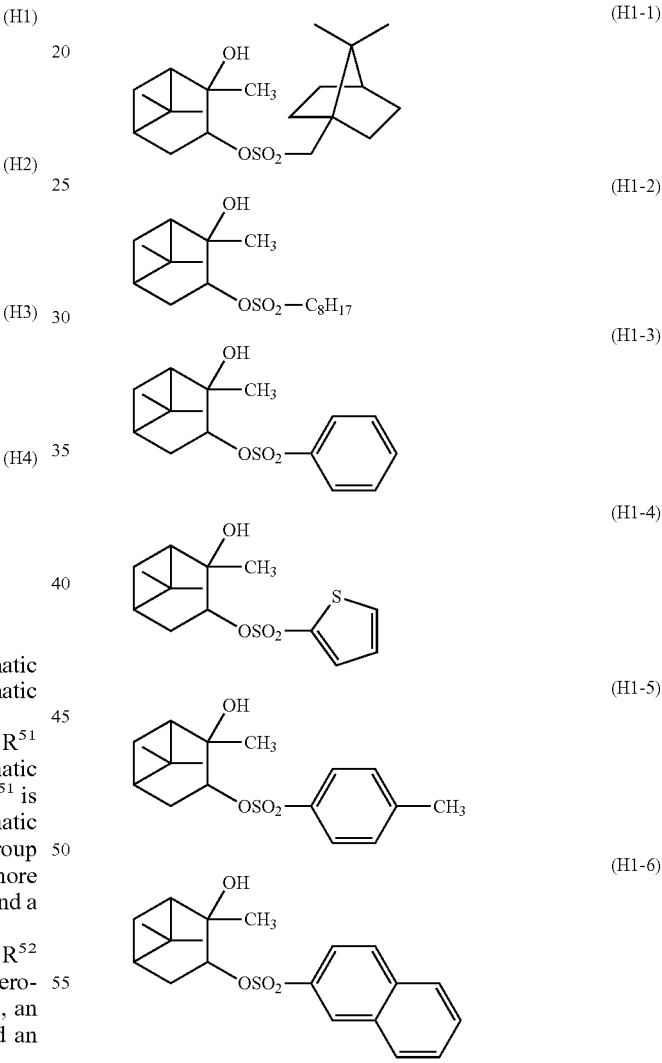

[Chemical Formula 76]

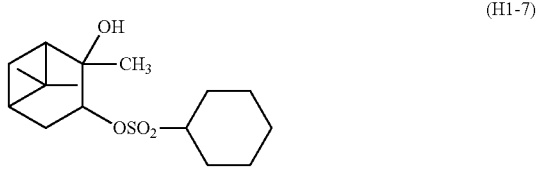

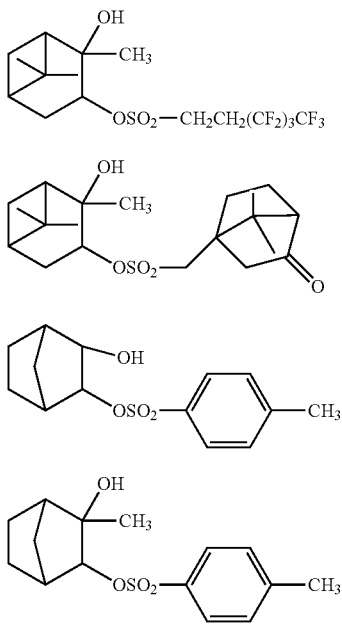

(H1-8)

(H1-9)

(H2-1)

(H2-2)

Among the above examples, as the component (H), in terms of the effects of the present invention, the compound (H1) or the compound (H2) is preferable, and the compound (H1) is more preferable. More specifically, it is preferable to use at least one member selected from the group consisting of compounds represented by chemical formulae (H1-1) to (H1-9), and it is most preferable to use a compound represented by chemical formula (H1-9).

As the component (H), one type of compound may be used, or two or more types of compounds may be used in combination.

In the resist composition, the amount of the component (H) relative to 100 parts by weight of the component (A) is preferably 0.1 to 30 parts by weight, and more preferably 1 to 20 parts by weight. When the amount of the component (H) is at least as large as the lower limit of the above-mentioned range, the resolution is improved. On the other hand, when the amount of the component (H) is no more than the upper limit of the above-mentioned range, the sensitivity is improved.

When the component (H) is used, the mixing ratio of the component (H) to the component (J) in terms of molar ratio is preferably from 9:1 to 1:9, more preferably from 9:1 to 5:5, and most preferably from 9:1 to 6:4. When the ratio of the component (H) is at least as large as the lower limit of the above-mentioned range, the resolution is improved. On the other hand, when the ratio of the component (H) is no more than the upper limit of the above-mentioned range, the sensitivity is improved.

[Fluorine-Containing Compound or Silicon-Containing Compound; Component (F)]

In the resist composition of the present invention, a fluorine-containing compound or a silicon-containing compound (hereafter, referred to as "component (F)") may be blended for imparting water repellency to the resist film.

The component (F) is not particularly limited as long as it is a compound containing a fluorine atom or a silicon atom, and any compound conventionally used as an additive for a resist composition can be used. By virtue of containing a fluorine atom or a silicon atom, the component (F) can be distributed near the surface of the resist film.

The component (F) may be a resin component (F1) containing a fluorine atom or a silicon atom (hereafter, referred to as "component (F1)"), a low molecular weight material containing a fluorine atom or a silicon atom, or a mixture thereof. Among these, in the present invention, as the component (F), a component (F1) is preferable.

As the component (F1), for example, it is preferable to include a structural unit (f1) represented by formula (f1-1) shown below.

[Chemical Formula 77]

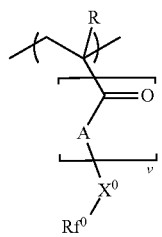

(f1-1)

In the formula, R represents a hydrogen atom, an alkyl group of 1 to 5 carbon atoms or a halogenated alkyl group of 1 to 5 carbon atoms; A represents —O— or —NH—; $X^0$ represents a single bond or a divalent linking group and $Rf^0$ represents an organic group, provided that at least one of $X^0$ and $Rf^0$ has a fluorine atom or a silicon atom; and v represents 0 or 1.

In formula (f1-1), R represents a hydrogen atom, an alkyl group of 1 to 5 carbon atoms or a halogenated alkyl group of 1 to 5 carbon atoms. The alkyl group of 1 to 5 carbon atoms and the halogenated alkyl group of 1 to 5 carbon atoms for R are the same as defined above.

Among these, as R, a hydrogen atom or a methyl group is preferable.

In formula (f1-1), A represents —O— or —NH—, and is preferably —O—.

In formula (f1-1), v represents 0 or 1. In the present invention, v represents 0 means that —C(=O)-A- is a single bond.

In formula (f1-1), $X^0$ represents a single bond or a divalent linking group.

Examples of the divalent linking group for $X^0$ include a divalent hydrocarbon group which may have a substituent and a divalent linking group containing a hetero atom, and are the same as defined for the divalent hydrocarbon group which may have a substituent and the divalent linking group containing a hetero atom described above for $Y^2$. The divalent linking group for $X^0$ may or may not have an acid dissociable group in the structure thereof. The acid dissociable group is the same as defined for the structural unit (a1).

As $X^0$, a single bond or a divalent linking group containing a hetero atom is preferable, and a single bond or a divalent linking group containing —C(=O)—O— is more preferable.

More specifically, in the case where v is 0, as the divalent linking group for $X^0$, a combination of a divalent aromatic hydrocarbon group which may have a substituent with a divalent linking group containing —O—C(=O)— is preferable; and a combination of a group in which one hydrogen atom has been removed from a phenyl group or a naphthyl group which may have a substituent with —O—C(=O)—, or a combination of these groups with a linear alkylene group is most preferable.

Further, in the case where v is 1, as the divalent linking group for $X^0$, a combination of a divalent hydrocarbon group which may have a substituent with a divalent linking group containing —C(=O)—O— is preferable; and a combination of an aliphatic hydrocarbon group or an aromatic hydrocarbon group which may have a substituent with —C(=O)—O— is more preferable. Furthermore, a combination of these groups with an ether bond (—O—) is also preferable.

In the case where $X^0$ is a divalent linking group, $X^0$ may or may not have a fluorine atom or a silicon atom. In the case where $X^0$ is a single bond, or in the case where $X^0$ is a divalent linking group having no fluorine atom or silicon atom, the organic group for $Rf^0$ described later has a fluorine atom or a silicon atom.

In formula (f1-1), $Rf^0$ represents an organic group.

The organic group for $Rf^0$ may be an organic group having a fluorine atom or a silicon atom, or an organic group having no fluorine atom or silicon atom. However, in the case where $X^0$ is a single bond, or in the case where $X^0$ is a divalent linking group having no fluorine atom or silicon atom, the organic group for $Rf^0$ has a fluorine atom or a silicon atom. An "organic group having a fluorine atom or a silicon atom" refers to an organic group in which part or all of the hydrogen atoms have been substituted with a fluorine atom or a silicon atom.

As an example of an organic group for $Rf^0$, a hydrocarbon group which may have a fluorine atom or a silicon atom can be given. The hydrocarbon group which may have a fluorine atom or a silicon atom may be either an aliphatic hydrocarbon group or an aromatic hydrocarbon group.

Examples of the aliphatic hydrocarbon group for $Rf^0$ include a linear, branched or cyclic alkyl group.

The linear or branched alkyl group preferably has 1 to 15 carbon atoms, more preferably 1 to 10 carbon atoms, still more preferably 1 to 8 carbon atoms, and most preferably 1 to 5 carbon atoms.

The cyclic alkyl group preferably has 4 to 15 carbon atoms, more preferably 4 to 10 carbon atoms, still more preferably 6 to 10 carbon atoms, and most preferably 5 to 7 carbon atoms.

The aromatic hydrocarbon group for $Rf^0$ preferably has 5 to 30 carbon atoms, more preferably 5 to 20, still more preferably 6 to 15, and most preferably 6 to 12, and a phenyl group or a naphthyl group is particularly desirable.

These alkyl groups and aromatic hydrocarbon groups are preferably substituted with a fluorine atom or a silicon atom. The alkyl group or the aromatic hydrocarbon group preferably has 25% or more of the hydrogen atoms substituted with a fluorine atom or a silicon atom, more preferably 50% or more of the hydrogen atoms substituted with a fluorine atom or a silicon atom, and may even have all of the hydrogen atoms substituted with a fluorine atom or a silicon atom.

Further, these alkyl groups and aromatic hydrocarbon groups may be substituted with a substituent other than a fluorine atom and a silicon atom. Examples of the substituent other than a fluorine atom and a silicon atom include a hydroxy group, a chlorine atom, a bromine atom, an iodine atom and an alkoxy group of 1 to 5 carbon atoms.

Further, the cyclic group or the aromatic hydrocarbon group may be substituted with an alkyl group of 1 to 5 carbon atoms. The alkyl group of 1 to 5 carbon atoms is the same as the alkyl group of 1 to 5 carbon atoms which can be used as the substituent for the α-position.

Among the structural units represented by formula (f1-1), specific examples of preferable structural unit containing a fluorine atom include structural units represented by formulae (f1-11) to (f1-14) shown below.

[Chemical Formula 78]

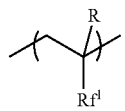
(f1-11)

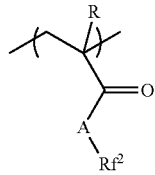
(f1-12)

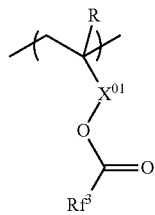
(f1-13)

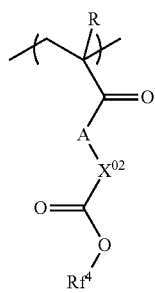
(f1-14)

In the formulae, $Rf^1$ and $Rf^2$ represents an organic group containing a fluorine atom; A is the same as defined above; $X^{01}$ and $X^{02}$ represents a divalent linking group; and $Rf^3$ and $Rf^4$ represents an organic group which may have a fluorine atom, provided that at least one of $X^{01}$ and $Rf^3$ has a fluorine atom, and at least one of $X^{02}$ and $Rf^4$ has a fluorine atom.

In formula (f1-11), $Rf^1$ represents an organic group having a fluorine atom, and is preferably an aromatic hydrocarbon group having a fluorine atom. Examples of the aromatic hydrocarbon group having a fluorine atom include the aromatic hydrocarbon groups for $Rf^0$ in which part or all of the hydrogen atoms have been substituted with a fluorine atom.

In formula (f1-12), A is the same as defined above. $Rf^2$ represents an organic group having a fluorine atom, and a cyclic alkyl group having a fluorine atom or an aromatic hydrocarbon group having a fluorine atom is preferable. Examples of the cyclic group having a fluorine atom and the aromatic hydrocarbon group having a fluorine atom include the cyclic groups and the aromatic hydrocarbon groups for $Rf^0$ in which part or all of the hydrogen atoms have been substituted with a fluorine atom.

In formula (f1-13), $X^{01}$ represents a divalent linking group, and is the same as defined for $X^0$.

Among these, as $X^{01}$, a divalent aromatic hydrocarbon group which may have as substituent is preferable, and a group in which one hydrogen atom has been removed from a phenyl group or a naphthyl group which may have a substituent is preferable.

As the substituent, a fluorine atom or an alkoxy group of 1 to 5 carbon atoms is preferable. In the case where $X^{01}$ has no fluorine atom, $Rf^3$ has a fluorine atom.

In formula (f1-13), $Rf^3$ represents an organic group which may have a fluorine atom, and is the same as defined for the organic group represented by $Rf^0$. As $Rf^3$, a linear or branched alkyl group which may have a substituent is preferable, and the alkyl group preferably has 1 to 5 carbon atoms.

In formula (f1-14), A is the same as defined above. $X^{02}$ represents a divalent linking group, and is the same as defined for $X^0$.

Among these, as $X^{02}$, a divalent aliphatic hydrocarbon group which may have a substituent, an aromatic hydrocarbon group which may have a substituent, an ether bond (—O—), or a combination thereof is preferable.

As the substituent, a fluorine atom or an alkoxy group of 1 to 5 carbon atoms is preferable. In the case where $X^{02}$ has no fluorine atom, $Rf^4$ has a fluorine atom.

In formula (f1-14), $Rf^4$ represents an organic group which may have a fluorine atom, and is the same as defined for $Rf^3$.

Further, by virtue of $R^{14}$ in formula (f1-14) being a base dissociable group, in the case of using an alkali developing process, the base dissociable group $R^{14}$ is decomposed to become hydrophilic, which is preferable. As the base dissociable group for $Rf^4$, there is no particular limitation as long as $Rf^4$ is a hydrocarbon group which may have a substituent, but a hydrocarbon group having a fluorine atom is preferable.

A base dissociable group refers to a group that is decomposable (—O—$Rf^4$ is dissociated) by the action of an alkali developing solution. The expression "decomposable in an alkali developing solution" means that the group is decomposable by the action of an alkali developing solution (preferably decomposable by action of a 2.38% by weight aqueous solution of tetramethylammonium hydroxide (TMAH) at 23° C.), and exhibits increased solubility in the alkali developing solution. The reason for this is that the ester bond [—C(=O)—O—$Rf^4$] is decomposed (hydrolyzed) by the action of a base (alkali developing solution), thereby forming a hydrophilic group [—C(=O)—OH](—O—$Rf^4$ is dissociated). By virtue of the structural unit (f1) changing from hydrophobic to hydrophilic before and after exposure, the scan tracking ability during immersion exposure is improved, and the defects after exposure can be further reduced.

Specific examples of the structural units represented by formulae (f1-11) to (f1-14) are shown below. In the formulae, $R^\beta$ represents a hydrogen atom or a methyl group.

[Chemical Formula 79]

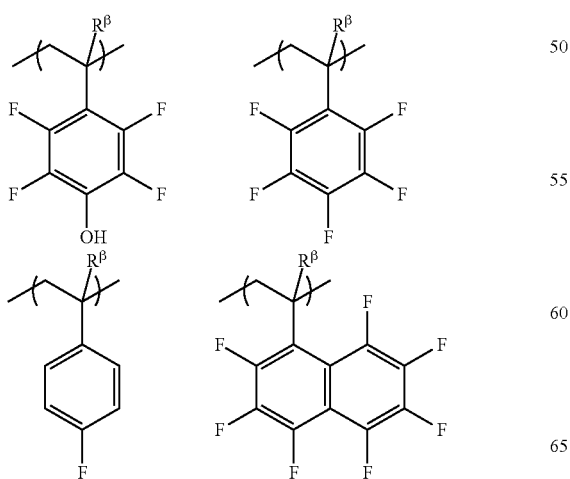

[Chemical Formula 80]

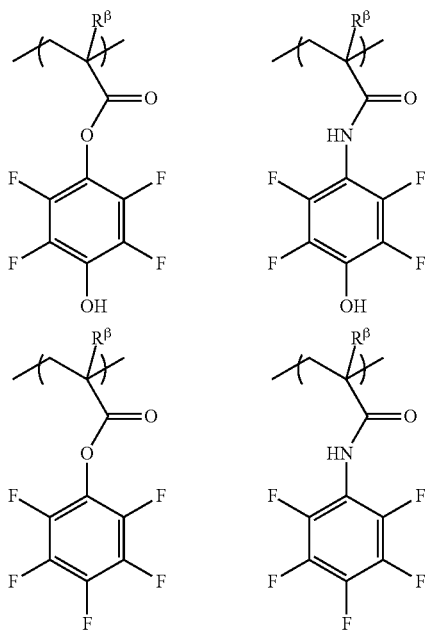

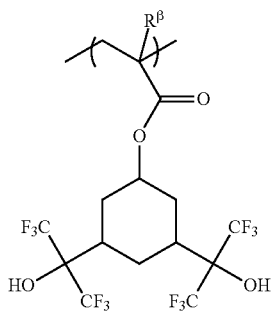

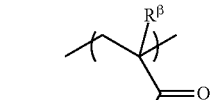

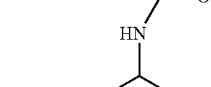

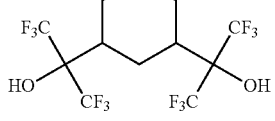

[Chemical Formula 81]

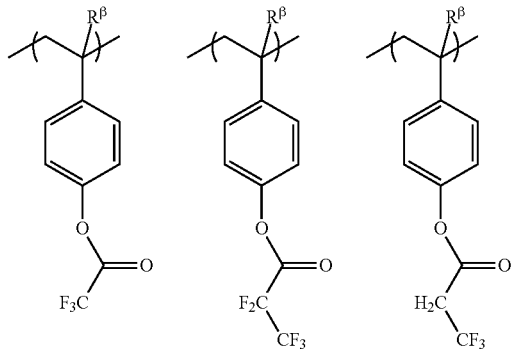

-continued
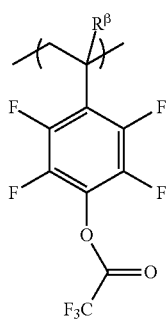 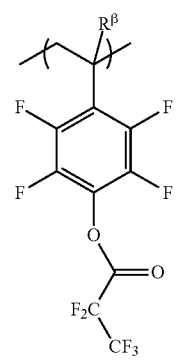
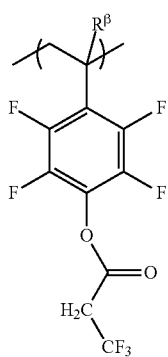 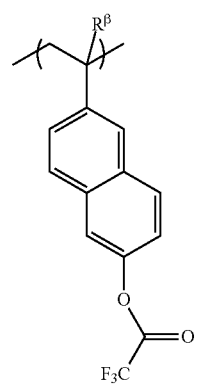
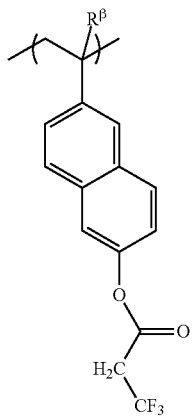 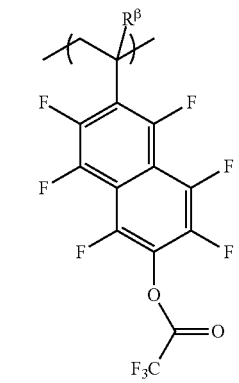
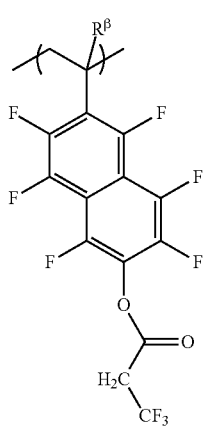 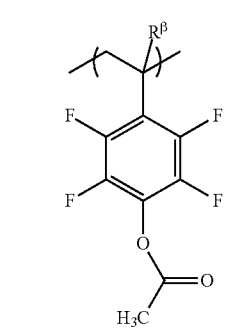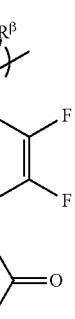
-continued
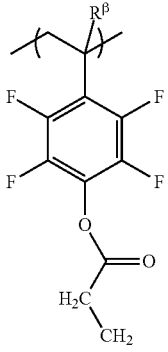 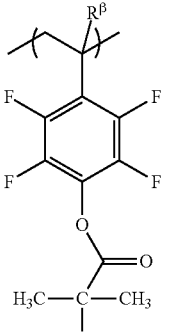
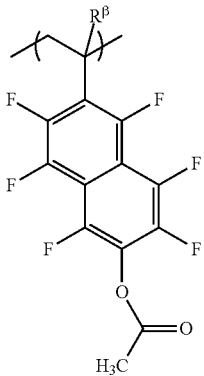 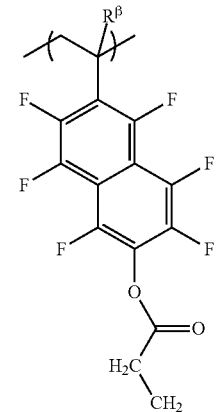
[Chemical Formula 82]
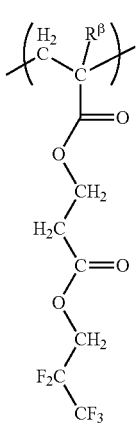 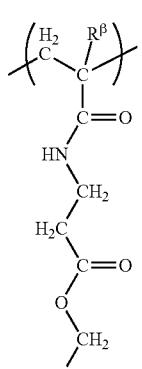 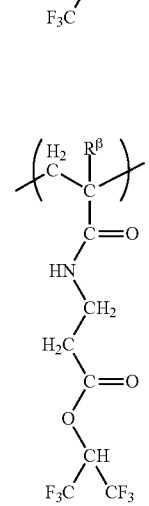
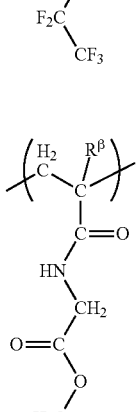 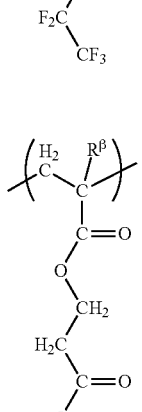

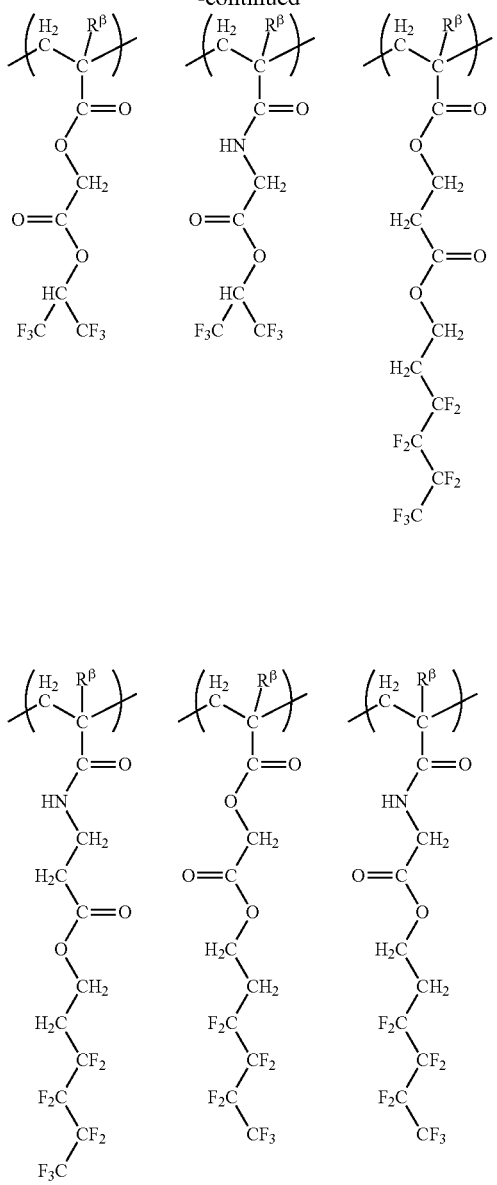
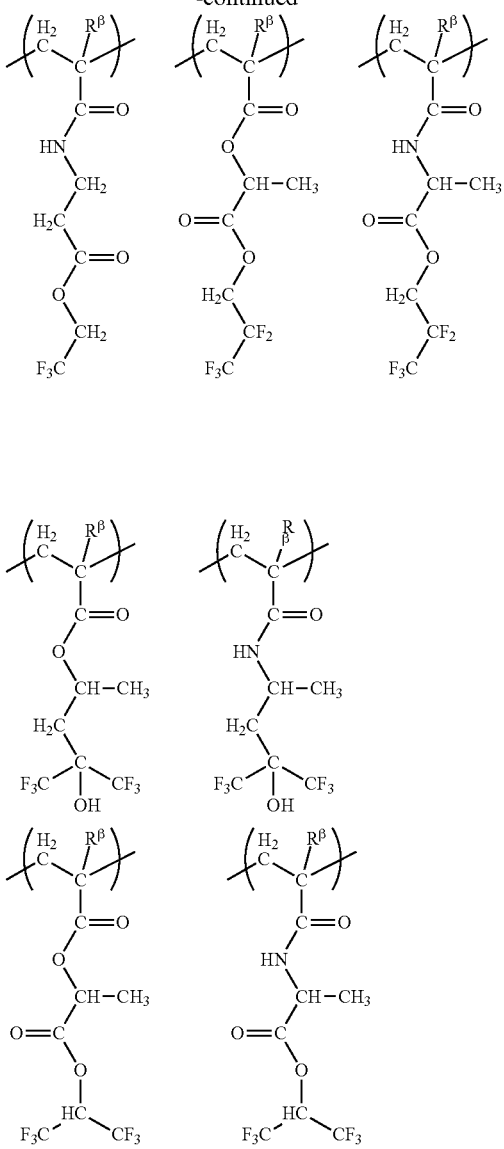
[Chemical Formula 83]
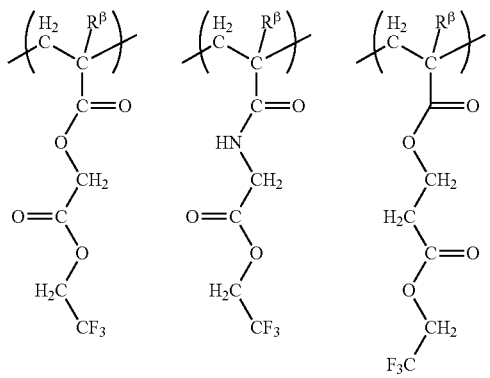
[Chemical Formula 84]
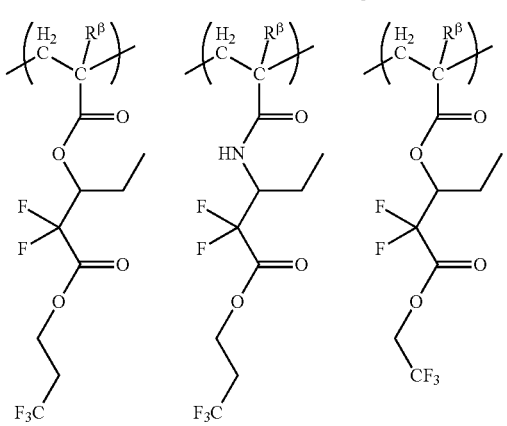

155
-continued
156
-continued
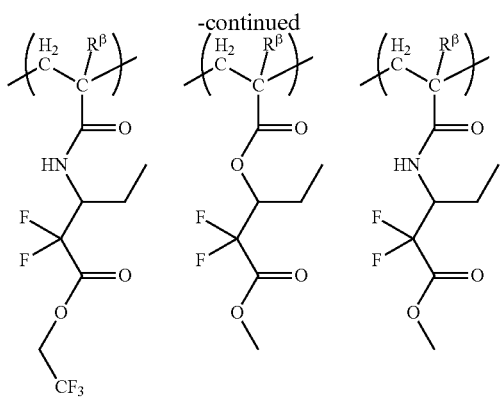
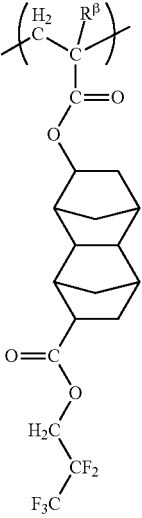
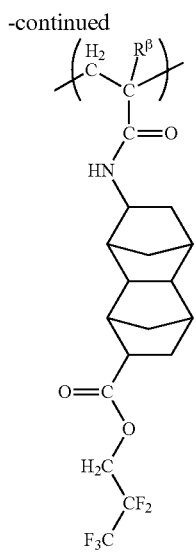
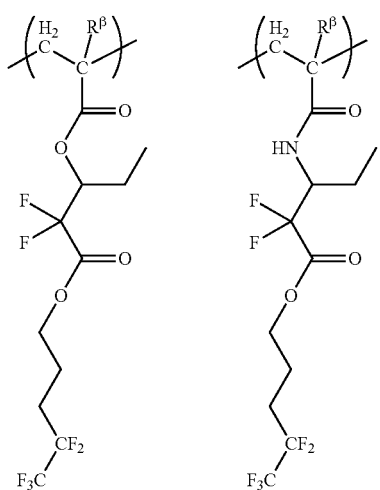
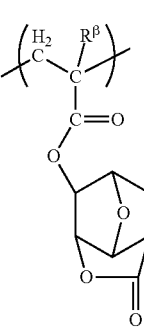
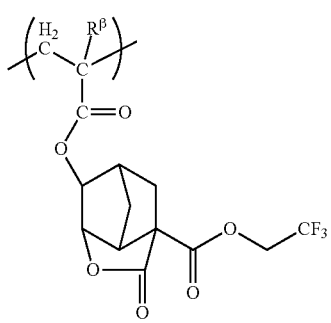
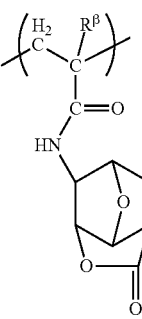

[Chemical Formula 85]
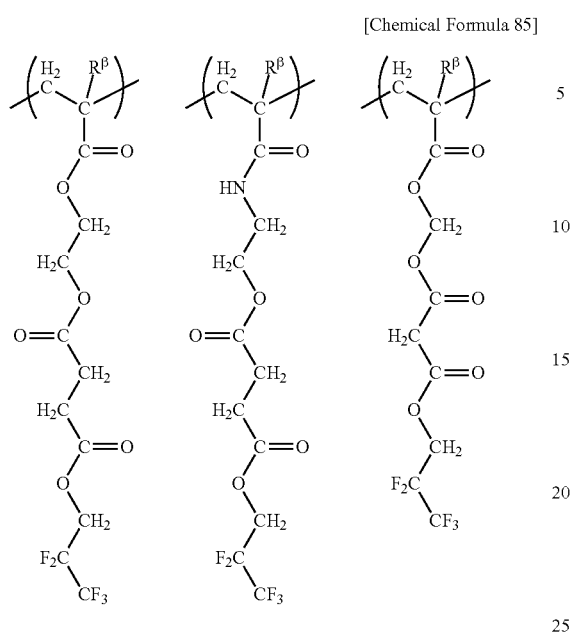
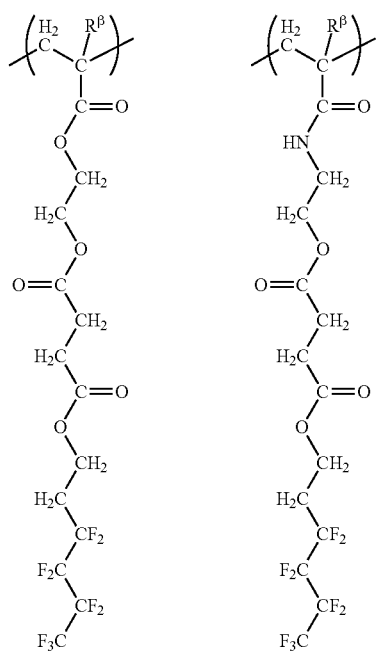
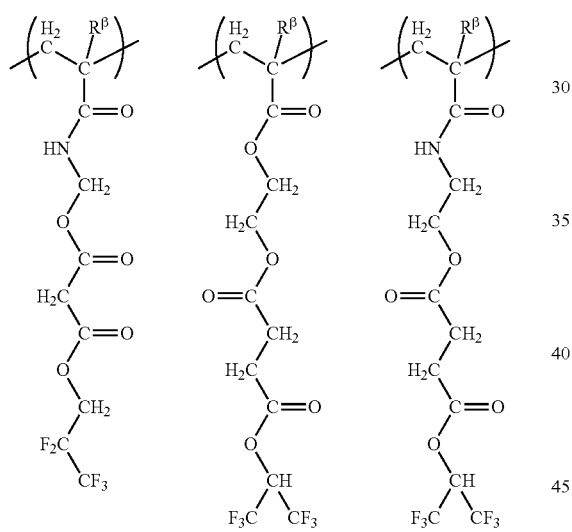
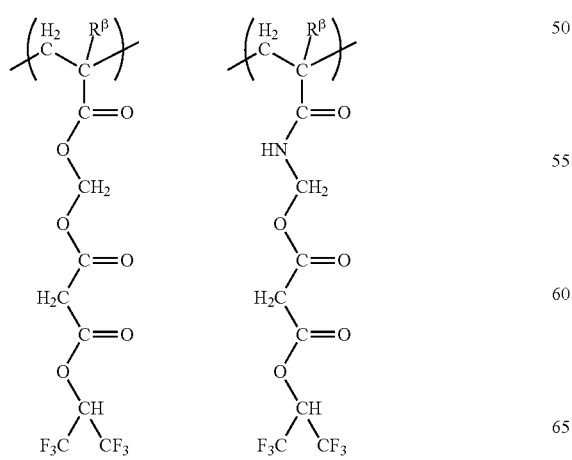
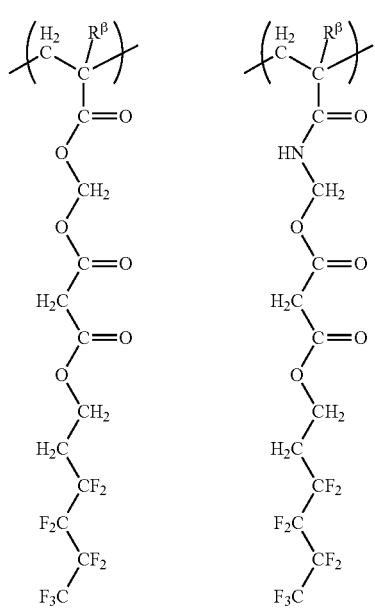

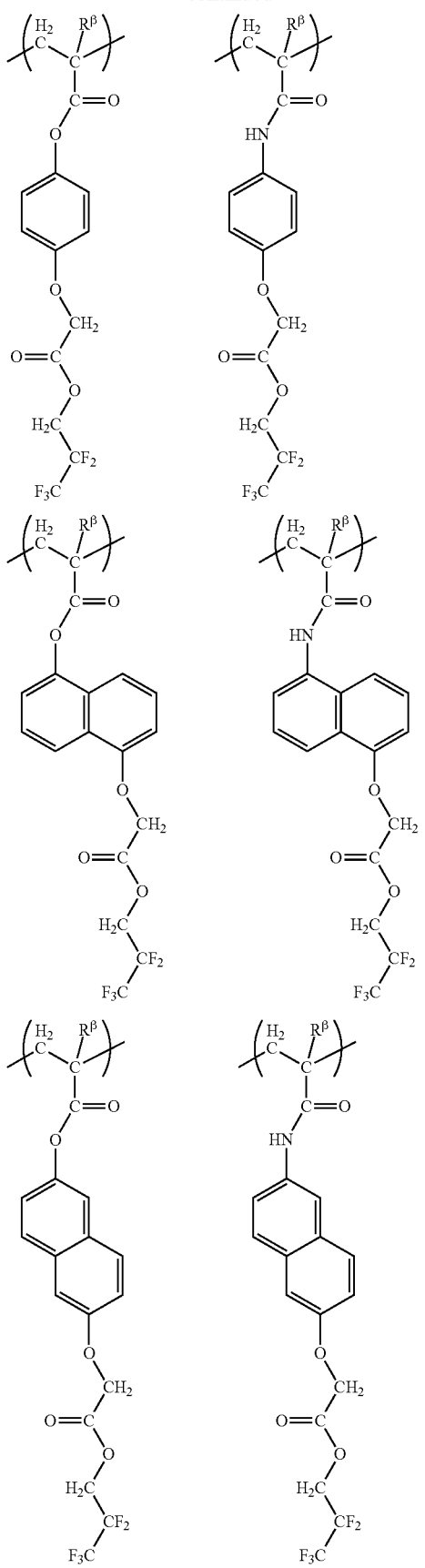

[Chemical Formula 87]
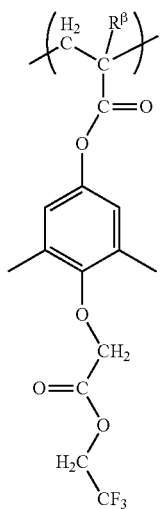
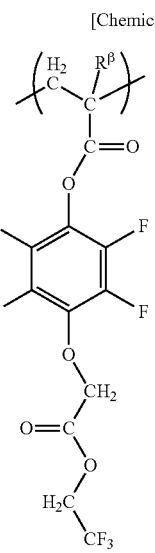
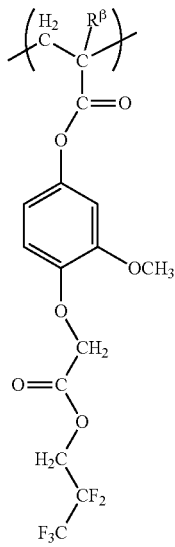
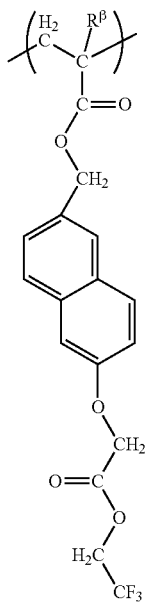
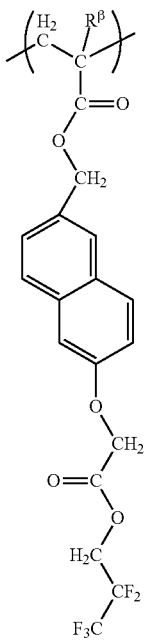
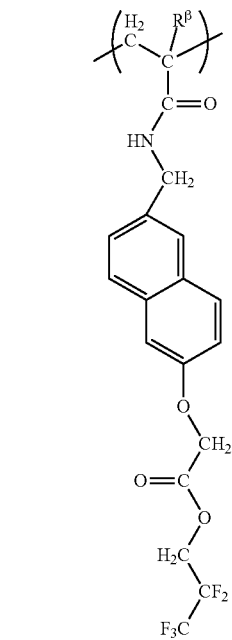
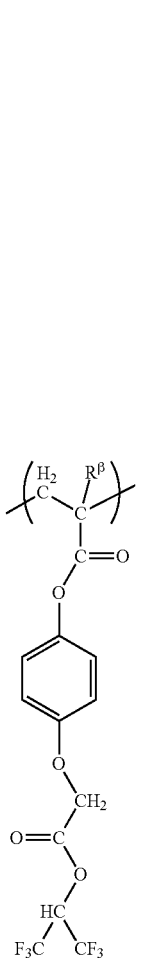
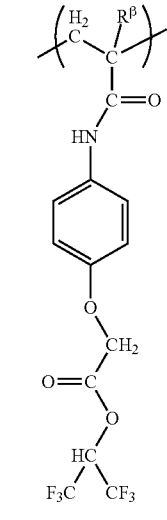

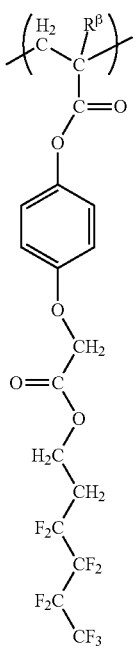
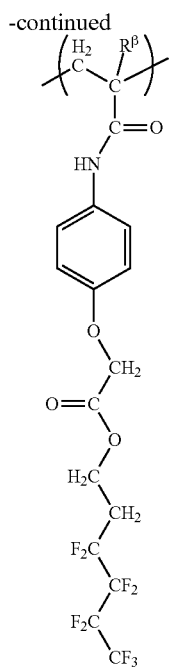

Among the structural units represented by formula (f1-1), specific examples of preferable structural unit containing a silicon atom include a structural unit represented by formula (f1-1) in which $Rf^0$ is a trialkylsilyl group or an organic group having a siloxane bond.

Examples of the trialkylsilyl group include a group represented by formula —$Si(R^{74})(R^{75})(R^{76})$. In the formula, $R^{74}$ to $R^{76}$ each independently represents a linear or branched alkyl group. The alkyl group preferably has 1 to 10 carbon atoms, more preferably 1 to 8, and still more preferably 1 to 5. As the alkyl group, a methyl group, an ethyl group, an isopropyl group or a t-butyl group is preferable, and a methyl group is most preferable.

Specific examples of the trialkylsilyl group include a trimethylsilyl group, a triethylsilyl group, a triisopropylsilyl group and a t-butyldimethylsilyl group.

The organic group containing a trialkylsilyl group may be constituted of only the trialkylsilyl group, or may be a group in which n (n represents an integer of 1 or more) trialkylsily groups bonded to a linking group having a valency of (n+1). As the linking group having a valency of (n+1) in which n represents 1, i.e., a divalent linking group, the same divalent linking groups as those described above for $Y^2$ can be mentioned, and a linear or branched alkyl group having an ether bond or an ester bond inserted is preferable. Examples of the linking group having a valency of (n+1) in which n represents 2 or more include the divalent linking groups in which (n−1) hydrogen atom(s) have been further removed therefrom.

Examples of the organic group containing a siloxane bond (Si—O—Si) include a cyclic siloxane in which a hydrocarbon group is bonded to a silicon atom, polyhedral oligomeric silsesquioxane in which a hydrocarbon group is bonded to a silicon atom, and a group in which part of the carbon chain of a chain-like or cyclic alkyl group has been replaced with —Si—O—Si—. In the cyclic siloxane or the polyhedral oligomeric silsesquioxane, the hydrocarbon group bonded to the silicon atom may be either an alipahtic hydrocarbon group or an aromatic group. An aliphatic group is preferable, and an alkyl group of 1 to 5 carbon atoms is more preferable.

Among these, a structural unit represented by formula (f1-1) in which v is 1 and $X^0$ is a divalent linking group, or a structural unit represented by formula (f1-1) in which v is 0 and $X^0$ is a single bond is preferable.

As the structural unit (f1), at least one member selected from the group consisting of structural units represented by the aforementioned formulae (f1-11) to (f1-14) is preferable, and a structural unit represented by the aforementioned formula (f1-14) is most preferable.

In the component (F), as the structural unit (f1), one type of structural unit may be used alone, or two or more types of structural units may be used in combination.

The component (F) may consist of the structural unit (f1), or have a structural unit other than the structural unit (f1), in addition to the structural unit (f1).

Specific examples of the component (F) include a polymer consisting of a structural unit (f1) (homopolymer); a copolymer of a structural unit (f1) and a structural unit (a1); and a copolymer of a structural unit (f1), a structural unit derived from acrylic acid or methacrylic acid, and a structural unit (a1). Among these, as the component (F), a homopolymer of a structural unit (f1) is preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one type may be used alone, or two or more types may be used in combination.

When the resist composition of the present invention contains the component (F), the amount of the component (F) relative to 100 parts by weight of the component (A) is preferably 1.0 part by weight or more, more preferably 1.0 to 15 parts by weight, still more preferably 1 to 10 parts by weight, and most preferably 1 to 5 parts by weight. When the amount of the component (F) is 1.0 part by weight or more, the receding angle of the resist film can be enhanced, and elution and generation of defects can be effectively reduced. On the other hand, when the amount of the component (F) is 5 parts by weight or less, a good balance can be achieved with the other components.

[Amine; Component (D)]

In the resist composition of the present invention, a nitrogen-containing organic compound component (D) (hereafter, referred to as "component (D)") may be blended.

Since the resist composition of the present invention contains at least the acidic component (J), there is a possibility that, in the resist composition solution, the solubility of the component (A) in an alkali developing solution is increased by the component (J) and the optionally blended component (G). This phenomenon can be suppressed by controlling the component (J) to an appropriate acidity; however, the phenomenon can also be controlled by adding the component (D) to decrease the acidity of the component (J) in the resist composition solution. It is preferable to use the component (D) because the freedom of choice of the material for the component (J) is improved.

In addition, by virtue of the presence of the component (D) during the storage of the resist composition, the storage stability of the resist composition after preparation can be improved. Moreover, at unexposed portions, the change in the solubility of the component (A) by the component (J) mainly proceeds during post exposure bake (PEB). By virtue of the component (D) being removed from the resist film before baking, the component (D) would not impede the increase in the solubility of the component (A) in an alkali developing solution. As a result, excellent lithography properties and pattern shape can be obtained.

A multitude of these components (D) have already been proposed, and any of these known compounds may be used. Among these, as the component (D), a compound exhibiting a pKa which is the same or smaller than the pKa of the cation moiety of the component (J) is preferable. That is, the pKa of the component (J) is preferably 7 or less, more preferably 6 or less, and still more preferably 3 or less.

Further, in the case where an ammonium salt such as the compound (J1) is used as the component (J), and in the case where a component (G) is used, in terms of preventing salt exchange between the component (D) and the cation of the compound (J1) or the cation of the component (G1), it is more preferable that the pKa of the component (D) is the same or smaller than the pKa of the cation of the component (J1) and the cation of the component (G1).

When the resist composition contains the component (G2), in terms of preventing the acidity of the component (G2) from extremely decreasing, the basicity of the component (D) is preferably low, and the pKa of the component (D) is preferably 7 or less, and more preferably 6 or less.

Examples of the component (D) which satisfies such pKa include an amine in which one "$H^+$" bonded to the nitrogen atom (N) has been removed from formula (J1c-1) described in the explanation of the component (J). Specifically, preferable examples include the above-mentioned compounds given as specific examples of formula (J1c-11) and (J1c-13) in which the terminal "$NH_3^+$" has been replaced by "$NH_2$"; and compounds given as specific examples of formula (J1c-12) in which "$NH^+$" within the ring has been replaced by "N".

In addition, the component (D) is preferably an amine having a relatively low boiling point. By virtue of using an amine having a relatively low boiling point, the component (D) can be removed from the resist film during the formation of the resist film on a substrate, i.e., prior to PEB.

As such component (D) which satisfies the above boiling point, an amine having a boiling point of 130° C. or lower is preferable, an amine having a boiling point of 100° C. or lower is more preferable, and an amine having a boiling point of 90° C. or lower is most preferable.

Specific examples of the component (D) which satisfies the above boiling point include aliphatic amine compounds which have a fluorinated alkyl group, such as trifluoroethylamine (2,2,2-trifluoroethylamine), pentafluoropropylamine (2,2,3,3,3-pentafluoropropylamine), heptafluorobutylamine (1H, 1H-heptafluorobutylamine), nonafluoropentylamine (1H, 1H-nonafluoropentylamine), undecafluorohexylamine (1H, 1H-undecafluorohexylamine), bis(2,2,2-trifluoroethyl)amine, bis(2,2,3,3,3-pentafluoropropyl)amine and 1-(2,2,2-trifluoroethyl)pyrrolidine; pyridine compounds, such as pyridine and pentafluoropyridine; and oxazole compounds, such as oxazole and isooxyazole.

As the component (D), one type of compound may be used alone, or two or more types may be used in combination.

When the resist composition of the present invention contains the component (D), the amount of the component (D) relative to 100 parts by weight of the component (A) is preferably within a range from 0.01 to 20.0 parts by weight, more preferably from 1 to 15 parts by weight, and still more preferably from 2 to 10 parts by weight. When the amount of the component (D) is within the above-mentioned range, the storage stability can be improved, thereby improving the lithography properties and the resist pattern shape.

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, dyes, sensitizers and base amplifiers.

As the sensitizer, conventional sensitizers can be used, and specific examples thereof include benzophenone-type sensitizers, such as benzophenone and p,p'-tetramethyldiaminobenzophenone; carbazole-type sensitizers; acetophen-type sensitizers; naphthalene-type sensitizers; phenol-type sensitizers; anthracene-type sensitizers, such as 9-ethoxyanthracene; biacetyl; eosin; rose bengal; pyrene; phenothiazine; and anthrone. In the resist composition, the amount of the sensitizer, relative to 100 parts by weight of the component (A) is preferably from 0.5 to 20 parts by weight.

A base amplifier is decomposed by the action of a base in a chain reaction, and is capable of generating a large amount of base using a small amount of base. Therefore, by blending a base amplifier, the sensitivity of the resist composition can be improved. As the base amplifier, for example, those described in Japanese Unexamined Patent Application, First Publication No. 2000-330270 and Japanese Unexamined Patent Application, First Publication No. 2008-174515 can be used.

<Organic Solvent>

The resist composition used in the present invention can be prepared by dissolving the materials for the resist composition in an organic solvent (hereafter, referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME), cyclohexanone and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2. For example, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3. Alternatively, when PGME and cyclohexanone is mixed as the polar solvent, the PGMEA:(PGME+cyclohexanone) weight ratio is preferably from 1:9 to 9:1, more preferably from 2:8 to 8:2, and still more preferably 3:7 to 7:3.

Further, as the component (S), a mixed solvent of γ-butyrolactone with PGMEA, EL or the aforementioned mixed solvent of PGMEA with a polar solvent, is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate, depending on the thickness of the coating film. In general, the organic solvent is used in an amount such that the solid content of the resist composition becomes within the range from 2 to 20% by weight, and preferably from 2 to 15% by weight.

The compound (J1) used in the resist composition of the present invention is a novel compound.

By virtue of the using the compound (J1) instead of the acid generator component, a resist composition conventionally used in an alkali developing process to form a positive-tone pattern can be used in an alkali developing process to form a negative-tone pattern (solvent developing process to form a positive-tone pattern), thereby increasing choices of the developing solution and the patterns. Further, since a negative-tone pattern can be formed by an alkali developing process, by using an alkali developing solution which is advantageous over an organic developing solution in terms of environment, apparatus and cost, and a conventional base component widely developed, a negative-tone pattern suitable for formation of a fine pattern (an isolated trench pattern, a fine densed pattern or the like) with excellent lithography properties can be formed.

<<Method of Forming a Resist Pattern>>

A second aspect of the present invention is a method of forming a resist pattern, including: using a resist composition containing the component (A) and the component (J) to form a resist film on a substrate, subjecting the resist film to exposure, and subjecting the resist film to developing to form a resist pattern.

Hereinbelow, the method of forming a resist pattern according to the present invention will be specifically described, with reference to the drawings. However, the present invention is not limited to these embodiments.

FIG. 1 shows an example of one embodiment of the method of forming a resist pattern according to the present invention using an alkali developing process.

In this embodiment, a resist composition containing a base component that exhibits increased solubility in an alkali developing solution and a component (J) that is decomposed by exposure to exhibit decreased acidity is used.

Firstly, as shown in FIG. 1A, the resist composition is applied to a substrate 1 to form a resist film 2 (step (1); FIG. 1A).

Next, as shown in FIG. 1(b), the thus formed resist film 2 is subjected to exposure through a photomask 3 having a predetermined pattern formed thereon. As a result, in the exposed region (exposed portions) of the resist film 2, the acidity of the component (J) is decreased by exposure, so that the proton donor ability is deteriorated or impaired (step(2); FIG. 1(b)).

After exposure, baking (post exposure bake (PEB)) is conducted. By this baking, at the unexposed portions 2b of the resist film 2, the solubility of the base component in an alkali developing solution can be increased by the action of the component (J), since the acidity of the component (J) within the resist film is not decreased. On the other hand, at exposed portions 2a, since the acidity of the component (J) is decreased, the solubility of the base component (A) in an alkali developing is either unchanged or only slightly changed.

As a result, a difference in the dissolution rate in an alkali developing solution (dissolution contrast) occurs between the exposed portions 2a and the unexposed portions 2b (step (3); FIG. 1(c)).

Thereafter, developing is conducted using an alkali developing solution. By conducting development, the exposed portions 2a of the resist film 2a remains, and the unexposed portions 2b of the resist film 2 are dissolved and removed. As a result, as shown in FIG. 1D, a negative-tone resist pattern composed of exposed portions 2a is formed on the substrate 1.

[Step (1)]

In this embodiment, a resist composition containing a base component (A) that exhibits increased solubility in an alkali developing solution and a component (J) that is decomposed by exposure to exhibit decreased acidity is applied to the substrate 1 to form a resist film 2.

The resist composition is the same as defined in the first aspect.

The substrate 1 is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate 1, any one of the above-mentioned substrates provided with an inorganic and/or organic film on the surface thereof may be used, and a substrate provided with an organic film is preferable. As the inorganic film, an inorganic antireflection film (inorganic BARC) can be used. As the organic film, an organic antireflection film (organic BARC) and an organic film such as a lower-layer organic film used in a multilayer resist method can be used. It is particularly desirable that an organic film is provided because a pattern can be reliably formed on the substrate with a high aspect ratio which is useful in the production of semiconductors.

Here, a "multilayer resist method" is method in which at least one layer of an organic film (lower-layer film) and at least one layer of a resist film are provided on a substrate, and a resist pattern formed on the upper resist film is used as a mask to conduct patterning of the lower-layer film. This method is considered as being capable of forming a pattern with a high aspect ratio. The multilayer resist method is broadly classified into a method in which a double-layer structure consisting of an upper-layer resist film and a lower-layer film is formed, and a method in which a multilayer structure having at least three layers composed of an upper-layer resist film, a lower-layer film and at least one intermediate layer (thin metal film or the like) provided between the upper-layer resist film and the lower-layer film. In the multilayer resist method, a desired thickness can be ensured by the lower-layer film, and as a result, the thickness of the resist film can be reduced, and an extremely fine pattern with a high aspect ratio can be formed.

An inorganic film can be formed, for example, by coating an in organic anti-reflection film composition such as a silicon-based material on a substrate, followed by baking.

An organic film can be formed, for example, by dissolving a resin component and the like for forming the film in an organic solvent to obtain an organic film-forming material, coating the organic film-forming material on a substrate using a spinner or the like, and baking under heating conditions preferably in the range of 200 to 300° C. for 30 to 300 seconds, more preferably for 60 to 180 seconds. The organic film-forming material does not need to have susceptibility to light or electron beam like a resist film, and the organic film-forming material may or may not have such susceptibility. More specifically, a resist or a resin generally used in the production of a semiconductor device or a liquid crystal display device can be used.

Further, it is preferable that the organic film-forming material can be subjected to etching, particularly dry etching, so that, by etching the organic film using a resist pattern, the resist pattern can be transferred to the organic film, and an organic film pattern can be formed. It is particularly desirable to use an organic film-forming material which can be subjected to oxygen plasma etching or the like. As such an organic film-forming material, a material conventionally used for forming an organic film such as an organic BARC can be used. Examples of such an organic film-forming material include the ARC series manufactured by Brewer Science Ltd., the AR series manufactured by Rohm and Haas Company, and the SWK series manufactured by Tokyo Ohka Kogyo Co., Ltd.

The method of applying the resist composition to the substrate 1 to form a resist film 2 is not particularly limited, and the resist film 2 can be formed by a conventional method.

For example, the resist composition can be applied to the substrate 1 by a conventional method using a spinner or the like to form a coating film on the substrate 1, followed by drying, thereby forming a resist film 2.

Drying the coating film can be conducted so as to volatilize the organic solvent (resist solvent) contained in the coating film, and examples of the drying method include a method of conducting prebaking (PAB), and a method of drying at room temperature on a cooling plate.

The prebaking temperature is preferably 70 to 140° C., more preferably 70 to 130° C., and still more preferably 70 to 120° C.

The prebaking time is preferably 40 to 120 seconds, and more preferably 60 to 90 seconds.

By conducting prebaking, the organic solvent can be volatilized even when the resist film has a large film thickness. On the other hand, by drying the resist composition at room temperature and not conducting prebaking, the number of steps in the formation of a resist pattern can be reduced, and the resolution of the resist pattern can be enhanced.

Whether or not a prebaking is conducted can be suitably determined depending on the advantages in view of the materials used for the resist composition, and target of the pattern to be formed.

Further, in the present invention, the component (J) present over the entire surface of the resist film after coating is capable of changing the solubility of the base component in an alkali developing solution. Therefore, after coating and before exposure, it is preferable not to change the solubility of the base component by the action of the component (J). By heating, the change in the solubility of the base component by acid (component (J)) is promoted. Therefore, by not conducting prebaking, the contrast between the exposed portions 2a and the unexposed portions 2b of the resist film 2 can be enhanced, and a negative-tone pattern can be formed with a high resolution.

The film thickness of the resist film 2 formed in step (1) is preferably within the range from 50 to 500 nm, and more preferably from 50 to 450 nm. By ensuring that the thickness of the resist film satisfies the above-mentioned range, a resist pattern with a high level of resolution can be formed, and a satisfactory level of etching resistance can be achieved.

Further, in the case where a prebaking is not conducted, the film thickness of the resist film 2 formed in step (1) is preferably 300 nm or less, more preferably 200 nm or less, and most preferably from 50 to 150 nm. When the film thickness of the resist film 2 is 300 nm or less, by a coating method such as a spin-coating method at room temperature without prebaking, the organic solvent is less likely to remain in the resist film, and the resist film can be more reliably dried, thereby improving the uniformity of the film thickness of the resist film 2 (i.e., the in-plane uniformity of the substrate 1).

[Step (2)]

In the present embodiment, the resist film 2 formed in the step (1) is selectively exposed through a photomask 3. As a result, at exposed portions 2a, the acidicty of the component (J) is decreased by exposure, so that the proton donor ability is deteriorated or impaired.

With respect to the exposure dose, an amount capable of decomposing the component (J) present at exposed portions 2a to exhibit decreased acidity and obtaining a contrast between exposed portions 2a and unexposed portions 2b is sufficient.

The wavelength to be used for exposure is not particularly limited and the exposure can be conducted using radiation such as KrF excimer laser, ArF excimer laser, $F_2$ excimer laser, extreme ultraviolet rays (EUV), vacuum ultraviolet rays (VUV), electron beam (EB), X-rays, and soft X-rays. In terms of forming a fine resist pattern, ArF excimer laser, EUV or EB is preferable, and ArF excimer laser is particularly desirable.

The photomask 3 is not particularly limited, and a conventional mask can be used. For example, a binary mask in which the transmittance of the light shielding portion is 0% or a halftone-phase shift mask (HT-mask) in which the transmittance of the light shielding portion is 6% can be used. The unexposed portions can be selectively formed by using a halftone-phase shift mask.

As a binary mask, those in which a chromium film, a chromium oxide film, or the like is formed as a light shielding portion on a quartz glass substrate are generally used.

A phase shift mask is a photomask provided with a portion (shifter) which changes the phase of light. Thus, by using a phase shift mask, incidence of light to unexposed portions can be suppressed, and the dissolution contrast to an alkali developing solution can be improved between unexposed portions and exposed portions. As a phase shift mask other than a halftone-phase shift mask, a Levenson-phase shift mask can be mentioned. As any of these phase shift masks, commercially available masks can be used.

Specific examples of the half-tone type phase shift masks include those in which an MoSi (molybdenum silicide) film, a chromium film, a chromium oxide film, an silicon oxynitride film, or the like is formed as a light shielding portion (shifter) exhibiting a transmittance of about several 10% (generally 6%) on a substrate generally made of quartz glass.

In the present embodiment, exposure is conducted through a photomask 3, but the present invention is not limited to this embodiment. For example, the exposure may be conducted without using a mask, e.g., selective exposure by drawing with electron beam (EB) or the like.

In the case where the resist composition of the present invention contains, in addition to the component (J), a component that generates base upon exposure, base is generated from the photobase generator in step (2). Examples of the component that generates base upon exposure include a resin component having a group that generates base upon exposure (e.g., a resin component having the structural unit (a5)), and the aforementioned component (C).

Specifically, by the exposure in step (2), at exposed portions 2a, the acidity of the component (J) is decreased, and base is generated from the component that generates base upon exposure. As a result, at exposed portions 2a, a neutralization reaction between decomposed acidic compound exhibiting decreased acidity or undecomposed component (J) with the base generated from the component that generates base upon exposure proceeds, so that the solubility of the base component in an alkali developing is either unchanged or only slightly changed. On the other hand, at unexposed portions 2b, the acidity of the component (J) is not decreased, and no base is generated from the component that generates base upon exposure. As such, a difference in the dissolution rate in an alkali developing solution (dissolution contrast) occurs between the exposed portions 2a and the unexposed portions 2b.

In the method of forming a resist pattern according to the present embodiment, since a satisfactory dissolution contrast can be obtained by the decrease in the acidity of the component (J) upon exposure, the resist composition may or may not contain a component that generates base upon exposure.

The exposure of the resist film 2 can be either a general exposure (dry exposure) conducted in air or an inert gas such as nitrogen, or immersion exposure (immersion lithography) through an immersion medium. In step (2), in terms of forming a resist pattern with a high resolution, it is preferable to conduct immersion exposure through an immersion medium.

In immersion lithography, exposure (immersion exposure) is conducted in a state where the region between the lens and the resist film 2 formed on the substrate 1 (which was conventionally filled with air or an inert gas such as nitrogen) is filled with a solvent (a immersion medium) that has a larger refractive index than the refractive index of air.

More specifically, in immersion lithography, the region between the resist film 2 formed in the above-described manner and lens at the lowermost portion of the exposure apparatus is filled with a solvent (an immersion medium) that has a larger refractive index than the refractive index of air, and in this state, the resist film 2 is subjected to exposure (immersion exposure) through a predetermined photomask 3.

The immersion medium preferably exhibits a refractive index larger than the refractive index of air but smaller than the refractive index of the resist film 2 to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film 2 include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the immersion medium after the exposure can be removed by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

It is preferable that the step (2) includes an operation in which a latent image of a first line and space pattern is formed by subjecting the resist film 2 to a first exposure through a photomask 3, and a latent image of a second line and space pattern is formed so as to intersect with the first line and space pattern by subjecting the resist film to a second exposure through the photomask 3 (i.e., a double patterning method).

The term "latent image" refers to a region of the resist film where the radiation transmitted through the transmission part of the photomask has been irradiated (i.e., exposed portion).

By conducting such an operation, a lattice-like latent image is formed on the resist film 2 in which the linear latent images of the first line and space pattern intersect with the latent images of the second line and space pattern. Next, after the step (3), by performing the step (4) on the resist film (2), the regions where a latent image is not formed (unexposed portions) are dissolved and removed, whereas the exposed portions are not removed and retained, thereby forming a fine, densed hole pattern.

[Step (3)]

In the present embodiment, after the step (2), baking (post exposure bake (PEB)) is conducted.

In the baking, the temperature conditions is preferably from 50 to 200° C., more preferably from 80 to 150° C., and still more preferably from 90 to 130° C. The baking time is preferably from 10 to 300 seconds, more preferably from 40 to 120 seconds, and still more preferably from 60 to 90 seconds.

In this manner, by conducting baking of the resist film 2 after exposure, at the unexposed portions 2b of the resist film 2, the solubility of the base component in an alkali developing solution can be increased by the action of the undecomposed component (J) which has the acidity thereof not decreased. On the other hand, at exposed portions 2a, since the acidity of the component (J) is decreased by exposure, the reaction does not satisfactorily proceed, and the solubility of the base component (A) in an alkali developing is either unchanged or only slightly changed. As such, a difference in the dissolution rate in an alkali developing solution (dissolution contrast) occurs between the exposed portions 2a and the unexposed portions 2b.

By generation of such dissolution contrast, a high-resolution negative-tone resist pattern can be obtained by alkali developing in step (4).

[Step (4)]

In the present embodiment, after the step (3), by conducting alkali developing, the unexposed portions 2b of the resist film 2 are dissolved and removed, and the exposed portions 2a are retained, thereby forming a negative resist pattern.

Specific examples of the alkali developing solution include inorganic alkalis, such as sodium hydroxide, potassium hydroxide, sodium carbonate, sodium silicate, sodium metasilicate and aqueous ammonia; primary amines, such as ethylamine and n-propyl amine; secondary amines, such as diethylamine and di-n-butylamine; tertiary amines, such as triethylamine and methyldiethylamine; alcoholamines, such as dimethylethanolamine and triethanolamine; quaternary ammonium salts, such as tetramethylammonium hydroxide and tetraethylammonium hydroxide; and cyclic amines, such as pyrrole and piperidine.

Among these examples, as the alkali developing solution, an aqueous alkali solution containing at least one member selected from the group consisting of primary amines, secondary amines, tertiary amines and quaternary ammonium salts is preferable, and an aqueous solution of tetramethylammonium hydroxide (TMAH) is particularly desirable.

Further, the aforementioned aqueous alkali solution having alcohols, surfactants added thereto in an appropriate amount may be used.

In general, the alkali concentration within the alkali developing solution (i.e., concentration of inorganic alkalis, quaternary ammonium salts or amine compounds, based on the total weight of the alkali developing solution) is from 0.01 to 20% by weight.

The alkali developing treatment can be performed by a conventional method.

After the alkali development, a rinse treatment using pure water or the like may be conducted.

In addition, after the alkali development, a further baking (post bake) may be conducted. Post bake (which is performed in order to remove water content after the alkali developing and rinsing) is generally conducted at about 100° C. preferably for 30 to 90 seconds.

The method of forming a resist pattern according to the present invention has been described with the above embodiment, but the present invention is not limited thereto.

For example, in the above embodiment, since the acid concentration is increased at unexposed portions 2b by conducting baking treatment such as PEB, the aforementioned component (H) may be used in combination with the component (J).

Further, in the above embodiment, an example of using an alkali developing solution was illustrated; however, a solvent developing using an organic developing solution may be conducted instead of alkali developing. By conducting solvent developing, unexposed portions of the resist film remain, and the exposed portions are dissolved and removed by the organic developing solution, thereby forming a positive-tone resist pattern composed of the unexposed portions on the substrate.

As the organic solvent, any of the conventional organic solvents can be used which are capable of dissolving the component (A) (prior to exposure). Specific examples of the organic solvent include polar solvents such as ketone solvents, ester solvents, alcohol solvents, amide solvents and ether solvents, and hydrocarbon solvents. Among these, ester solvents are preferable. As an ester solvent, butyl acetate is preferable.

In the method of forming a resist pattern according to the present invention, after forming a resist pattern in the manner as described above, etching of the substrate 1 may be conducted using the resist pattern as a mask. By conducting such etching to transfer the resist pattern to the substrate 1, a semiconductor device or the like can be produced.

The etching can be conducted by a conventional method. For example, when the substrate 1 has an organic film formed thereon, the etching of the organic film is preferably conducted by dry etching. Among dry etching, especially in terms of production efficiency, oxygen-plasma etching or etching using a $CF_4$ gas or a $CHF_3$ gas is preferable, and oxygen-plasma etching is more preferable.

Etching of the substrate is preferably performed using a halogen gas, more preferably using a fluorinated carbon-based gas, and most preferably using a $CF_4$ gas or a $CHF_3$ gas.

According to the method of forming a resist pattern of the present invention, a negative-tone resist pattern can be formed with a high resolution and excellent lithography properties by a developing process in which a chemically amplified resist composition conventionally known as a positive type is used in combination with an alkali developing solution. Thus, according to the method of forming a resist pattern of the present invention, a resist pattern (such as an isolated trench pattern, an extremely small, dense contact hole pattern, or the like) having a region where the optical strength becomes weak (region where irradiation by exposure is not satisfactorily reached) is likely to be generated in a film thickness direction can be formed with a high resolution. Further, by the method of forming a resist pattern according to the present invention, it is possible to form a highly densed resist pattern. For example, it becomes possible to form a contact hole pattern in which each of the holes are close to each other with excellent shapes, e.g., the distance between the holes is about 30 to 50 nm.

Further, a positive-tone resist pattern can be formed with a high resolution and excellent lithography properties by a developing process in which a chemically amplified resist composition conventionally known as a positive type is used in combination with an organic developing solution.

Furthermore, the method of forming a resist pattern according to the present invention can be performed by existing exposure apparatuses and existing chemically amplified resist compositions.

<<Compound>>

The compound according to a third aspect of the present invention is a compound represented by general formula (i1) shown below (hereafter, this compound is referred to as "compound (i1)").

[Chemical Formula 88]

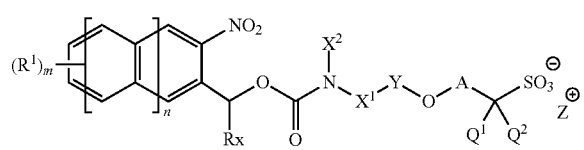

(i1)

In the formula, $R^1$ represents a hydrogen atom, a hydroxy group, a halogen atom, a linear or branched alkoxy group, a hydrocarbon group which may have a substituent, or a nitro group; m represents an integer of 0 to 4; n represents an integer of 0 to 3; Rx represents a hydrogen atom or a hydrocarbon group which may have a substituent; $X^1$ represents a divalent linking group and $X^2$ represents a hydrogen atom or a hydrocarbon group which may have a substituent, provided that $X^1$ and $X^2$ may be mutually bonded to form a ring with the nitrogen atom; Y represents a single bond or a carbonyl group, and A represents an alkylene group of 1 to 6 carbon atoms, provided that part of the methylene group constituting the alkylene group may be replaced with an oxygen atom or a carbonyl group, part or all of the hydrogen atoms constituting the alkylene group may be substituted with an aliphatic hydrocarbon group of 1 to 6 carbon atoms which may have a fluorine atom, and —Y—O—A— does not represent —C(=O)—O—C(=O)—; $Q^1$ and $Q^2$ each independently represents a fluorine atom or a linear or branched fluorinated alkyl group of 1 to 6 carbon atoms; and $Z^+$ represents a metal cation or an onium cation.

In formula (i1), $R^1$, m, n, Rx, $X^1$, $X^2$, Y, A, $Q^1$ and $Q^2$ are the same as defined for $R^1$, m, n, Rx, $X^1$, $X^2$, Y, A, $Q^1$ and $Q^2$ in formula (J1). $Z^+$ represents a metal cation or an onium cation, and examples thereof include an alkali metal cation, an organic ammonium ion and other organic cations.

Examples of alkali metal ions include a sodium ion, a lithium ion and a potassium ion, and a sodium ion or a lithium ion is preferable.

The organic ammonium ion is the same as defined for $W^+$ in the aforementioned formula (J1).

Examples of organic cations other than organic ammonium ions include organic cations used as the cation moiety of an onium salt acid generator for a conventional chemically amplified resist composition.

In the case where $Z^+$ is an ammonium cation which satisfies the requirements of $W^+$ in formula (J1), the compound of the present invention is a novel compound useful as an acidic compound for the resist composition according to the first aspect.

Alternatively, in the case where $Z^+$ is an ammonium cation which does not satisfy the requirements of $W^+$ in formula (J1), or in the case where $Z^+$ is a metal cation or other organic cation, the compound of the present invention is a novel compound useful as a precursor of an acidic compound for the resist composition according to the first aspect. In such cases, by conducting a conventional method to perform a salt exchange between $Z^+$ and $W^+$, an acidic compound for the resist composition can be produced from the precursor compound.

(Production Method of Compound)

The production method of the compound (i1) of the present invention is not particularly limited, and for example, the following methods can be mentioned. Hereafter, a compound represented by formula (1-1) is referred to as "compound (1-1)", and the same applies for compounds represented by other formulae.

(1) A method in which a compound (1-1) having a halogen atom or a functional group L exhibiting an elimination ability on the terminal thereof is reacted with a compound (1-2) having a hydroxy group on the terminal thereof, thereby obtaining a compound (i1).

(2) A method in which a compound (2-1) having a hydroxy group on the terminal thereof is reacted with a compound (2-2) having a hydroxy group on the terminal thereof, thereby obtaining a compound (i1).

(3) A method in which a compound (3-1) having a hydroxy group on the terminal thereof is reacted with a compound (3-2) having a halogen atom or a functional group L exhibiting an elimination ability on the terminal thereof, thereby obtaining a compound (i1).

[Chemical Formula 89]

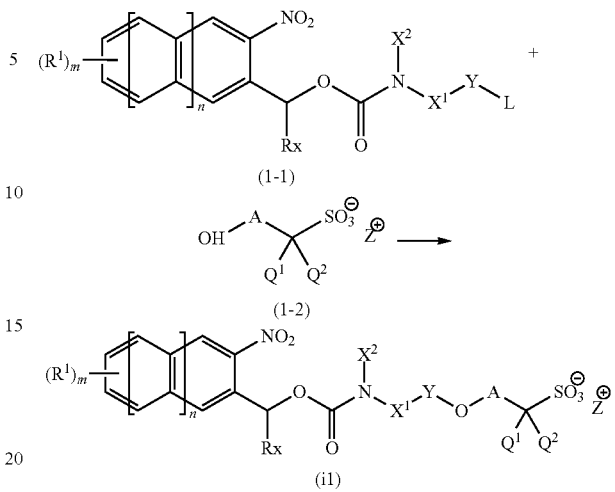

[Chemical Formula 90]

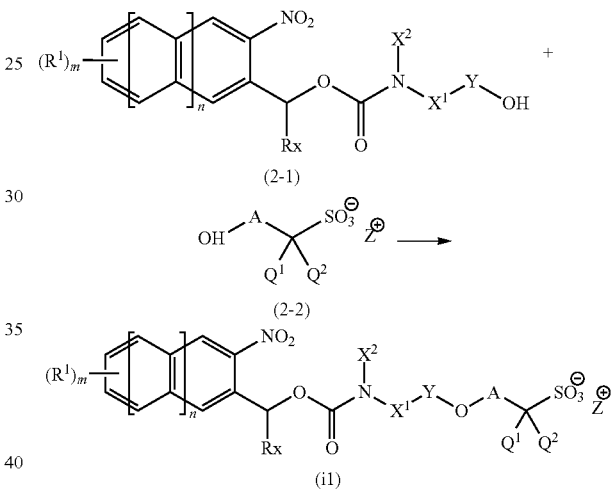

[Chemical Formula 91]

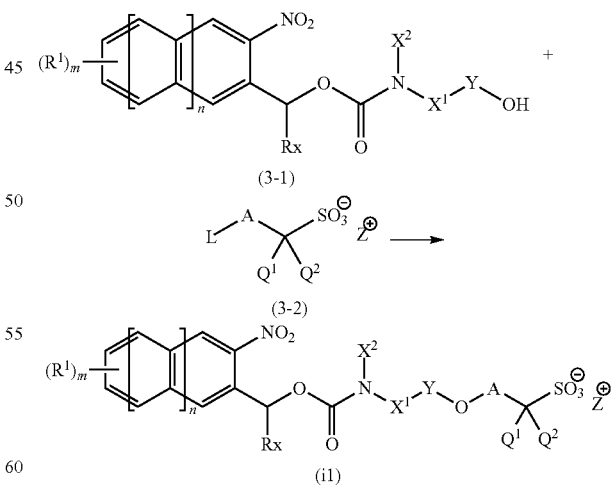

In formulae (1-1), (1-2), (2-1), (2-2), (3-1), (3-2) and (i1), $R^1$, m, n, Rx, $X^1$, $X^2$, Y, A, $Q^1$, $Q^2$ and $Z^+$ are the same as defined above. L represents a halogen atom or a functional group exhibiting an elimination ability. Examples of the halogen atom include a chlorine atom, a bromine atom and an iodine atom. Examples of the functional group exhibiting an elimination ability include a tosyl group.

In the method (1) to (3) above, the reaction between the compounds (1-1) and (1-2), the reaction between the compounds (2-1) and (2-2) and the reaction between the compounds (3-1) and (3-2) can be performed, for example, as follows.

Two types of compounds are dissolved in an appropriate organic solvent such as pyridine, and a dehydration/condensation agent such as diisopropylcarbodiimide is dropwise added thereto if desired, followed by stirring to conduct a reaction. The reaction temperature is preferably within the range of 10 to 30° C., and more preferably 18 to 25° C. The reaction time is preferably 6 to 100 hours, and more preferably 20 to 80 hours.

Further, in the case where $Z^+$ in the compound (i1) is not $W^+$, a compound (J1) can be produced by a salt exchange reaction as follows. In the formulae, $R^1$, m, n, Rx, $X^1$, $X^2$, Y, A, $Q^1$, $Q^2$, $Z^+$ and $W^+$ are the same as defined above. $B^-$ represents a counter anion exhibiting a pKa larger than $-C(Q^1)(Q^2)-SO_3^-$ in formula (i1), and examples thereof include a bromide ion, a chloride ion, p-toluenesulfonate ion, a methanesulfonate ion and a benzenesulfonate ion.

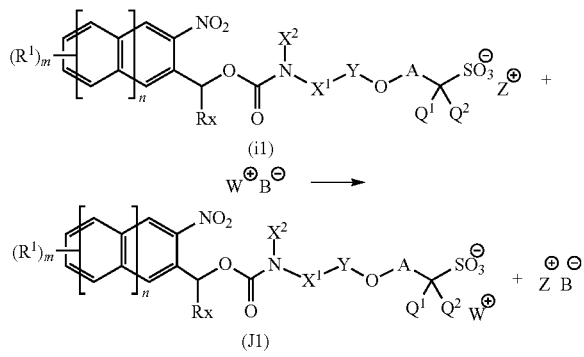

The structure of the compound (i1) or the compound (J1) obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

EXAMPLES

As follows is a description of examples of the present invention, although the scope of the present invention is by no way limited by these examples.

In the NMR analysis of the present examples, the chemical shift standard for $^1$H-NMR was tetramethylsilane (TMS), and the chemical shift standard for $^{19}$F-NMR was trichlorofluoromethane (the peak of hexafluorobenzene was regarded as $-160$ ppm).

Synthesis Example 1

In a nitrogen atmosphere, 30.8 g of (i)-1, 20.3 g of (i)-2 and 250 g of pyridine were added. Then, 16.41 g of diisopropylcarbodiimide was gradually added in a dropwise manner. Thereafter, the resultant was stirred at room temperature for 24 hours, and 500 g of pure water was added to finish the reaction. Diisopropylurea precipitated in the reaction mixture was removed by filtration, and 26 g of 1H,1H-heptafluorobutylaminechloride was added to the filtrate, followed by stirring at room temperature for 1 hour. Then, the precipitate was collected by filtration. The obtained powder was dried under reduced pressure, thereby obtaining 52.7 g of a compound (J)-1 in the form of light brown crystals.

The obtained compound was analyzed by NMR, and the structure thereof was identified by the following results.

$^1$H-NMR (400 MHz, DMSO-d6):δ (ppm)=8.79 (3H, NH3), 8.09 (1H, ArF), 7.81 (1H, ArH), 7.65 (2H, ArH), 5.41 (2H, CH2Ar), 4.61 (2H, CH2CF2), 4.02 (2H, CH2NH3), 3.91 (2H, Piperidine), 3.01 (2H, Piperidine), 2.71 (1H, Piperidine), 1.89 (2H, Piperidine), 1.53 (2H, Piperidine).

$^{19}$F-NMR (376 MHz, DMSO-d6):δ(ppm)=−77.5, −111.4, −114.3, −124.6.

[Chemical Formula 93]

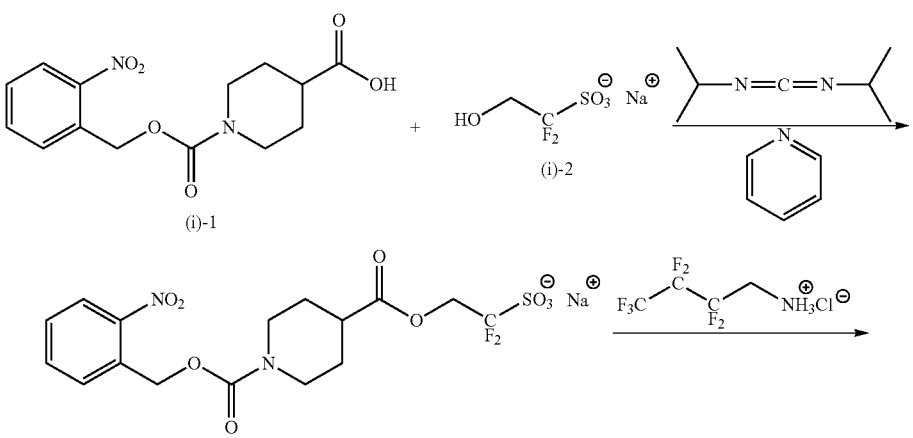

-continued

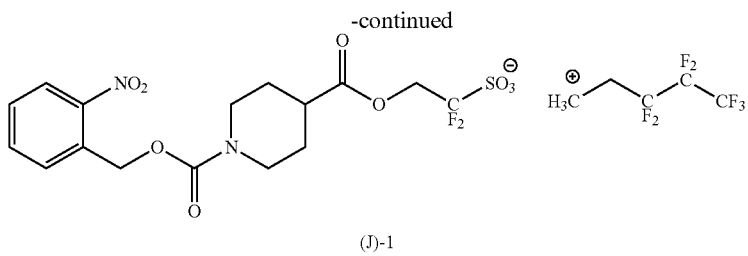

(J)-1

Examples 1 to 13, Comparative Examples 1 and 2

The components shown in Table 1 were mixed together and dissolved to obtain resist compositions.

(D)-2: pyrimidine [pKa=1.78]

(F)-1: a compound represented by chemical formula (F)-1 shown below [Mw: 20,000, Mw/Mn: 1.8. l=100 (molar ratio)].

TABLE 1

| | Component (A) | | Component (J) | Component (C) | Component (G) | Component (D) | Component (F) | Component (S) |
|---|---|---|---|---|---|---|---|---|
| Ex. 1 | (A)-1 [50] | (A)-2 [50] | (J)-1 [5.0] | — | (G1)-1 [10] | (D)-1 [4] | (F)-1 [3] | (S)-1 [3000] |
| Ex. 2 | (A)-1 [50] | (A)-2 [50] | (J)-1 [5.0] | — | (G1)-1 [10] | (D)-2 [2] | (F)-1 [3] | (S)-1 [3000] |
| Ex. 3 | (A)-2 [100] | — | (J)-1 [10.0] | — | — | (D)-2 [2] | (F)-1 [3] | (S)-1 [3000] |
| Ex. 4 | (A)-2 [100] | — | (J)-1 [10.0] | — | — | — | (F)-1 [3] | (S)-1 [3000] |
| Ex. 5 | (A)-2 [100] | — | (J)-1 [5.0] | (C)-1 [10] | (G1)-1 [10] | (D)-1 [4] | (F)-1 [3] | (S)-1 [3000] |
| Ex. 6 | (A)-1 [50] | (A)-2 [50] | (J)-2 [4.08] | — | (G1)-1 [10] | (D)-1 [4] | (F)-1 [3] | (S)-1 [3000] |
| Ex. 7 | (A)-1 [50] | (A)-2 [50] | (J)-3 [4.75] | — | (G1)-1 [10] | (D)-1 [4] | (F)-1 [3] | (S)-1 [3000] |
| Ex. 8 | (A)-1 [50] | (A)-2 [50] | (J)-4 [5.58] | — | (G1)-1 [10] | (D)-1 [4] | (F)-1 [3] | (S)-1 [3000] |
| Ex. 9 | (A)-1 [50] | (A)-2 [50] | (J)-5 [4.80] | — | (G1)-1 [10] | (D)-1 [4] | (F)-1 [3] | (S)-1 [3000] |
| Ex. 10 | (A)-1 [50] | (A)-2 [50] | (J)-6 [5.93] | — | (G1)-1 [10] | (D)-1 [4] | (F)-1 [3] | (S)-1 [3000] |
| Ex. 11 | (A)-1 [50] | (A)-2 [50] | (J)-7 [5.35] | — | (G1)-1 [10] | (D)-1 [4] | (F)-1 [3] | (S)-1 [3000] |
| Ex. 12 | (A)-1 [50] | (A)-2 [50] | (J)-8 [5.51] | — | (G1)-1 [10] | (D)-1 [4] | (F)-1 [3] | (S)-1 [3000] |
| Ex. 13 | (A)-1 [50] | (A)-2 [50] | (J)-9 [5.40] | — | (G1)-1 [10] | (D)-1 [4] | (F)-1 [3] | (S)-1 [3000] |
| Comp. Ex. 1 | (A)-1 [50] | (A)-2 [50] | — | — | (G1)-1 [10] | (D)-1 [4] | (F)-1 [3] | (S)-1 [3000] |
| Comp. Ex. 2 | (A)-2 [100] | — | — | (C)-1 [10] | (G1)-1 [10] | (D)-1 [4] | (F)-1 [3] | (S)-1 [3000] |

In Table 1, the values in brackets [ ] indicate the amount (in terms of parts by weight) of the component added, and the reference characters indicate the following. The pKa values shown below are simulation values determined by ACD/Labs.

(A)-1: a copolymer represented by chemical formula (A)-1 shown below [Mw: 7,000, Mw/Mn: 1.73. l/m/n=45/45/10 (copolymer compositional ratio (molar ratio)).]

(A)-2: a copolymer represented by chemical formula (A)-2 shown below [Mw: 7,000, Mw/Mn: 1.70. l/m=50/50 (copolymer compositional ratio (molar ratio)).]

(J)-1: the aforementioned compound (J)-1

(J)-2 to (J)-9: compounds represented by chemical formulae (J)-2 to (J)-9 shown below (C)-1: a compound represented by chemical formula (C)-1 shown below.

(G1)-1: a compound represented by chemical formula (G1)-1 shown below [cation pKa=5.89, anion pKa=−11.55]

(D)-1: 1H,1H-heptafluorobutylamine [pKa=5.89]

(S)-1: a mixed solvent of PGMEA/PGME=8/2 (weight ratio)

[Chemical Formula 94]

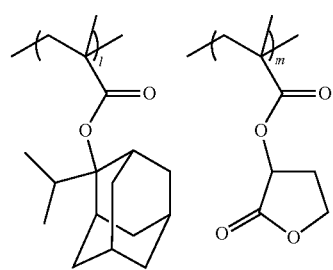

(A)-1

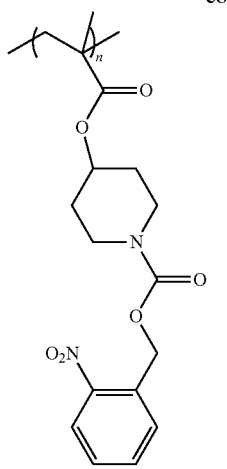
(A)-2
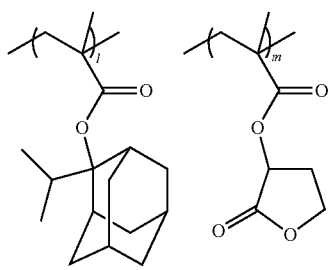
[Chemical Formula 95]
(J)-2
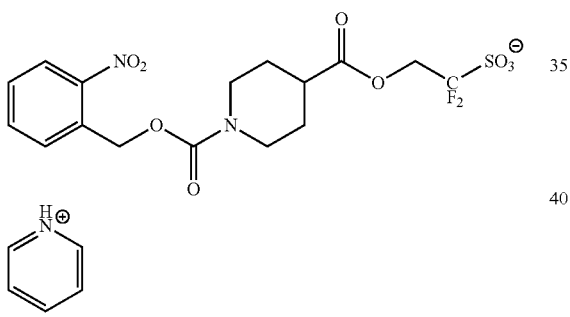
(J)-3
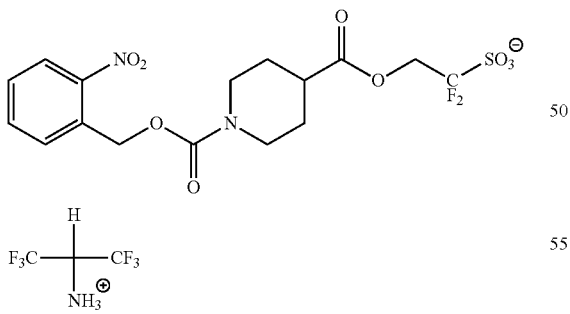
(J)-4
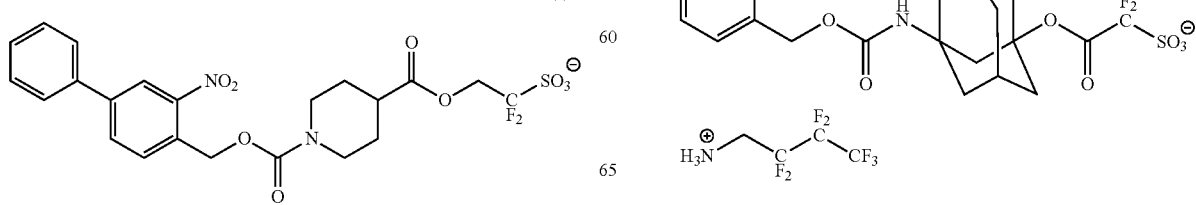
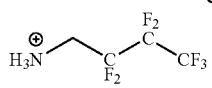
(J)-5
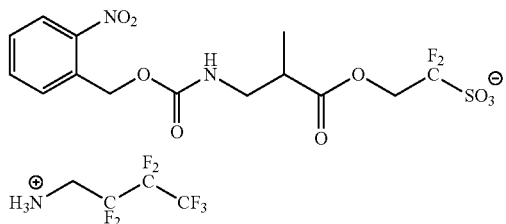
[Chemical Formula 96]
(J)-6
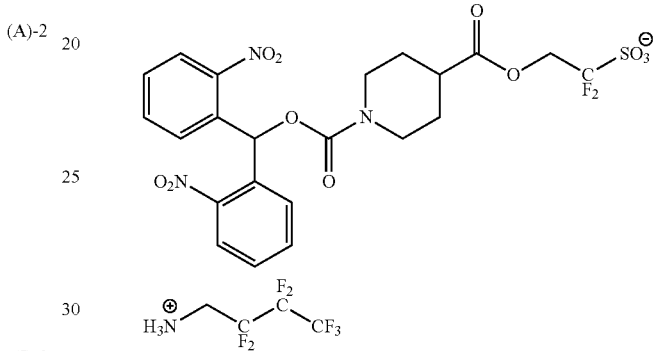
(J)-7
(J)-8
(J)-9

[Chemical Formula 97]

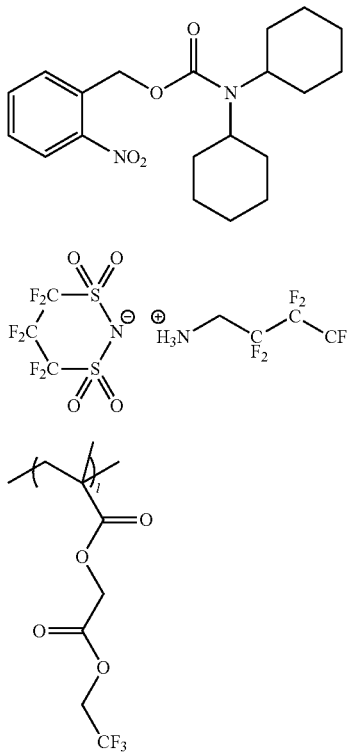

<Formation of Resist Pattern>

An organic anti-reflection film composition (product name: ARC95, manufactured by Brewer Science Ltd.) was applied to an 12-inch silicon wafer using a spinner, and the composition was then baked at 205° C. for 60 seconds, thereby forming an organic anti-reflection film having a film thickness of 90 nm.

Each resist composition was then applied to the organic anti-reflection film using a spinner, and then allowed to stand on a cooling plate for 60 seconds, thereby forming a resist film having a film thickness of 100 nm.

Subsequently, the resist film was selectively irradiated with an ArF excimer laser (193 nm) through a mask, using an immersion lithography ArF exposure apparatus NSR-S609B (manufactured by Nikon Corporation; NA (numerical aperture)=1.07; Crosspole (in/out=0.78/0.97); immersion medium: water).

Next, a PEB treatment was conducted at 90° C. for 60 seconds, followed by development for 20 seconds at 23° C. in a 2.38 wt % TMAH aqueous solution (product name: NMD-W; manufactured by Tokyo Ohka Kogyo Co., Ltd.). Then, the resist film was rinsed for 30 seconds with pure water, followed by drying by shaking. Further, a post bake was conducted on a hot plate at 100° C. for 60 seconds.

As a result, in each of the examples, a contact hole pattern in which holes having a diameter of 60 nm were equally spaced at a pitch of 120 nm was formed (hereafter, this contact hole pattern is referred to as "CH pattern").

[In-Plane Uniformity (CDU) of Pattern Size]

With respect to each CH pattern having the above target size obtained above, 100 holes in the CH pattern were observed from the upper side thereof using a measuring scanning electron microscope (SEM) (product name: S-9380, manufactured by Hitachi High-Technologies Corporation; acceleration voltage: 500V), and the hole diameter (nm) of each hole was measured. From the results, the value of 3 times the standard deviation σ (i.e., 3σ) was determined. The results are indicated "CDU" in Table 2.

The smaller the thus determined 3σ value is, the higher the level of the dimension uniformity (CD uniformity) of the plurality of holes formed in the resist film.

[Evaluation of Resolution]

Under the same conditions, a CH pattern having a diameter of 50 nm (pitch: 100 nm) was formed. With respect to the formed CH pattern, 25 holes in the CH pattern were observed from the upper side thereof using a measuring scanning electron microscope (SEM) (product name: S-9380, manufactured by Hitachi High-Technologies Corporation; acceleration voltage: 500V). When all of the 25 holes were formed, the resolution was evaluated as "A", and when one or more of the 25 holes was covered, the resolution was evaluated as "B". The results are shown in Table 2.

TABLE 2

|  | CDU (nm) | 50 nm resolution |
| --- | --- | --- |
| Ex. 1 | 11.8 | A |
| Ex. 2 | 11.2 | A |
| Ex. 3 | 12.3 | A |
| Ex. 4 | 12.0 | A |
| Ex. 5 | 12.1 | A |
| Ex. 6 | 13.5 | A |
| Ex. 7 | 11.7 | A |
| Ex. 8 | 11.6 | A |
| Ex. 9 | 12.2 | A |
| Ex. 10 | 12.8 | A |
| Ex. 11 | 11.1 | A |
| Ex. 12 | 12.5 | A |
| Ex. 13 | 13.6 | A |
| Comp. Ex. 1 | 14.2 | B |
| Comp. Ex. 2 | 15.0 | B |

From the results shown above, it was confirmed that, in the case where the resist compositions of Examples 1 to 13 according to the present invention were used, lithography properties such as CDU and resolution were excellent as compared to the case where the resist compositions of Comparative Examples 1 and 2 which do not contain a component (J) were used.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition comprising a base component (A) which exhibits changed solubility in a developing solution, and an acidic compound component (J) which is decomposed by exposure to exhibit decreased acidity, wherein the acidic compound component (J) comprises a compound represented by general formula (J1) shown below:

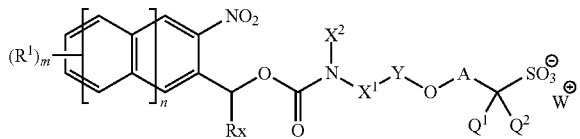

(J1)

wherein R¹ represents a hydrogen atom, a hydroxy group, a halogen atom, a linear or branched alkoxy group, a hydrocarbon group which may have a substituent, or a nitro group; m represents an integer of 0 to 4; n represents an integer of 0 to 3; Rx represents a hydrogen atom or a hydrocarbon group which may have a substituent; X¹ represents a divalent linking group and X² represents a hydrogen atom or a hydrocarbon group which may have a substituent, provided that X¹ and X² may be mutually bonded to form a ring with the nitrogen atom; Y represents a single bond or a carbonyl group, and A represents an alkylene group of 1 to 6 carbon atoms, provided that part of the methylene group constituting the alkylene group may be replaced with an oxygen atom or a carbonyl group, part or all of the hydrogen atoms constituting the alkylene group may be substituted with an aliphatic hydrocarbon group of 1 to 6 carbon atoms which may have a fluorine atom, and —Y—O-A- does not represent —C(═O)—O—C(═O)—; Q¹ and Q² each independently represents a fluorine atom or a linear or branched fluorinated alkyl group of 1 to 6 carbon atoms; and W⁺ represents a primary, secondary or tertiary ammonium coutercation which exhibits a pKa smaller than a pKa of $H_2N^+(X^2)-X^1-Y-O-A-C(Q^1)(Q^2)-SO_3^-$ generated by decomposition upon exposure.

2. A method of forming a resist pattern, comprising:
   applying the resist composition of claim 1 on a substrate to form a resist film,
   conducting exposure of the resist film, and
   developing the resist film to form a resist pattern.

3. A compound represented by general formula (i1) shown below:

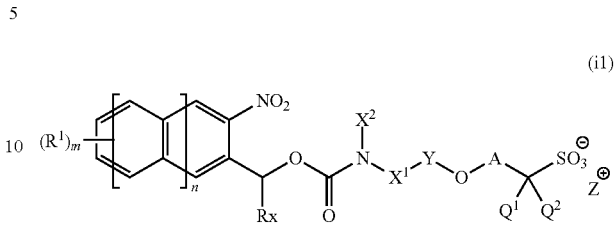

(i1)

wherein R¹ represents a hydrogen atom, a hydroxy group, a halogen atom, a linear or branched alkoxy group, a hydrocarbon group which may have a substituent, or a nitro group; m represents an integer of 0 to 4; n represents an integer of 0 to 3; Rx represents a hydrogen atom or a hydrocarbon group which may have a substituent; X¹ represents a divalent linking group and X² represents a hydrogen atom or a hydrocarbon group which may have a substituent, provided that X¹ and X² may be mutually bonded to form a ring with the nitrogen atom; Y represents a single bond or a carbonyl group, and A represents an alkylene group of 1 to 6 carbon atoms, provided that part of the methylene group constituting the alkylene group may be replaced with an oxygen atom or a carbonyl group, part or all of the hydrogen atoms constituting the alkylene group may be substituted with an aliphatic hydrocarbon group of 1 to 6 carbon atoms which may have a fluorine atom, and —Y—O-A- does not represent —C(═O)—O—C(═O)—; Q¹ and Q² each independently represents a fluorine atom or a linear or branched fluorinated alkyl group of 1 to 6 carbon atoms; and Z⁺ represents a metal cation or an onium cation.

* * * * *

UNITED STATES PATENT AND TRADEMARK OFFICE
CERTIFICATE OF CORRECTION

PATENT NO. : 8,900,795 B2
APPLICATION NO. : 13/738438
DATED : December 2, 2014
INVENTOR(S) : Yoshiyuki Utsumi, Hiroaki Shimizu and Jiro Yokoya It is certified that error appears in the above-identified patent and that said Letters Patent is hereby corrected as shown below:

On the title page
Page 1 (item 57 – abstract), line 16 "coutercation" should be --countercation--.
In the specification
Col. 5, line 22, "coutercation" should be --countercation--.
Col. 8, line 44, "sulfoneamide" should be --sulfonamide--.
Col. 8, line 51, "polycyclolefin" should be --polycycloolefin--.
Col. 15, line 24, "above the" should be --above--.
Col. 17, line 53; col. 18, line 23; and col. 21, line 6, "to" should be --to 5--.
Col. 53, lines 28 and 32, "(a1-0-16)" should be --(a1-1-16)--.
Col. 53, line 30, "(a1-0-02)" should be --(a1-1-02)--.
Col. 53, line 35, "(a1-0-02')" should be --(a1-1-02')--.
Col. 54, lines 12 and 19, "(a1-0-26)" should be --(a1-1-26)--.
Col. 54, line 15, "(a0-0-12)," should be --(a1-0-12),--.
Col. 54, lines 29 and 37, "(a1-0-1)," should be --(a1-1-1),--.
Col. 54, line 30, "(a1-1-1-15)" should be --(a1-1-15)--.
Col. 54, line 43, "(a1-0-35)" should be --(a1-1-35)--.
Col. 54, line 52, "(a1-0-4)" should be --(a1-1-4)--.
Col. 54, line 64; and col. 55, lines 46 and 54, "(a1-0-01)" should be --(a1-3-01)--.
Col. 54, line 66; and col. 55, line 57, "(a1-0-02)" should be --(a1-3-02)--.
Col. 54, line 67; col. 55, line 59; and col. 56, lines 18-19, "(a1-0-03)" should be --(a1-3-03)--.
Col. 55, line 55, "(a1-0-25)" should be --(a1-3-25)--.
Col. 55, line 58, "(a1-0-27)" should be --(a1-3-27)--.
Col. 56, lines 19-20 and line 21; col. 57, line 1; and col. 57, line 9, "(a1-0-03-1)" should be --(a1-3-03-1)--.
Col. 57, line 10, "(a1-0-29)" should be --(a1-3-29)--.

Signed and Sealed this
First Day of December, 2015

Michelle K. Lee
*Director of the United States Patent and Trademark Office*

Col. 63, lines 44-51:
" 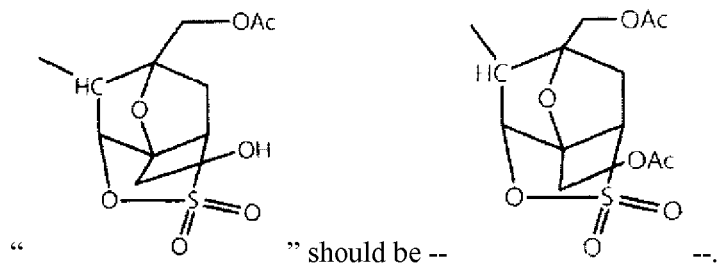 should be -- --.
Col. 65, line 15, "(a1-0-1)" should be --(3-1-1)--.
Col. 66, line 65, "(a1-0-11)" should be --(a0-0-11)--.
Col. 68, line 64, "β-propionolatone," should be --β-propiolactone,--.
Col. 80, lines 51-66:
" 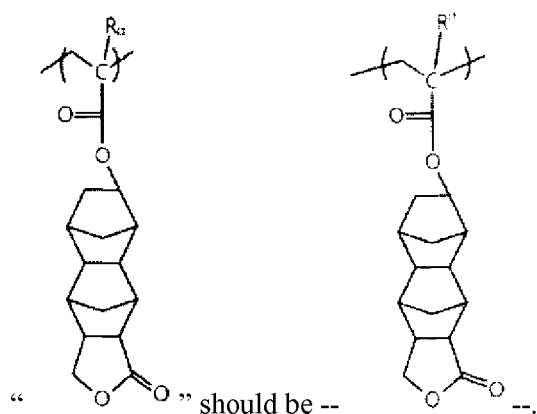 should be -- --.
Col. 81, lines 1-16:
" 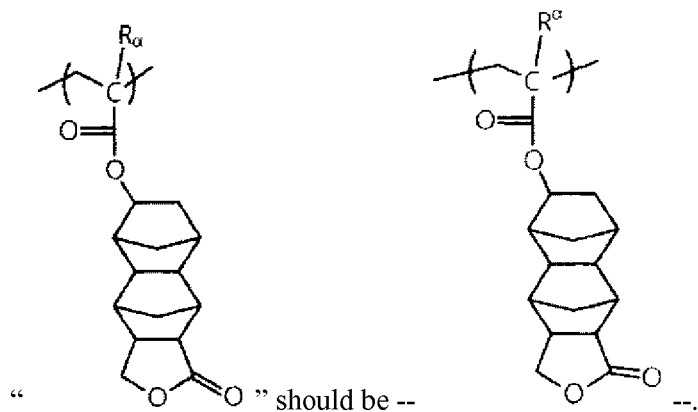 should be -- --.

Col. 81, lines 26-40:
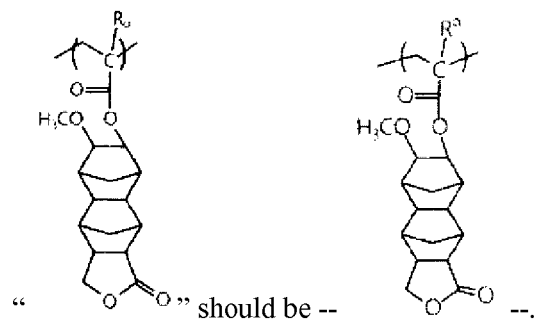
Col. 81, lines 51-66:
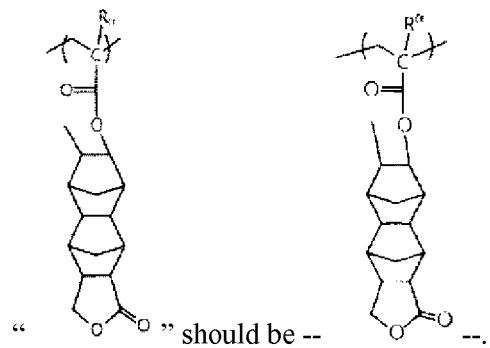
Col. 82, lines 1-22:
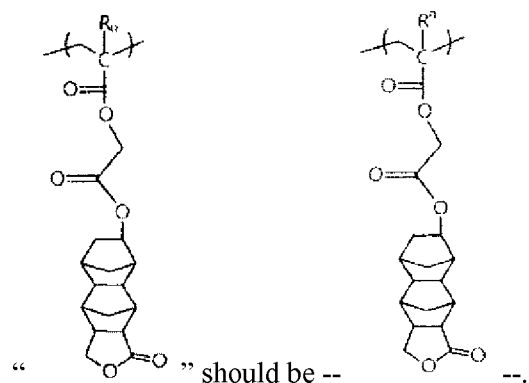

Col. 82, lines 23-42:
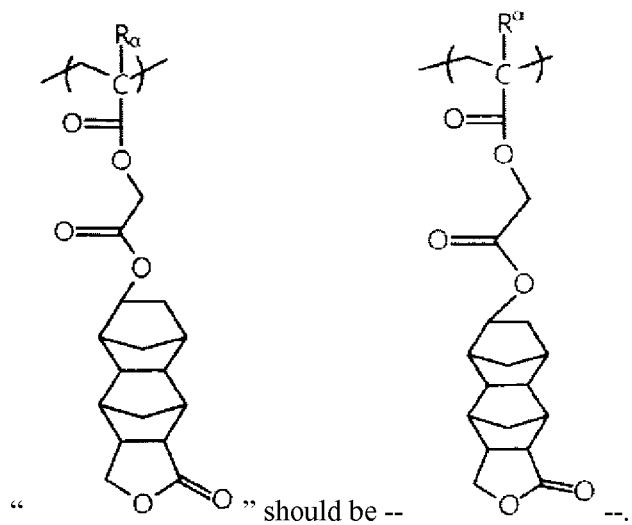
Col. 82, line 53, "(a1-0-1)," should be --(a2-1-1),--.
Col. 103, line 64; and col. 111, line 66, "coutercation" should be --countercation--.
Col. 108, line 6, "CH₁)" should be --CH₃)--.
Col. 111, lines 37-45:
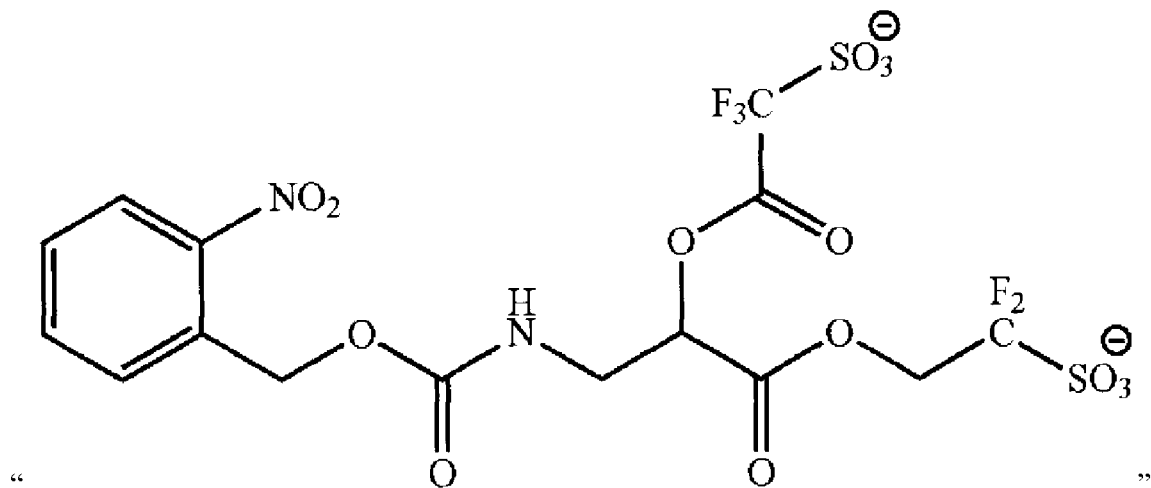
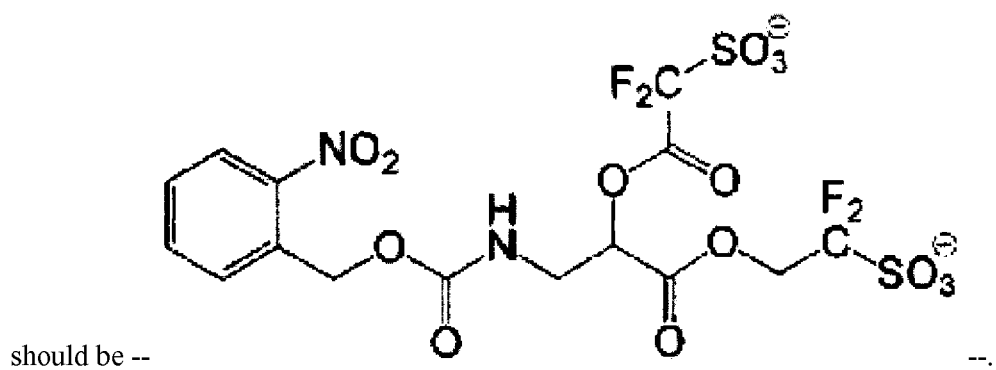

Col. 111, lines 52-62:
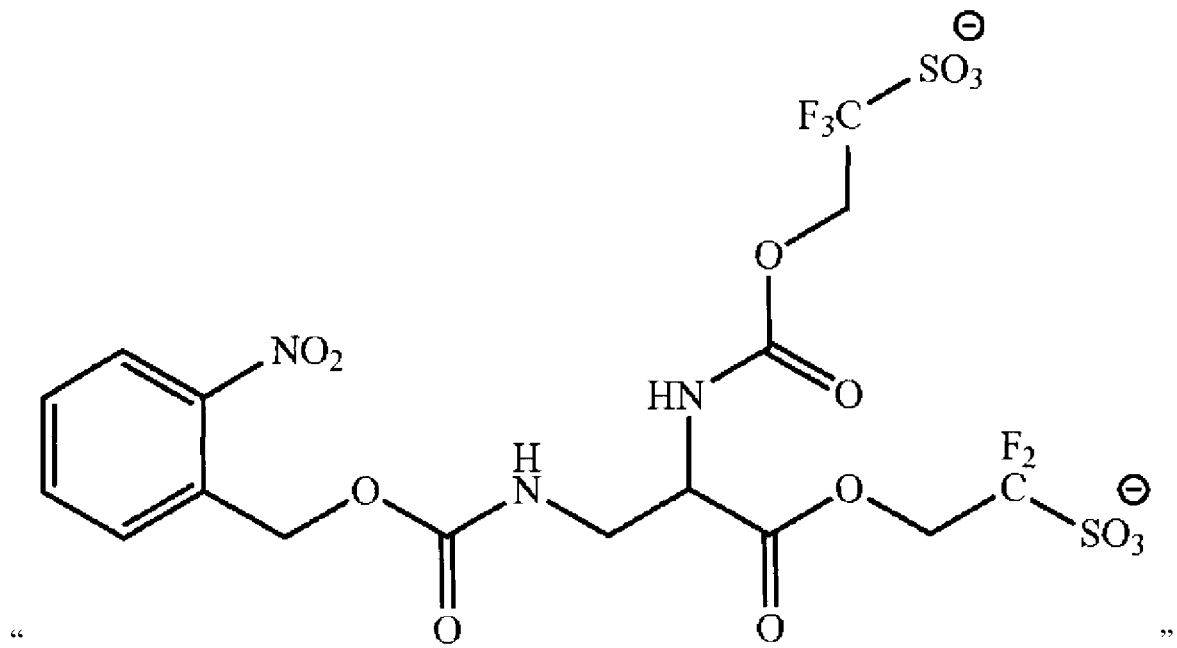
should be --
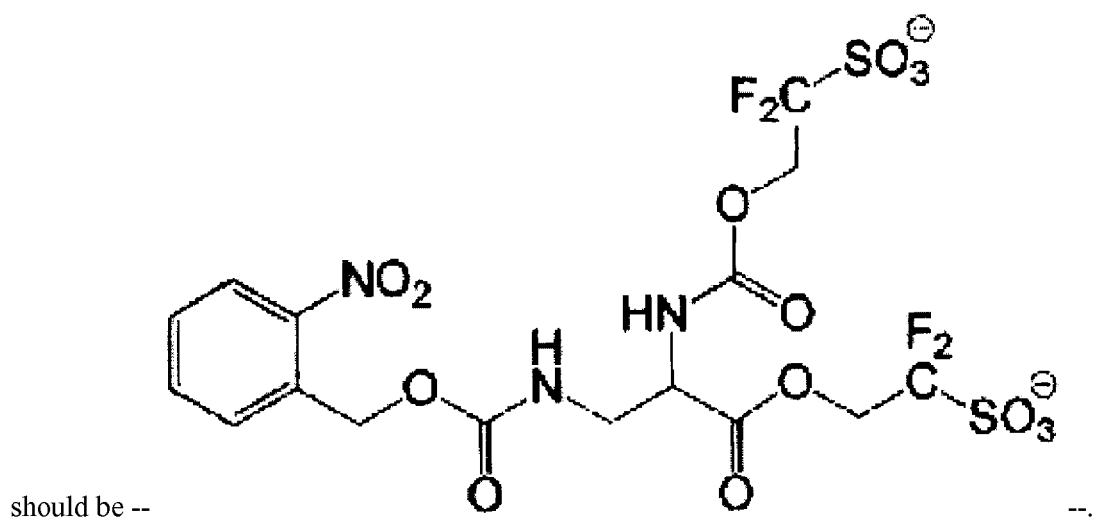
--.
Col. 111, line 66, "coutercation" should be --countercation--.
Col. 112, lines 26-30:
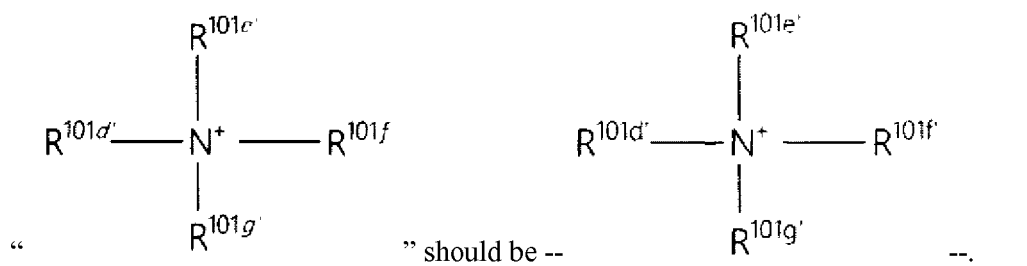
should be -- --.
Col. 112, line 44, "$R^{101'}$," should be --$R^{101d'}$,--.
Col. 116, lines 57 and 62, "moiety:the" should be --moiety : the--.
Col. 117, line 19, "$R^{103}d'$" should be --$R^{103d'}$--.
Col. 133, line 56, ""$R^{41}SO_3$"" should be --"$R^{4''}SO_3$"--.

CERTIFICATE OF CORRECTION (continued)
U.S. Pat. No. 8,900,795 B2

Col. 134, line 13, "to" should be --10 to--.
Col. 136, line 32, "R₄"SO³⁻" should be --R⁴"SO₃⁻--.
Col. 136, lines 52-58:

" 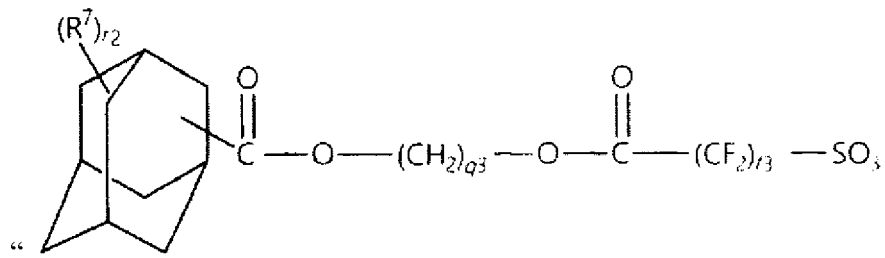 " should be

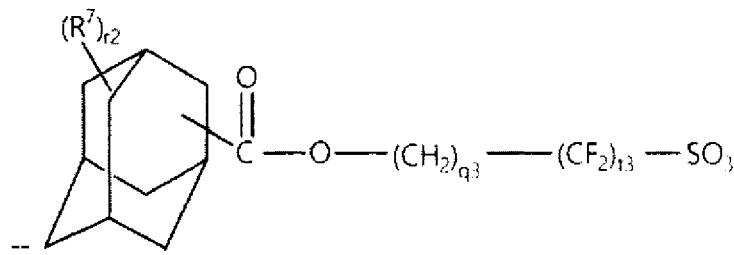 --.

Col. 139, line 60, "Rᶠ" should be --Rᶠ--.
Col. 142, line 5, "thereof" should be --thereof,--.
Col. 144, line 6, "recting" should be --reacting--.
Col. 149, lines 19 and 21, "R¹⁴" should be --Rf⁴--.
Col. 159, line 1, above the chemical formula, insert --[Chemical Formula 86]--.
Col. 163, line 46, "trialkylsily" should be --trialkylsilyl--.
Col. 163, line 65, "alipahtic" should be --aliphatic--.
Col. 165, line 62, "isooxyazole" should be --isoxazole.--.
Col. 170, line 32, "acidicty" should be --acidity--.
Col. 171, line 63, "at" should be --as--.
Col. 172, line 5, "C₄F9OCH₃," should be --C₄F₉OCH₃,--.
Col. 179-180, lines 1-9:

" 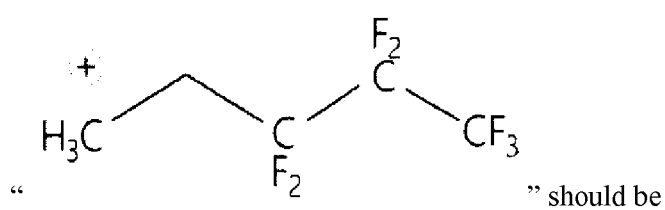 " should be

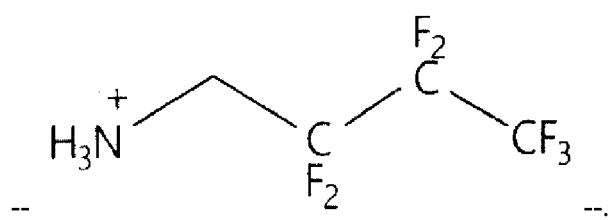 --.

Col. 179, line 67, "1 H" should be --1H--.
Col. 184, line 6, "30" should be --3σ--.
In the claims
Col. 185, line 30 (claim 1), "coutercation" should be --countercation--.